United States Patent
Talley et al.

[11] Patent Number: 6,090,834
[45] Date of Patent: Jul. 18, 2000

[54] SUBSTITUTED OXAZOLES FOR THE TREATMENT OF INFLAMMATION

[75] Inventors: John J Talley; Stephen R Bertenshaw, both of Brentwood; Donald J Rogier, Jr., Chesterfield; Matthew J Graneto, St. Louis, all of Mo.

[73] Assignee: G.D. Searle & Co., Skokie, Ill.

[21] Appl. No.: 09/203,451

[22] Filed: Dec. 1, 1998

Related U.S. Application Data

[63] Continuation of application No. 09/012,665, Jan. 23, 1998, abandoned, and a continuation of application No. 08/445,312, May 19, 1995, Pat. No. 5,558,554, which is a continuation-in-part of application No. PCT/US94/05395, May 19, 1994, Pat. No. 5,719,163, which is a continuation-in-part of application No. 08/065,730, May 21, 1993, Pat. No. 5,380,738.

[51] Int. Cl.$^7$ .................. A61K 31/421; A61K 31/422; A61K 31/427; C07D 263/32
[52] U.S. Cl. .......... 514/374; 514/340; 514/365; 514/372; 514/378; 514/397; 514/314; 514/333; 514/367; 546/256; 546/167; 546/275; 548/203; 548/205; 548/206; 548/235; 548/247; 548/152
[58] Field of Search .................. 548/235, 236, 548/152, 203; 514/374, 340, 365, 372, 378, 333; 546/275

[56] References Cited

U.S. PATENT DOCUMENTS

| | | | |
|---|---|---|---|
| 5,380,738 | 1/1995 | Norman et al. | 548/236 |
| 5,558,554 | 9/1996 | Finklea et al. | 445/52 |
| 5,719,163 | 2/1998 | Norman et al. | 548/235 |

FOREIGN PATENT DOCUMENTS

| | | |
|---|---|---|
| 91/19714 | 12/1991 | WIPO. |
| 92/21665 | 12/1992 | WIPO. |
| 94/15932 | 7/1994 | WIPO. |
| 94/27980 | 12/1994 | WIPO. |
| 95/00501 | 1/1995 | WIPO. |
| 96/36617 | 11/1996 | WIPO. |

OTHER PUBLICATIONS

N. Meanwell et al, *J. Med. Chem.*, 35, 3498 (1992).
R. Cremylin et al, *J. Heterocycl. Chem.*, 22, 1211 (1985).
T. Van Es and O.G. Backeberg, *J. Chem. Soc.*, 1363 (1963).
Haruta (II) Chem. Abstr vol. 125 entry 167971, Jun. 1996.
Haruta I Chem Abstr vol. 125 entry 167967, Jun. 1996.

*Primary Examiner*—John M. Ford
*Attorney, Agent, or Firm*—Joseph W. Bulock

[57] ABSTRACT

A class of substituted oxazolyl compounds is described for use in treating inflammation and inflammation-related disorders. Compounds of particular interest are defined by Formula II

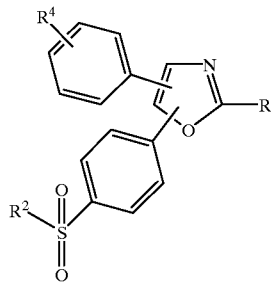

wherein R is selected from halo, mercapto, hydroxyl, lower carboxyalkylthio, lower haloalkoxy, lower alkylthio, lower alkylsulfinyl, lower alkylsulfonyl, lower alkoxy, aryloxy, lower alkylamino, aminocarbonyl, lower alkoxyalkyl, and lower carboxy(haloalkyl); wherein $R^2$ is selected from lower alkyl and amino; and wherein $R^4$ is selected from hydrido, lower alkyl, lower alkylamino, lower alkoxy and halo; or a pharmaceutically-acceptable salt thereof.

11 Claims, No Drawings

SUBSTITUTED OXAZOLES FOR THE TREATMENT OF INFLAMMATION

RELATED CASE

This application is a continuation of application Ser. No. 09/012,665, filed Jan. 23, 1998, now abandoned, a continuation of application Ser. No. 08/445,312, filed May 19, 1995, now abandoned, which is a continuation-in-part of International Application PCT/US94/05395, with an international filing date of May 19, 1994, issued as U.S. Pat. No. 5,719,163, which is a continuation-in-part of Ser. No. 08/065,730, filed May 21, 1993, issued as U.S. Pat. No. 5,380,738.

FIELD OF THE INVENTION

This invention is in the field of anti-inflammatory pharmaceutical agents and specifically relates to compounds, compositions and methods for treating inflammation and inflammation-associated disorders, such as arthritis.

BACKGROUND OF THE INVENTION

Prostaglandins play a major role in the inflammation process and the inhibition of prostaglandin production, especially production of $PGG_2$, $PGH_2$ and $PGE_2$, has been a common target of antiinflammatory drug discovery. However, common non-steroidal antiinflammatory drugs (NSAIDs) that are active in reducing the prostaglandin-induced pain and swelling associated with the inflammation process are also active in affecting other prostaglandin-regulated processes not associated with the inflammation process. Thus, use of high doses of most common NSAIDs can produce severe side effects, including life threatening ulcers, that limit their therapeutic potential. An alternative to NSAIDs is the use of corticosteroids, which have even more drastic side effects, especially when long term therapy is involved.

Previous NSAIDs have been found to prevent the production of prostaglandins by inhibiting enzymes in the human arachidonic acid/prostaglandin pathway, including the enzyme cyclooxygenase (COX). The recent discovery of an inducible enzyme associated with inflammation (named "cyclooxygenase-2 (COX-2)" or "prostaglandin G/H synthase II") provides a viable target of inhibition which more effectively reduces inflammation and produces fewer and less drastic side effects.

The references below that disclose antiinflammatory activity, show continuing efforts to find a safe and effective antiinflammatory agent. The novel oxazoles disclosed herein are such safe and also effective antiinflammatory agents furthering such efforts. The invention compounds are found to show usefulness in vivo as antiinflammatory agents with minimal side effects. The substituted oxazoles disclosed herein preferably selectively inhibit cyclooxygenase-2 over cyclooxygenase-1.

2,3-Diaryl-5-halo thiophenes are described in U.S. Pat. No. 4,590,205 as analgesic or antiinflammatory agents. More particularly, 2,3-diaryl-5-bromo thiophenes are described in U.S. Pat. No. 4,820,827 as having antiinflammatory and prostaglandin synthetase inhibitory activity for use in the treatment of inflammation and dysmenorrhea. PCT publication WO94/15932 describes 4,5-substitutedphenyl-thiophenes/furans and pyrroles as having antiinflammatory activity.

Pyrazole derivatives having antiinflammatory activity are described in U.S. Pat. No. 5,134,142, to Matsuo et al.

U.S. Pat. No. 3,578,671, to K. Brown, describes antiinflammatory 4,5-diphenyloxazoles substituted in the 2-position by a saturated or unsaturated aliphatic acid. U.S. Pat. No. 4,051,250, to J. Dahm et al, describes oxazole, imidazole and thiazole compounds, including 2-mercapto-4-(4-methylmercaptophenyl)-5-(4-chlorophenyl)oxazole, as having antiphlogistic, analgesic and antipyretic activity. Other related diphenyloxazole disclosures include U.S. Pat. No. 4,001,228, to G. Mattalia, for antiaggregating activity and U.S. Pat. No. 3,895,024, to R. Hafeli, for intermediates in the production of antiinflammatory agents. U.S. Pat. No. 4,489,084, to F. Haviv and F. Kerdesky, describes diphenyloxazolyl hydrazinoalkyl nitrile compounds for use as antiinflammatory agents. U.S. Pat. No. 4,143,047, to R. Harrison, describes oxazole compounds as reactants to make 2-acylamino oxazole derivatives having anti-allergy activity.

U.S. Pat. No. 4,791,124, to Lutomski et al, describes the pesticide activity of substituted bis(4-halophenyl)oxazoles. U.S. Pat. No. 4,775,687, to Meguro et al describes the possible use of 4,5-phenyl oxazoles as starting materials for antidiabetic compounds. WO publication No. WO92/21665, published Dec. 9, 1992, describes bis(halophenyl)oxazole derivatives as starting materials for the preparation of antiinflamnatory agents.

N. Meanwell et al [*J.Med.Chem.*, 35, 3498 (1992)] describe bis(substitutedphenyl)oxazoles as having ADP-induced platelet aggregation inhibition activity.

U.S. Pat. No. 4,812,470, to N. Rogers et al, describes phenyl substituted oxazoles as having antibacterial activity.

U.S. Pat. No. 3,901,908, to K. Fitzi and R. Pfister, describes 2-alkyl and 2-cycloalkyl-4,5-phenyloxazoles as intermediates in the synthesis of imidazoles having analgesic and antipyretic activity. Specifically, 2-tert-butyl-4-(4-methylsulfonylphenyl)-5-phenyloxazole is described.

U.S. Pat. No. 4,632,930, to Carini et al, describes antihypertensive alkyl and aryl substituted imidazole, thiazole and oxazole derivatives. Specifically, 5-phenyl-4-(4-methylsulfonylphenyl)-α,α-bis(trifluoromethyl)thiazole-2-methanol is described.

R. Cremylin et al describe the synthesis of heterocyclic sulfonyl derivatives and specifically, 4',4"-(2-methyl-4,5-oxazoldiyl)-bis-benzenesulfonamide (*J. Heterocycl.Chem.*, 22, 1211 (1985)).

T. van Es and O. G. Backeberg [*J.Chem.Soc.*, 1363 (1963)] describe the synthesis of 2-methyl-4,5-substitutedphenyloxazoles, and specifically, 4-[5-(4-chlorophenyl)-2-methyl-4-oxazolyl]benzenesulfonamide.

DESCRIPTION OF THE INVENTION

A class of substituted oxazolyl compounds useful in treating inflammation-related disorders is defined by Formula I:

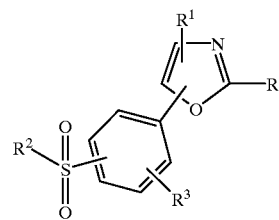

wherein R is selected from hydrido, halo, mercapto, hydroxyl, carboxyalkylthio, haloalkoxy, alkylthio, alkylsulfinyl, alkylsulfonyl, alkoxy, aryloxy, aralkoxy, alkylamino, aminocarbonyl, alkoxyalkyl, carboxy (haloalkyl), alkyl, hydroxyalkyl, haloalkyl, alkenyl, hydroxyalkenyl, alkynyl, hydroxyalkynyl, cycloalkyl, cycloalkylalkyl, alkoxycarbonyl, alkoxycarbonylalkyl, carboxy, carboxyalkyl, arylthioalkyl, aminocarbonylalkyl, alkylaminocarbonylalkyl, aryl, heteroaryl, aralkyl, aryloxyalkyl, aralkoxyalkyl, and heteroaryloxyalkyl;

wherein $R^1$ is selected from cycloalkyl, cycloalkenyl, aryl and heterocyclo, wherein $R^1$ is optionally substituted at a substitutable position by alkyl, alkylamino, alkoxy and halo;

wherein $R^2$ is selected from alkyl and amino; and wherein $R^3$ is selected from hydrido and alkyl;

or a pharmaceutically-acceptable salt thereof;

provided R is not methyl when $R^2$ is amino and when $R^1$ is phenyl or 4-halophenyl; further provided R is haloalkyl when $R^3$ is alkyl; and further provided that $R^1$ is not phenyl when $R^2$ is methyl and R is isopropyl or tert-butyl.

The phrase "further provided", as used in the above description, is intended to mean that the denoted proviso is not to be considered conjunctive with the other provisos.

Compounds of Formula I would be useful for, but not limited to, the treatment of inflammation in a subject, and for treatment of other inflammation-associated disorders, such as, as an analgesic in the treatment of pain and headaches, or as an antipyretic for the treatment of fever. For example, compounds of Formula I would be useful to treat arthritis, including but not limited to rheumatoid arthritis, spondyloarthopathies, gouty arthritis, osteoarthritis, systemic lupus erythematosus and juvenile arthritis. Such compounds of Formula I would be useful in the treatment of asthma, bronchitis, menstrual cramps, tendinitis, bursitis, and skin related conditions such as psoriasis, eczema, burns and dermatitis. Compounds of Formula I also would be useful to treat gastrointestinal conditions such as inflammatory bowel disease, Crohn's disease, gastritis, irritable bowel syndrome and ulcerative colitis and for the prevention of colorectal cancer. Compounds of Formula I would be useful in treating inflammation in such diseases as vascular diseases, migraine headaches, periarteritis nodosa, thyroiditis, aplastic anemia, Hodgkin's disease, sclerodoma, rheumatic fever, type I diabetes, myasthenia gravis, sarcoidosis, nephrotic syndrome, Behcet's syndrome, polymyositis, gingivitis, hypersensitivity, conjunctivitis, swelling occurring after injury, myocardial ischemia, and the like. The compounds are useful as anti-inflammatory agents, such as for the treatment of arthritis, with the additional benefit of having significantly less harmful side effects. Besides being useful for human treatment, these compounds are also useful for treatment of mammals, including horses, dogs, cats, rats, mice, sheep, pigs, etc.

Preferably, the compounds have a cyclooxygenase II $IC_{50}$ of less than about 0.1 $\mu$M, and also have a selectivity ratio of cyclooxygenase II inhibition over cyclooxygenase I inhibition of at least 50, and more preferably of at least 100. Even more preferably, the compounds have a cyclooxygenase I $IC_{50}$ of greater than about 0.5 $\mu$M, and more preferably of greater than 5 $\mu$M. Such preferred selectivity may indicate an ability to reduce the incidence of common NSAID-induced side effects.

The present compounds may also be used in co-therapies, partially or completely, in place of other conventional antiinflammatories, such as together with steroids, NSAIDS, 5-lipoxygenase inhibitors, $LTB_4$ inhibitors and $LTA_4$ hydrolase inhibitors.

The present invention preferably includes compounds which selectively inhibit cyclooxygenase-2 over cyclooxygenase-1. Preferably, the compounds have a cyclooxygenase-2 $IC_{50}$ of less than about 0.5 $\mu$M, and also have a selectivity ratio of cyclooxygenase-2 inhibition over cyclooxygenase-1 inhibition of at least 50, and more preferably of at least 100. Even more preferably, the compounds have a cyclooxygenase-1 $IC_{50}$ of greater than about 1 $\mu$M, and more preferably of greater than 20 $\mu$M. Such preferred selectivity may indicate an ability to reduce the incidence of common NSAID-induced side effects.

A preferred class of compounds consists of those compounds of Formula I wherein R is selected from hydrido, halo, mercapto, hydroxyl, lower carboxyalkylthio, lower haloalkoxy, lower alkylthio, lower alkylsulfinyl, lower alkylsulfonyl, lower alkoxy, aryloxy, lower aralkoxy, lower alkylamino, aminocarbonyl, lower alkoxyalkyl, lower carboxy(haloalkyl), lower alkyl, lower hydroxyalkyl, lower haloalkyl, lower alkenyl, lower hydroxyalkenyl, lower alkynyl, lower hydroxyalkynyl, lower cycloalkyl, lower cycloalkylalkyl, lower alkoxycarbonyl, lower alkoxycarbonylalkyl, carboxy, lower carboxyalkyl, lower arylthioalkyl, lower aminocarbonylalkyl, lower alkylaminocarbonylalkyl, aryl optionally substituted at a substitutable position by carboxy, lower alkyl, lower alkoxy and halo, heteroaryl optionally substituted at a substitutable position by carboxy, lower alkyl, lower alkoxy and halo, lower aralkyl optionally substituted at a substitutable position on the aryl radical by carboxy, lower alkyl, lower alkoxy and halo, lower aryloxyalkyl optionally substituted at a substitutable position with halo, carboxy, lower alkyl and lower alkoxy, aralkoxyalkyl optionally substituted at a substitutable position with halo, carboxy, lower alkyl and lower alkoxy, and heteroaryloxyalkyl optionally substituted at a substitutable position with halo, carboxy, lower alkyl and lower alkoxy; wherein $R^1$ is selected from lower cycloalkyl, lower cycloalkenyl, aryl and heteroaryl, wherein $R^1$ is optionally substituted at a substitutable position by lower alkyl, lower alkylamino, lower alkoxy and halo; wherein $R^2$ is selected from lower alkyl and amino; and wherein $R^3$ is selected from hydrido and lower alkyl; or a pharmaceutically-acceptable salt thereof.

A class of compounds of particular interest consists of those compounds of Formula I wherein R is selected from hydrido, chloro, fluoro, bromo, iodo, mercapto, hydroxyl, carboxymethylthio, carboxyethylthio, trifluoromethoxy, methylthio, ethylthio, methylsulfinyl, methylsulfonyl, methoxy, ethoxy, propoxy, butoxy, phenyloxy, benzyloxy, N-methylamino, N,N-dimethylamino, N,N-diethylamino, aminocarbonyl, methoxymethyl, α-bromo-carboxymethyl, methyl, ethyl, n-propyl, isopropyl, butyl, tert-butyl, isobutyl, hydroxymethyl, fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl, dichloropropyl, ethenyl, 1-propenyl, 2-propenyl, 1-butenyl, 2-butenyl, 3-butenyl, hydroxethenyl, ethynyl, 1-propynyl, 2-propynyl, 1-butynyl, 2-butynyl, 3-butynyl, hydroxyethynyl, cyclobutyl, cyclopentyl, cyclohexyl, cycloheptyl, cyclobutylmethyl, cyclopentylmethyl, cyclohexylmethyl, cyclohexylethyl, cyclohexylpropyl, cycloheptylmethyl, phenyl and naphthyl, optionally substituted at a substitutable position by fluoro, chloro, bromo, iodo, carboxy, methyl, ethyl, n-propyl, isopropyl, butyl, tert-butyl, isobutyl, methoxy, ethoxy, propoxy and butoxy, pyridyl, thienyl, thiazolyl, oxazolyl, imidazolyl, furyl and quinolyl, optionally substituted at a substitutable position by fluoro, chloro, bromo, iodo, carboxy, methyl, ethyl, n-propyl, isopropyl, butyl, tert-butyl, isobutyl, methoxy, ethoxy, propoxy and butoxy, benzyl, phenethyl, diphenylmethyl and phenylpropyl, optionally substituted at a substitutable position on the phenyl radical by fluoro, chloro, bromo, iodo, carboxy, methyl, ethyl, n-propyl, isopropyl, butyl, tert-butyl, isobutyl, methoxy, ethoxy, propoxy and butoxy, phenoxymethyl optionally substituted at a substitutable position on the phenyl radical with fluoro, chloro, bromo, iodo, carboxy, methyl, ethyl, n-propyl, isopropyl, butyl, tert-butyl, isobutyl, methoxy, ethoxy, propoxy and butoxy, benzyloxymethyl optionally substituted at a substitutable position on the phenyl radical with fluoro, chloro, bromo, iodo, carboxy, methyl, ethyl, n-propyl, isopropyl, butyl, tert-butyl, isobutyl, methoxy, ethoxy, propoxy and butoxy, pyridyloxymethyl and quinolyloxymethyl optionally substituted at a substitutable position with fluoro, chloro, bromo, iodo, carboxy, methyl, ethyl, n-propyl, isopropyl, butyl, tert-butyl, isobutyl, methoxy, ethoxy, propoxy and butoxy, methoxycarbonyl, ethoxycarbonyl, propoxycarbonyl, butoxycarbonyl, methoxycarbonylmethyl, ethoxycarbonylmethyl, methoxycarbonylethyl, ethoxycarbonylethyl, carboxy, acetyl, propanoic, butanoic, pentanoic, hexanoic, phenylthiomethyl, aminocarbonylmethyl, N-methylaminocarbonylmethyl and N,N-dimethylaminocarbonylmethyl; wherein $R^1$ is selected from cyclobutyl, cyclopentyl, cyclohexyl, cycloheptyl, 1-cyclohexenyl, 2-cyclohexenyl, 3-cyclohexenyl, cyclopentenyl, cycloheptenyl, phenyl, naphthyl, pyridyl, thienyl, thiazolyl, oxazolyl, imidazolyl, furyl, quinolyl, benzothiazolyl, 2,3-thianaphthalenyl, 2,3-dihydrothianaphthalenyl, 2,3-benzofuryl, and 2,3-dihydrobenzofuryl, wherein $R^1$ is optionally substituted at a substitutable position by methyl, ethyl, n-propyl, isopropyl, butyl, tert-butyl, isobutyl, amino, methoxy, ethoxy, propoxy, butoxy, N-methylamino, N,N-dimethylamino, fluoro, chloro, bromo and iodo; wherein $R^2$ is selected from methyl, and amino; wherein $R^3$ is selected from hydrido, and methyl.

Within Formula I there is a subclass of compounds of high interest represented by Formula II:

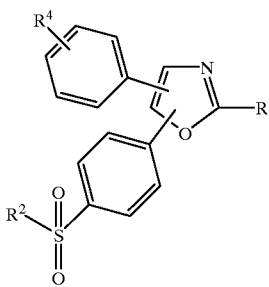

II wherein R is selected from halo, mercapto, lower carboxyalkylthio, lower haloalkoxy, lower alkylthio, lower alkylsulfinyl, lower alkylsulfonyl, lower alkoxy, aryloxy, lower alkylamino, aminocarbonyl, lower alkoxyalkyl, and lower carboxy(haloalkyl); wherein $R^2$ is selected from lower alkyl and amino; and wherein $R^4$ is selected from hydrido, lower alkyl, amino, lower alkoxy and halo; or a pharmaceutically-acceptable salt thereof.

A class of compounds of particular interest consists of those compounds of Formula II wherein R is selected from chloro, fluoro, bromo, iodo, mercapto, carboxymethylthio, carboxyethylthio, trifluoromethoxy, methylthio, ethylthio, methylsulfinyl, methylsulfonyl, methoxy, ethoxy, propoxy, butoxy, phenyloxy, benzyloxy, N-methylamino, N,N-dimethylamino, N,N-diethylamino, aminocarbonyl, methoxymethyl, α-bromo-carboxymethyl; wherein $R^2$ is selected from methyl, ethyl, n-propyl, isopropyl, butyl, tert-butyl, isobutyl and amino; and wherein $R^4$ is selected from hydrido, methyl, ethyl, n-propyl, isopropyl, butyl, tert-butyl, isobutyl, amino, methoxy, ethoxy, propoxy, butoxy, and halo; or a pharmaceutically-acceptable salt thereof.

A family of specific compounds of particular interest within Formulas I–II consists of compounds and pharmaceutically-acceptable salts thereof as follows:

ethyl [4-(4-aminosulfonylphenyl)-5-(3-fluoro-4-methoxyphenyl)]-2-oxazoleacetate;
[4-(4-aminosulfonylphenyl)-5-cyclohexyl]-2-oxazoleacetic acid;
[5-(4-aminosulfonylphenyl)-4-(4-chlorophenyl)]-2-oxazoleacetic acid;
[4-(4-aminosulfonylphenyl)-5-(4-chlorophenyl)]-2-oxazoleacetic acid;
[4-(4-aminosulfonylphenyl)-5-(3-chloro-4-fluorophenyl)]-2-oxazoleacetic acid;
[4-(4-aminosulfonylphenyl)-5-(3,4-dichlorophenyl)]-2-oxazoleacetic acid;
[4-(4-aminosulfonylphenyl-5-(3,4-difluorophenyl)]-2-oxazoleacetic acid;
[5-(3,4-difluorophenyl)-2-trifluoromethyl-4-oxazolyl] benzenesulfonamide;
[5-(4-aminosulfonylphenyl)-4-phenyl]-2-oxazolepropionic acid;
4-[4-phenyl-5-oxazolyl]benzenesulfonamide;
4-[2-chloro-4-phenyl-5-oxazolyl]benzenesulfonamide;
4-[2-mercapto-4-phenyl-5-oxazolyl]benzenesulfonamide;
4-[2-(3-chlorophenoxy)-4-phenyl-5-(oxazolyl] benzenesulfonamide;
5-(4-aminosulfonylphenyl)-4-phenyl-2-oxazolemercaptoacetic acid;
4-[4-phenyl-2-(2,2,2-trifluoroethoxy-5-oxazolyl] benzenesulfonamide;
4-[2-(methylthio)-4-phenyl-5-oxazolyl] benzenesulfonamide;
4-[2-methyl-4-phenyl-5-oxazolyl]benzenesulfonamide;
4-[2-methylsulfinyl)-4-phenyl-5-oxazolyl] benzenesulfonamide;
4-[2-(methylsulfonyl)-4-phenyl-5-oxazolyl] benzenesulfonamide;
4-[2-(2,3,4,5,6-pentafluorophenoxy)-4-phenyl-5-oxazolyl] benzenesulfonamide;
4-[2-methoxy-4-phenyl-5-oxazolyl]benzenesulfonamide;
ethyl 2-[[5-(4-aminosulfonylphenyl)-4-phenyl-2-oxazolyl] oxy]benzoate;
ethyl 3-[[5-(4-aminosulfonylphenyl)-4-phenyl-2-oxazolyl] oxy]benzoate;
4-[2-(N,N-dimethylamino)-4-phenyl-5-oxazolyl] benzenesulfonamide;
4-[5-(4-chlorophenyl)-2-trifluoromethyl-4-oxazolyl] benzenesulfonamide;
4-[5-(3-fluoro-4-methoxyphenyl-2-trifluoromethyl)-4-oxazolyl]benzenesulfonamide;
4-methyl-3-[5-phenyl-2-trifluoromethyl-4-oxazolyl] benzenesulfonamide;
4-[4-(3-aminosulfonyl-4-methylphenyl)-2-trifluoromethyl-5-oxazolyl]benzenesulfonamide;
4-methyl-3-[4-phenyl-2-trifluoromethyl-5-oxazolyl] benzenesulfonamide;

4-[4-(N,N-dimethylamino)phenyl-2-trifluoromethyl-5-oxazolyl]benzenesulfonamide;
[4-(4-aminosulfonylphenyl)-5-(3-fluoro-4-methoxyphenyl)]-2-oxazoleacetic acid;
4-[4-aminosulfonylphenyl)-5-(3-fluoro-4-methoxyphenyl)-2-oxazolyl]α-bromoacetic acid;
4-(4-methylphenyl)-5-(4-methylsulfonylphenyl)-2-trifluoromethyloxazole;
4-[5-(3-fluoro-4-methoxyphenyl)-2-methyl-4-oxazolyl]benzenesulfonamide;
5-(3-fluoro-4-methoxyphenyl)-4-(4-methylsulfonylphenyl)-2-trifluoromethyloxazole;
4-[5-(3-bromo-4-methoxy-5-fluorophenyl)-2-trifluoromethyl-4-oxazolyl]benzenesulfonamide;
[5-(4-aminosulfonylphenyl)-4-phenyl]-2-oxazolecarboxamide;
4-[2-methoxymethyl-4-phenyl-5-oxazolyl]benzenesulfonamide;
4-[2-benzyl-5-(phenyl)-4-oxazolyl]benzenesulfonamide;
4-[2-benzyl-5-(2-fluorophenyl)-4-oxazolyl]benzenesulfonamide;
4-[2-benzyl-5-(3-fluorophenyl)-4-oxazolyl]benzenesulfonamide;
4-[2-benzyl-5-(4-fluorophenyl)-4-oxazolyl]benzenesulfonamide;
4-[2-benzyl-5-(2,4-difluorophenyl)-4-oxazolyl]benzenesulfonamide;
4-[2-benzyl-5-(2,5-difluorophenyl)-4-oxazolyl]benzenesulfonamide;
4-[2-benzyl-5-(2,6-difluorophenyl)-4-oxazolyl]benzenesulfonamide;
4-[2-benzyl-5-(3,4-difluorophenyl)-4-oxazolyl]benzenesulfonamide;
4-[2-benzyl-5-(3,5-difluorophenyl)-4-oxazolyl]benzenesulfonamide;
4-[2-benzyl-5-(2-chlorophenyl)-4-oxazolyl]benzenesulfonamide;
4-[2-benzyl-5-(3-chlorophenyl)-4-oxazolyl]benzenesulfonamide;
4-[2-benzyl-5-(4-chlorophenyl)-4-oxazolyl]benzenesulfonamide;
4-[2-benzyl-5-(2,4-dichlorophenyl)-4-oxazolyl]benzenesulfonamide;
4-[2-benzyl-5-(2,5-dichlorophenyl)-4-oxazolyl]benzenesulfonamide;
4-[2-benzyl-5-(2,6-dichlorophenyl)-4-oxazolyl]benzenesulfonamide;
4-[2-benzyl-5-(3,4-dichlorophenyl)-4-oxazolyl]benzenesulfonamide;
4-[2-benzyl-5-(3,5-dichlorophenyl)-4-oxazolyl]benzenesulfonamide;
4-[2-benzyl-5-(2-methoxyphenyl)-4-oxazolyl]benzenesulfonamide;
4-[2-benzyl-5-(3-methoxyphenyl)-4-oxazolyl]benzenesulfonamide;
4-[2-benzyl-5-(4-methoxyphenyl)-4-oxazolyl]benzenesulfonamide;
4-[2-benzyl-5-(2,4-dimethoxyphenyl)-4-oxazolyl]benzenesulfonamide;
4-[2-benzyl-5-(2,5-dimethoxyphenyl)-4-oxazolyl]benzenesulfonamide;
4-[2-benzyl-5-(2,6-dimethoxyphenyl)-4-oxazolyl]benzenesulfonamide;
4-[2-benzyl-5-(3,4-dimethoxyphenyl)-4-oxazolyl]benzenesulfonamide;
4-[2-benzyl-5-(3,5-dimethoxyphenyl)-4-oxazolyl]benzenesulfonamide;
4-[2-benzyl-5-(2-methylphenyl)-4-oxazolyl]benzenesulfonamide;
4-[2-benzyl-5-(3-methylphenyl)-4-oxazolyl]benzenesulfonamide;
4-[2-benzyl-5-(4-methylphenyl)-4-oxazolyl]benzenesulfonamide;
4-[2-benzyl-5-(2,4-dimethylphenyl)-4-oxazolyl]benzenesulfonamide;
4-[2-benzyl-5-(2,5-dimethylphenyl)-4-oxazolyl]benzenesulfonamide;
4-[2-benzyl-5-(2,6-dimethylphenyl)-4-oxazolyl]benzenesulfonamide;
4-[2-benzyl-5-(3,4-dimethylphenyl)-4-oxazolyl]benzenesulfonamide;
4-[2-benzyl-5-(3,5-dimethylphenyl)-4-oxazolyl]benzenesulfonamide;
4-[2-benzyl-5-(2-chloro-4-methylphenyl)-4-oxazolyl]benzenesulfonamide;
4-[2-benzyl-5-(3-chloro-4-methylphenyl)-4-oxazolyl]benzenesulfonamide;
4-[2-benzyl-5-(3-chloro-2-methylphenyl)-4-oxazolyl]benzenesulfonamide;
4-[2-benzyl-5-(2-chloro-6-methylphenyl)-4-oxazolyl]benzenesulfonamide;
4-[2-benzyl-5-(4-chloro-2-methylphenyl)-4-oxazolyl]benzenesulfonamide;
4-[2-benzyl-5-(4-chloro-3-methylphenyl)-4-oxazolyl]benzenesulfonamide;
4-[2-benzyl-5-(2-chloro-4-methoxyphenyl)-4-oxazolyl]benzenesulfonamide;
4-[2-benzyl-5-(3-chloro-4-methoxyphenyl)-4-oxazolyl]benzenesulfonamide;
4-[2-benzyl-5-(3-chloro-2-methoxyphenyl)-4-oxazolyl]benzenesulfonamide;
4-[2-benzyl-5-(2-chloro-6-methoxyphenyl)-4-oxazolyl]benzenesulfonamide;
4-[2-benzyl-5-(4-chloro-2-methoxyphenyl)-4-oxazolyl]benzenesulfonamide;
4-[2-benzyl-5-(4-chloro-3-methoxyphenyl)-4-oxazolyl]benzenesulfonamide;
4-[2-benzyl-5-(3,5-dichloro-4-methoxyphenyl)-4-oxazolyl]benzenesulfonamide;
4-[2-benzyl-5-(2-fluoro-4-methylphenyl)-4-oxazolyl]benzenesulfonamide;
4-[2-benzyl-5-(3-fluoro-4-methylphenyl)-4-oxazolyl]benzenesulfonamide;
4-[2-benzyl-5-(3-fluoro-2-methylphenyl)-4-oxazolyl]benzenesulfonamide;
4-[2-benzyl-5-(2-fluoro-6-methylphenyl)-4-oxazolyl]benzenesulfonamide;
4-[2-benzyl-5-(4-fluoro-2-methylphenyl)-4-oxazolyl]benzenesulfonamide;
4-[2-benzyl-5-(4-fluoro-3-methylphenyl)-4-oxazolyl]benzenesulfonamide;
4-[2-benzyl-5-(2-fluoro-4-methoxyphenyl)-4-oxazolyl]benzenesulfonamide;
4-[2-benzyl-5-(3-fluoro-4-methoxyphenyl)-4-oxazolyl]benzenesulfonamide;
4-[2-benzyl-5-(3-fluoro-2-methoxyphenyl)-4-oxazolyl]benzenesulfonamide;
4-[2-benzyl-5-(2-fluoro-6-methoxyphenyl)-4-oxazolyl]benzenesulfonamide;
4-[2-benzyl-5-(4-fluoro-2-methoxyphenyl)-4-oxazolyl]benzenesulfonamide;
4-[2-benzyl-5-(2-thienyl)-4-oxazolyl]benzenesulfonamide;
4-[2-benzyl-5-(5-chloro-2-thienyl)-4-oxazolyl]benzenesulfonamide;

4-[2-benzyl-5-(yl)-4-oxazolyl]benzenesulfonamide;
4-[2-benzyl-5-(1-cyclohexenyl)-4-oxazolyl]benzenesulfonamide;
4-[2-benzyl-5-(2-cyclohexenyl)-4-oxazolyl]benzenesulfonamide;
4-[2-benzyl-5-(3-cyclohexenyl)-4-oxazolyl]benzenesulfonamide;
2-benzyl-4-(4-methylsulfonylphenyl)-5-phenyloxazole;
2-benzyl-4-(4-methylsulfonylphenyl)-5-(2-fluorophenyl)oxazole;
2-benzyl-4-(4-methylsulfonylphenyl)-5-(3-fluorophenyl)oxazole;
2-benzyl-4-(4-methylsulfonylphenyl)-5-(2,4-difluorophenyl)oxazole;
2-benzyl-4-(4-methylsulfonylphenyl)-5-(2,5-difluorophenyl)oxazole;
2-benzyl-4-(4-methylsulfonylphenyl)-5-(2,6-difluorophenyl)oxazole;
2-benzyl-4-(4-methylsulfonylphenyl)-5-(3,4-difluorophenyl)oxazole;
2-benzyl-4-(4-methylsulfonylphenyl)-5-(3,5-difluorophenyl)oxazole;
2-benzyl-4-(4-methylsulfonylphenyl)-5-(2-chlorophenyl)oxazole;
2-benzyl-4-(4-methylsulfonylphenyl)-5-(3-chlorophenyl)oxazole;
2-benzyl-4-(4-methylsulfonylphenyl)-5-(4-chlorophenyl)oxazole;
2-benzyl-4-(4-methylsulfonylphenyl)-5-(2,4-dichlorophenyl)oxazole;
2-benzyl-4-(4-methylsulfonylphenyl)-5-(2,5-dichlorophenyl)oxazole;
2-benzyl-4-(4-methylsulfonylphenyl)-5-(2,6-dichlorophenyl)oxazole;
2-benzyl-4-(4-methylsulfonylphenyl)-5-(3,4-dichlorophenyl)oxazole;
2-benzyl-4-(4-methylsulfonylphenyl)-5-(3,5-dichlorophenyl)oxazole;
2-benzyl-4-(4-methylsulfonylphenyl)-5-(2-methoxyphenyl)oxazole;
2-benzyl-4-(4-methylsulfonylphenyl)-5-(3-methoxyphenyl)oxazole;
2-benzyl-4-(4-methylsulfonylphenyl)-5-(4-methoxyphenyl)oxazole;
2-benzyl-4-(4-methylsulfonylphenyl)-5-(2,4-dimethoxyphenyl)oxazole;
2-benzyl-4-(4-methylsulfonylphenyl)-5-(2,5-dimethoxyphenyl)oxazole;
2-benzyl-4-(4-methylsulfonylphenyl)-5-(2,6-dimethoxyphenyl)oxazole;
2-benzyl-4-(4-methylsulfonylphenyl)-5-(3,4-dimethoxyphenyl)oxazole;
2-benzyl-4-(4-methylsulfonylphenyl)-5-(3,5-dimethoxyphenyl)oxazole;
2-benzyl-4-(4-methylsulfonylphenyl)-5-(2-methylphenyl)oxazole;
2-benzyl-4-(4-methylsulfonylphenyl)-5-(3-methylphenyl)oxazole;
2-benzyl-4-(4-methylsulfonylphenyl)-5-(4-methylphenyl)oxazole;
2-benzyl-4-(4-methylsulfonylphenyl)-5-(2,4-dimethylphenyl)oxazole;
2-benzyl-4-(4-methylsulfonylphenyl)-5-(2,5-dimethylphenyl)oxazole;
2-benzyl-4-(4-methylsulfonylphenyl)-5-(2,6-dimethylphenyl)oxazole;
2-benzyl-4-(4-methylsulfonylphenyl)-5-(3,4-dimethylphenyl)oxazole;
2-benzyl-4-(4-methylsulfonylphenyl)-5-(3,5-dimethylphenyl)oxazole;
2-benzyl-4-(4-methylsulfonylphenyl)-5-(2-chloro-4-methylphenyl)oxazole;
2-benzyl-4-(4-methylsulfonylphenyl)-5-(3-chloro-4-methylphenyl)oxazole;
2-benzyl-4-(4-methylsulfonylphenyl)-5-(3-chloro-2-methylphenyl)oxazole;
2-benzyl-4-(4-methylsulfonylphenyl)-5-(2-chloro-6-methylphenyl)oxazole;
2-benzyl-4-(4-methylsulfonylphenyl)-5-(4-chloro-2-methylphenyl)oxazole;
2-benzyl-4-(4-methylsulfonylphenyl)-5-(4-chloro-3-methylphenyl)oxazole;
2-benzyl-4-(4-methylsulfonylphenyl)-5-(2-chloro-4-methoxyphenyl)oxazole;
2-benzyl-4-(4-methylsulfonylphenyl)-5-(3-chloro-4-methoxyphenyl)oxazole;
2-benzyl-4-(4-methylsulfonylphenyl)-5-(3-chloro-2-methoxyphenyl)oxazole;
2-benzyl-4-(4-methylsulfonylphenyl)-5-(2-chloro-6-methoxyphenyl)oxazole;
2-benzyl-4-(4-methylsulfonylphenyl)-5-(4-chloro-2-methoxyphenyl)oxazole;
2-benzyl-4-(4-methylsulfonylphenyl)-5-(4-chloro-3-methoxyphenyl)oxazole;
2-benzyl-4-(4-methylsulfonylphenyl)-5-(3,5-dichloro-4-methoxyphenyl)oxazole;
2-benzyl-4-(4-methylsulfonylphenyl)-5-(2-fluoro-4-methylphenyl)oxazole;
2-benzyl-4-(4-methylsulfonylphenyl)-5-(3-fluoro-4-methylphenyl)oxazole;
2-benzyl-4-(4-methylsulfonylphenyl)-5-(3-fluoro-2-methylphenyl)oxazole;
2-benzyl-4-(4-methylsulfonylphenyl)-5-(2-fluoro-6-methylphenyl)oxazole;
2-benzyl-4-(4-methylsulfonylphenyl)-5-(4-fluoro-2-methylphenyl)oxazole;
2-benzyl-4-(4-methylsulfonylphenyl)-5-(4-fluoro-3-methylphenyl)oxazole;
2-benzyl-4-(4-methylsulfonylphenyl)-5-(2-fluoro-4-methoxyphenyl)oxazole;
2-benzyl-4-(4-methylsulfonylphenyl)-5-(3-fluoro-4-methoxyphenyl)oxazole;
2-benzyl-4-(4-methylsulfonylphenyl)-5-(3-fluoro-2-methoxyphenyl)oxazole;
2-benzyl-4-(4-methylsulfonylphenyl)-5-(2-fluoro-6-methoxyphenyl)oxazole;
2-benzyl-4-(4-methylsulfonylphenyl)-5-(4-fluoro-2-methoxyphenyl)oxazole;
2-benzyl-4-(4-methylsulfonylphenyl)-5-(2-thienyl)oxazole;
2-benzyl-4-(4-methylsulfonylphenyl)-5-(5-chloro-2-thienyl)oxazole;
2-benzyl-4-(4-methylsulfonylphenyl)-5-(cyclohexyl)oxazole;
2-benzyl-4-(4-methylsulfonylphenyl)-5-(1-cyclohexenyl)oxazole;
2-benzyl-4-(4-methylsulfonylphenyl)-5-(2-cyclohexenyl)oxazole;
2-benzyl-4-(4-methylsulfonylphenyl)-5-(3-cyclohexenyl)oxazole;
2-(ethyl)-4-(4-methylsulfonylphenyl)-5-phenyloxazole;
2-(trifluoromethyl)-4-(4-methylsulfonylphenyl)-5-phenyloxazole;
2-(difluoromethyl)-4-(4-methylsulfonylphenyl)-5-phenyloxazole;
2-(hydroxymethyl)-4-(4-methylsulfonylphenyl)-5-phenyloxazole;

[4-(4-methylsulfonylphenyl)-5-phenyl]-2-oxazolecarboxylic acid;
methyl [4-(4-methylsulfonylphenyl)-5-phenyl]-2-oxazolecarboxylate;
ethyl [4-(4-methylsulfonylphenyl)-5-phenyl]-2-oxazolecarboxylate;
2-(propyl)-4-(4-methylsulfonylphenyl)-5-phenyloxazole;
2-(benzyl)-4-(4-methylsulfonylphenyl)-5-phenyloxazole;
2-(phenylthiomethyl)-4-(4-methylsulfonylphenyl)-5-phenyloxazole;
2-(phenoxymethyl)-4-(4-methylsulfonylphenyl)-5-phenyloxazole;
2-((4-chlorophenoxy)methyl)-4-(4-methylsulfonylphenyl)-5-phenyloxazole;
2-((3-chlorophenoxy)methyl)-4-(4-methylsulfonylphenyl)-5-phenyloxazole;
2-((2-chlorophenoxy)methyl)-4-(4-methylsulfonylphenyl)-5-phenyloxazole;
2-((4-fluorophenoxy)methyl)-4-(4-methylsulfonylphenyl)-5-phenyloxazole;
2-((3-fluorophenoxy)methyl)-4-(4-methylsulfonylphenyl)-5-phenyloxazole;
2-((2-fluorophenoxy)methyl)-4-(4-methylsulfonylphenyl)-5-phenyloxazole;
2-((4-carboxyphenoxy)methyl)-4-(4-methylsulfonylphenyl)-5-phenyloxazole;
2-((3-carboxyphenoxy)methyl)-4-(4-methylsulfonylphenyl)-5-phenyloxazole;
2-((2-carboxyphenoxy)methyl)-4-(4-methylsulfonylphenyl)-5-phenyloxazole;
2-(2-phenethyl)-4-(4-methylsulfonylphenyl)-5-phenyloxazole;
2-(3-phenylpropyl)-4-(4-methylsulfonylphenyl)-5-phenyloxazole;
[4-(4-methylsulfonylphenyl)-5-phenyl]-2-oxazoleacetic acid;
ethyl [4-(4-methylsulfonylphenyl)-5-phenyl]-2-oxazoleacetate;
methyl [4-(4-methylsulfonylphenyl)-5-phenyl]-2-oxazoleacetate;
[4-(4-methylsulfonylphenyl)-5-phenyl]-2-oxazolepropanoic acid;
ethyl [4-(4-methylsulfonylphenyl)-5-phenyl]-2-oxazolepropanoate;
methyl [4-(4-methylsulfonylphenyl)-5-phenyl]-2-oxazolepropanoate;
[4-(4-methylsulfonylphenyl)-5-phenyl]-2-oxazolebutanoic acid;
ethyl [4-(4-methylsulfonylphenyl)-5-phenyl]-2-oxazolebutanoate;
methyl [4-(4-methylsulfonylphenyl)-5-phenyl]-2-oxazolebutanoate;
2-(2-quinolyloxymethyl)-4-(4-methylsulfonylphenyl)-5-phenyloxazole;
4-[2-(ethyl)-5-phenyl-4-oxazolyl]benzenesulfonamide;
4-[2-(trifluoromethyl)-5-phenyl-4-oxazolyl]benzenesulfonamide;
4-[2-(difluoromethyl)-5-phenyl-4-oxazolyl]benzenesulfonamide;
4-[2-(hydroxymethyl)-5-phenyl-4-oxazolyl]benzenesulfonamide;
[4-(4-aminosulfonylphenyl)-5-phenyl]-2-oxazolecarboxylic acid;
methyl [4-(4-aminosulfonylphenyl)-5-phenyl]-2-oxazolecarboxylate;
ethyl [4-(4-aminosulfonylphenyl)-5-phenyl]-2-oxazolecarboxylate;
4-[2-(propyl)-5-phenyl-4-oxazolyl]benzenesulfonamide;
4-[2-(benzyl)-5-phenyl-4-oxazolyl]benzenesulfonamide;
4-[2-(phenylthiomethyl)-5-phenyl-4-oxazolyl]benzenesulfonamide;
4-[2-(phenoxymethyl)-5-phenyl-4-oxazolyl]benzenesulfonamide;
4-[2-((4-chlorophenoxy)methyl)-5-phenyl-4-oxazolyl]benzenesulfonamide;
4-[2-((3-chlorophenoxy)methyl)-5-phenyl-4-oxazolyl]benzenesulfonamide;
4-[2-((2-chlorophenoxy)methyl)-5-phenyl-4-oxazolyl]benzenesulfonamide;
4-[2-((4-fluorophenoxy)methyl)-5-phenyl-4-oxazolyl]benzenesulfonamide;
4-[2-((3-fluorophenoxy)methyl)-5-phenyl-4-oxazolyl]benzenesulfonamide;
4-[2-((2-fluorophenoxy) methyl)-5-phenyl-4-oxazolyl]benzenesulfonamide;
4-[2-((4-carboxyphenoxy)methyl)-5-phenyl-4-oxazolyl]benzenesulfonamide;
4-[2-((3-carboxyphenoxy)methyl)-5-phenyl-4-oxazolyl]benzenesulfonamide;
4-[2-((2-carboxyphenoxy)methyl)-5-phenyl-4-oxazolyl]benzenesulfonamide;
4-[2-(2-phenylethyl)-5-phenyl-4-oxazolyl]benzenesulfonamide;
4-[2-(3-phenylpropyl)-5-phenyl-4-oxazolyl]benzenesulfonamide;
[4-(4-aminosulfonylphenyl)-5-phenyl]-2-oxazoleacetic acid;
methyl [4-(4-aminosulfonylphenyl)-5-phenyl]-2-oxazoleacetate;
ethyl [4-(4-aminosulfonylphenyl)-5-phenyl]-2-oxazoleacetate;
[4-(4-aminosulfonylphenyl)-5-phenyl]-2-oxazolepropanoic acid;
methyl [4-(4-aminosulfonylphenyl)-5-phenyl]-2-oxazolepropanoate;
ethyl [4-(4-aminosulfonylphenyl)-5-phenyl]-2-oxazolepropanoate;
[4-(4-aminosulfonylphenyl)-5-phenyl]-2-oxazolebutanoic acid;
methyl [4-(4-aminosulfonylphenyl)-5-phenyl]-2-oxazolebutanoate;
ethyl [4-(4-aminosulfonylphenyl)-5-phenyl]-2-oxazolebutanoate;
4-[2-(2-quinolyloxymethyl)-5-phenyl-4-oxazolyl]benzenesulfonamide;
4-[2-benzyl-4-phenyl-5-oxazolyl]benzenesulfonamide;
4-[2-benzyl-4-(2-fluorophenyl)-5-oxazolyl]benzenesulfonamide;
4-[2-benzyl-4-(3-fluorophenyl)-5-oxazolyl]benzenesulfonamide;
4-[2-benzyl-4-(4-fluorophenyl)-5-oxazolyl]benzenesulfonamide;
4-[2-benzyl-4-(2,4-difluorophenyl)-5-oxazolyl]benzenesulfonamide;
4-[2-benzyl-4-(2,5-difluorophenyl)-5-oxazolyl]benzenesulfonamide;
4-[2-benzyl-4-(2,6-difluorophenyl)-5-oxazolyl]benzenesulfonamide;
4-[2-benzyl-4-(3,4-difluorophenyl)-5-oxazolyl]benzenesulfonamide;
4-[2-benzyl-4-(3,5-difluorophenyl)-5-oxazolyl]benzenesulfonamide;
4-[2-benzyl-4-(2-chlorophenyl)-5-oxazolyl]benzenesulfonamide;

4-[2-benzyl-4-(3-chlorophenyl)-5-oxazolyl]
benzenesulfonamide;
4-[2-benzyl-4-(4-chlorophenyl)-5-oxazolyl]
benzenesulfonamide;
4-[2-benzyl-4-(2,4-dichlorophenyl)-5-oxazolyl]
benzenesulfonamide;
4-[2-benzyl-4-(2,5-dichlorophenyl)-5-oxazolyl]
benzenesulfonamide;
4-[2-benzyl-4-(2,6-dichlorophenyl)-5-oxazolyl]
benzenesulfonamide;
4-[2-benzyl-4-(3,4-dichlorophenyl)-5-oxazolyl]
benzenesulfonamide;
4-[2-benzyl-4-(3,5-dichlorophenyl)-5-oxazolyl]
benzenesulfonamide;
4-[2-benzyl-4-(2-methoxyphenyl)-5-oxazolyl]
benzenesulfonamide;
4-[2-benzyl-4-(3-methoxyphenyl)-5-oxazolyl]
benzenesulfonamide;
4-[2-benzyl-4-(4-methoxyphenyl)-5-oxazolyl]
benzenesulfonamide;
4-[2-benzyl-4-(2,4-dimethoxyphenyl)-5-oxazolyl]
benzenesulfonamide;
4-[2-benzyl-4-(2,5-dimethoxyphenyl)-5-oxazolyl]
benzenesulfonamide;
4-[2-benzyl-4-(2,6-dimethoxyphenyl)-5-oxazolyl]
benzenesulfonamide;
4-[2-benzyl-4-(3,4-dimethoxyphenyl)-5-oxazolyl]
benzenesulfonamide;
4-[2-benzyl-4-(3,5-dimethoxyphetyl)-5-oxazolyl]
benzenesulfonamide;
4-[2-benzyl-4-(2-methylphenyl)-5-oxazolyl]
benzenesulfonamide;
4-[2-benzyl-4-(3-methylphenyl)-5-oxazolyl]
benzenesulfonamide;
4-[2-benzyl-4-(4-methylphenyl)-5-oxazolyl]
benzenesulfonamide;
4-[2-benzyl-4-(2,4-dimethylphenyl)-5-oxazolyl]
benzenesulfonamide;
4-[2-benzyl-4-(2,5-dimethylphenyl)-5-oxazolyl]
benzenesulfonamide;
4-[2-benzyl-4-(2,6-dimethylphenyl)-5-oxazolyl]
benzenesulfonamide;
4-[2-benzyl-4-(3,4-dimethylphenyl)-5-oxazolyl]
benzenesulfonamide;
4-[2-benzyl-4-(3,5-dimethylphenyl)-5-oxazolyl]
benzenesulfonamide;
4-[2-benzyl-4-(2-chloro-4-methylphenyl)-5-oxazolyl]
benzenesulfonamide;
4-[2-benzyl-4-(3-chloro-4-methylphenyl)-5-oxazolyl benzenesulfonamide;
4-[2-benzyl-4-(3-chloro-2-methylphenyl)-5-oxazolyl]
benzenesulfonamide;
4-[2-benzyl-4-(2-chloro-6-methylphenyl)-5-oxazolyl]
benzenesulfonamide;
4-[2-benzyl-4-(4-chloro-2-methylphenyl)-5-oxazolyl]
benzenesulfonamide;
4-[2-benzyl-4-(4-chloro-3-methylphenyl)-5-oxazolyl]
benzenesulfonamide;
4-(2-benzyl-4-(2-chloro-4-methoxyphenyl)-5-oxazolyl]
benzenesulfonamide;
4-[2-benzyl-4-(3-chloro-4-methoxyphenyl)-5-oxazolyl]
benzenesulfonamide;
4-[2-benzyl-4-(3-chloro-2-methoxyphenyl)-5-oxazolyl]
benzenesulfonamide;
4-[2-benzyl-4-(2-chloro-6-methoxyphenyl)-5-oxazolyl]
benzenesulfonamide;
4-[2-benzyl-4-(4-chloro-2-methoxyphenyl)-5-oxazolyl]
benzenesulfonamide;
4-[2-benzyl-4-(4-chloro-3-methoxyphenyl)-5-oxazolyl]
benzenesulfonamide;
4-[2-benzyl-4-(3,5-dichloro-4-methoxyphenyl)-5-oxazolyl]
benzenesulfonamide;
4-[2-benzyl-4-(2-fluoro-4-methylphenyl)-5-oxazolyl]
benzenesulfonamide;
4-[2-benzyl-4-(3-fluoro-4-methylphenyl)-5-oxazolyl]
benzenesulfonamide;
4-[2-benzyl-4-(3-fluoro-2-methylphenyl)-5-oxazolyl]
benzenesulfonamide;
4-[2-benzyl-4-(2-fluoro-6-methylphenyl)-5-oxazolyl]
benzenesulfonamide;
4-[2-benzyl-4-(4-fluoro-2-methylphenyl)-5-oxazolyl]
benzenesulfonamide;
4-[2-benzyl-4-(4-fluoro-3-methylphenyl)-5-oxazolyl]
benzenesulfonamide;
4-[2-benzyl-4-(2-fluoro-4-methoxyphenyl)-5-oxazolyl]
benzenesulfonamide;
4-[2-benzyl-4-(3-fluoro-4-methoxyphenyl)-5-oxazolyl]
benzenesulfonamide;
4-[2-benzyl-4-(3-fluoro-2-methoxyphenyl)-5-oxazolyl]
benzenesulfonamide;
4-[2-benzyl-4-(2-fluoro-6-methoxyphenyl)-5-oxazolyl]
benzenesulfonamide;
4-[2-benzyl-4-(4-fluoro-2-methoxyphenyl)-5-oxazolyl]
benzenesulfonamide;
4-[2-benzyl-4-(2-thienyl)-5-oxazolyl]benzenesulfonamide;
4-[2-benzyl-4-(5-chloro-2-thienyl)-5-oxazolyl]
benzenesulfonamide;
4-[2-benzyl-4-(cyclohexyl)-5-oxazolyl]
benzenesulfonamide;
4-[2-benzyl-4-(1-cyclohexenyl)-5-oxazolyl]
benzenesulfonamide;
4-[2-benzyl-4-(2-cyclohexenyl)-5-oxazolyl]
benzenesulfonamide;
4-[2-benzyl-4-(3-cyclohexenyl)-5-oxazolyl]
benzenesulfonamide;
2-benzyl-5-(4-methylsulfonylphenyl)-4-phenyloxazole;
2-benzyl-5-(4-methylsulfonylphenyl)-4-(2-fluorophenyl)
oxazole;
2-benzyl-5-(4-methylsulfonylphenyl)-4-(3-fluorophenyl)
oxazole;
2-benzyl-5-(4-methylsulfonylphenyl)-4-(2,4-difluorophenyl)oxazole;
2-benzyl-5-(4-methylsulfonylphenyl)-4-(2,5-difluorophenyl)oxazole;
2-benzyl-5-(4-methylsulfonylphenyl)-4-(2,6-difluorophenyl)oxazole;
2-benzyl-5-(4-methylsulfonylphenyl)-4-(3,4-difluorophenyl)oxazole;
2-benzyl-5-(4-methylsulfonylphenyl)-4-(3,5-difluorophenyl)oxazole;
2-benzyl-5-(4-methylsulfonylphenyl)-4-(2-chlorophenyl)-4-oxazolyl]benzenesulfonamide;
2-benzyl-5-(4-methylsulfonylphenyl)-4-(3-chlorophenyl)
oxazole;
2-benzyl-5-(4-methylsulfonylphenyl)-4-(4-chlorophenyl)-4-oxazolyl]benzenesulfonamide;
2-benzyl-5-(4-methylsulfonylphenyl)-4-(2,4-dichlorophenyl)oxazole;
2-benzyl-5-(4-methylsulfonylphenyl)-4-(2,5-dichlorophenyl)oxazole;
2-benzyl-5-(4-methylsulfonylphenyl)-4-(2,6-dichlorophenyl)oxazole;
2-benzyl-5-(4-methylsulfonylphenyl)-4-(3,4-dichlorophenyl)oxazole;
2-benzyl-5-(4-methylsulfonylphenyl)-4-(3,5-dichlorophenyl)oxazole;

2-benzyl-5-(4-methylsulfonylphenyl)-4-(2-methoxyphenyl)
oxazole;
2-benzyl-5-(4-methylsulfonylphenyl)-4-(3-methoxyphenyl)
oxazole;
2-benzyl-5-(4-methylsulfonylphenyl)-4-(4-methoxyphenyl)
oxazole;
2-benzyl-5-(4-methylsulfonylphenyl)-4-(2,4-dimethoxyphenyl)oxazole;
2-benzyl-5-(4-methylsulfonylphenyl)-4-(2,5-dimethoxyphenyl)oxazole;
2-benzyl-5-(4-methylsulfonylphenyl)-4-(2,6-dimethoxyphenyl)oxazole;
2-benzyl-5-(4-methylsulfonylphenyl)-4-(3,4-dimethoxyphenyl)oxazole;
2-benzyl-5-(4-methylsulfonylphenyl)-4-(3,5-dimethoxyphenyl)oxazole;
2-benzyl-5-(4-methylsulfonylphenyl)-4-(2-methylphenyl)
oxazole;
2-benzyl-5-(4-methylsulfonylphenyl)-4-(3-methylphenyl)
oxazole;
2-benzyl-5-(4-methylsulfonylphenyl)-4-(4-methylphenyl)
oxazole;
2-benzyl-5-(4-methylsulfonylphenyl)-4-(2,4-dimethylphenyl)oxazole;
2-benzyl-5-(4-methylsulfonylphenyl)-4-(2,5-dimethylphenyl)oxazole;
2-benzyl-5-(4-methylsulfonylphenyl)-4-(2,6-dimethylphenyl)oxazole;
2-benzyl-5-(4-methylsulfonylphenyl)-4-(3,4-dimethylphenyl)oxazole;
2-benzyl-5-(4-methylsulfonylphenyl)-4-(3,5-dimethylphenyl)oxazole;
2-benzyl-5-(4-methylsulfonylphenyl)-4-(2-chloro-4-methylphenyl)oxazole;
2-benzyl-5-(4-methylsulfonylphenyl)-4-(3-chloro-4-methylphenyl)oxazole;
2-benzyl-5-(4-methylsulfonylphenyl)-4-(3-chloro-2-methylphenyl)oxazole;
2-benzyl-5-(4-methylsulfonylphenyl)-4-(2-chloro-6-methylphenyl)oxazole;
2-benzyl-5-(4-methylsulfonylphenyl)-4-(4-chloro-2-methylphenyl)oxazole;
2-benzyl-5-(4-methylsulfonylphenyl)-4-(4-chloro-3-methylphenyl)oxazole;
2-benzyl-5-(4-methylsulfonylphenyl)-4-(2-chloro-4-methoxyphenyl)oxazole;
2-benzyl-5-(4-methylsulfonylphenyl)-4-(3-chloro-4-methoxyphenyl)oxazole;
2-benzyl-5-(4-methylsulfonylphenyl)-4-(3-chloro-2-methoxyphenyl)oxazole;
2-benzyl-5-(4-methylsulfonylphenyl)-4-(2-chloro-6-methoxyphenyl)oxazole;
2-benzyl-5-(4-methylsulfonylphenyl)-4-(4-chloro-2-methoxyphenyl)oxazole;
2-benzyl-5-(4-methylsulfonylphenyl)-4-(4-chloro-3-methoxyphenyl)oxazole;
2-benzyl-5-(4-methylsulfonylphenyl)-4-(3,5-dichloro-4-methoxyphenyl)oxazole;
2-benzyl-5-(4-methylsulfonylphenyl)-4-(2-fluoro-4-methylphenyl)oxazole;
2-benzyl-5-(4-methylsulfonylphenyl)-4-(3-fluoro-4-methylphenyl)oxazole;
2-benzyl-5-(4-methylsulfonylphenyl)-4-(3-fluoro-2-methylphenyl)oxazole;
2-benzyl-5-(4-methylsulfonylphenyl)-4-(2-fluoro-6-methylphenyl)oxazole;
2-benzyl-5-(4-methylsulfonylphenyl)-4-(4-fluoro-2-methylphenyl)oxazole;
2-benzyl-5-(4-methylsulfonylphenyl)-4-(4-fluoro-3-methylphenyl)oxazole;
2-benzyl-5-(4-methylsulfonylphenyl)-4-(2-fluoro-4-methoxyphenyl)oxazole;
2-benzyl-5-(4-methylsulfonylphenyl)-4-(3-fluoro-4-methoxyphenyl)oxazole;
2-benzyl-5-(4-methylsulfonylphenyl)-4-(3-fluoro-2-methoxyphenyl)oxazole;
2-benzyl-5-(4-methylsulfonylphenyl)-4-(2-fluoro-6-methoxyphenyl)oxazole;
2-benzyl-5-(4-methylsulfonylphenyl)-4-(4-fluoro-2-methoxyphenyl)oxazole;
2-benzyl-5-(4-methylsulfonylphenyl)-4-(2-thienyl)oxazole;
2-benzyl-5-(4-methylsulfonylphenyl)-4-(5-chloro-2-thienyl)oxazole;
2-benzyl-5-(4-methylsulfonylphenyl)-4-(cyclohexyl)
oxazole;
2-benzyl-5-(4-methylsulfonylphenyl)-4-(1-cyclohexenyl)
oxazole;
2-benzyl-5-(4-methylsulfonylphenyl)-4-(2-cyclohexenyl)
oxazole;
2-benzyl-5-(4-methylsulfonylphenyl)-4-(3-cyclohexenyl)
oxazole;
2-(ethyl)-5-(4-methylsulfonylphenyl)-4-phenyloxazole;
2-(trifluoromethyl)-5-(4-methylsulfonylphenyl)-4-phenyloxazole;
2-(difluoromethyl)-5-(4-methylsulfonylphenyl)-4-phenyloxazole;
2-(hydroxymethyl)-5-(4-methylsulfonylphenyl)-4-phenyloxazole;
[5-(4-methylsulfonylphenyl)-4-phenyl]-2-oxazolecarboxylic acid;
methyl [5-(4-methylsulfonylphenyl)-4-phenyl]-2-oxazolecarboxylate;
ethyl [5-(4-methylsulfonylphenyl)-4-phenyl]-2-oxazolecarboxylate;
2-(propyl)-5-(4-methylsulfonylphenyl)-4-phenyloxazole;
2-(benzyl)-5-(4-methylsulfonylphenyl)-4-phenyloxazole;
2-(phenylthiomethyl)-5-(4-methylsulfonylphenyl)-4-phenyloxazole;
2-(phenoxymethyl)-5-(4-methylsulfonylphenyl)-4-phenyloxazole;
2-((4-chlorophenoxy)methyl)-5-(4-methylsulfonylphenyl)-4-phenyloxazole;
2-((3-chlorophenoxy)methyl)-5-(4-methylsulfonylphenyl)-4-phenyloxazole;
2-((2-chlorophenoxy)methyl)-5-(4-methylsulfonylphenyl)-4-phenyloxazole;
2-((4-fluorophenoxy)methyl)-5-(4-methylsulfonylphenyl)-4-phenyloxazole;
2-((3-fluorophenoxy)methyl)-5-(4-methylsulfonylphenyl)-4-phenyloxazole;
2-((2-fluorophenoxy)methyl)-5-(4-methylsulfonylphenyl)-4-phenyloxazole;
2-((4-carboxyphenoxy)methyl)-5-(4-methylsulfonylphenyl)-4-phenyloxazole;
2-((3-carboxyphenoxy)methyl)-5-(4-methylsulfonylphenyl)-4-phenyloxazole;
2-((2-carboxyphenoxy)methyl)-5-(4-methylsulfonylphenyl)-4-phenyloxazole;
2-(2-phenethyl)-5-(4-methylsulfonylphenyl)-4-phenyloxazole;
2-(3-phenylpropyl)-5-(4-methylsulfonylphenyl)-4-phenyloxazole;
[5-(4-methylsulfonylphenyl)-4-phenyl]-2-oxazoleacetic
acid;
ethyl [5-(4-methylsulfonylphenyl)-4-phenyl]-2-oxazoleacetate;

methyl [5-(4-methylsulfonylphenyl)-4-phenyl]-2-oxazoleacetate;
[5-(4-methylsulfonylphenyl)-4-phenyl]-2-oxazolepropanoic acid;
ethyl [5-(4-methylsulfonylphenyl)-4-phenyl]-2-oxazolepropanoate;
methyl [5-(4-methylsulfonylphenyl)-4-phenyl]-2-oxazolepropanoate;
[5-(4-methylsulfonylphenyl)-4-phenyl]-2-oxazolebutanoic acid;
ethyl [5-(4-methylsulfonylphenyl)-4-phenyl]-2-oxazolebutanoate;
methyl [5-(4-methylsulfonylphenyl)-4-phenyl]-2-oxazolebutanoate;
2-(2-quinolyloxymethyl)-5-(4-methylsulfonylphenyl)-4-phenyloxazole;
4-[2-(ethyl)-4-phenyl-5-oxazolyl]benzenesulfonamide;
4-[2-(trifluoromethyl)-4-phenyl-5-oxazolyl]benzenesulfonamide;
4-[2-(difluoromethyl)-4-phenyl-5-oxazolyl]benzenesulfonamide;
4-[2-(hydroxymethyl)-4-phenyl-5-oxazolyl]benzenesulfonamide;
[5-(4-aminosulfonylphenyl)-4-phenyl]-2-oxazolecarboxylic acid;
methyl [5-(4-aminosulfonylphenyl)-4-phenyl]-2-oxazolecarboxylate;
ethyl [5-(4-aminosulfonylphenyl)-4-phenyl]-2-oxazolecarboxylate;
4-[2-(propyl)-4-phenyl-5-oxazolyl]benzenesulfonamide;
4-[2-(benzyl)-4-phenyl-5-oxazolyl]benzenesulfonamide;
4-[2-(phenylthiomethyl)-4-phenyl-5-oxazolyl]benzenesulfonamide;
4-[2-(phenoxymethyl)-4-phenyl-5-oxazolyl]benzenesulfonamide;
4-[2-((4-chlorophenoxy)methyl)-4-phenyl-5-oxazolyl]benzenesulfonamide;
4-[2-((3-chlorophenoxy)methyl)-4-phenyl-5-oxazolyl]benzenesulfonamide;
4-[2-((2-chlorophenoxy)methyl)-4-phenyl-5-oxazolyl]benzenesulfonamide;
4-[2-((4-fluorophenoxy)methyl)-4-phenyl-5-oxazolyl]benzenesulfonamide;
4-[2-((3-fluorophenoxy)methyl)-4-phenyl-5-oxazolyl]benzenesulfonamide;
4-[2-((2-fluorophenoxy)methyl)-4-phenyl-5-oxazolyl]benzenesulfonamide;
4-[2-((4-carboxyphenoxy)methyl)-4-phenyl-5-oxazolyl]benzenesulfonamide;
4-[2-((3-carboxyphenoxy)methyl)-4-phenyl-5-oxazolyl]benzenesulfonamide;
4-[2-((2-carboxyphenoxy)methyl)-4-phenyl-5-oxazolyl]benzenesulfonamide;
4-[2-(2-phenethyl)-4-phenyl-5-oxazolyl]benzenesulfonamide;
4-[2-(3-phenylpropyl)-4-phenyl-5-oxazolyl]benzenesulfonamide;
[5-(4-aminosulfonylphenyl)-4-phenyl]-2-oxazoleacetic acid;
methyl [5-(4-aminosulfonylphenyl)-4-phenyl]-2-oxazoleacetate;
ethyl [5-(4-aminosulfonylphenyl)-4-phenyl]-2-oxazoleacetate;
[5-(4-aminosulfonylphenyl)-4-phenyl]-2-oxazolepropanoic acid;
methyl [5-(4-aminosulfonylphenyl)-4-phenyl]-2-oxazolepropanoate;
ethyl [5-(4-aminosulfonylphenyl)-4-phenyl]-2-oxazolepropanoate;
[5-(4-aminosulfonylphenyl)-4-phenyl]-2-oxazolebutanoic acid;
methyl [5-(4-aminosulfonylphenyl)-4-phenyl]-2-oxazolebutanoate;
ethyl [5-(4-aminosulfonylphenyl)-4-phenyl]-2-oxazolebutanoate;
4-[2-(2-quinolyloxymethyl)-4-phenyl-5-oxazolyl]benzenesulfonamide;
5-(4-fluorophenyl)-2-methyl-4-[4-(methylsulfonyl)phenyl]oxazole;
3-[5-(4-fluorophenyl)-4-[4-(methylsulfonyl)phenyl]]-2-oxazolepropanoic acid;
methyl 3-[5-(4-fluorophenyl)-4-[4-(methylsulfonyl)phenyl]]-2-oxazolepropanoate;
4-(4-fluorophenyl)-2-(2-phenylethyl)-5-(4-(methylsulfonyl)phenyl)oxazole;
4-(4-fluorophenyl)-2-methyl-5-[4-(methylsulfonyl)phenyl]oxazole;
4-(4-fluorophenyl)-5-[4-(methylsulfonyl)phenyl]-2-phenyloxazole;
2-benzyl-4-(4-fluorophenyl)-5-(4-(methylsulfonyl)phenyl)oxazole;
4-(4-fluorophenyl)-5-[4-methylsulfonylphenyl]-2-(3-phenylpropyl)oxazole;
4-(4-fluorophenyl)-5-[4-methylsulfonylphenyl]-2-propyloxazole;
2-(tert-butyl)-4-(4-fluorophenyl)-5-[4-methylsulfonylphenyl]oxazole;
4-(4-fluorophenyl)-2-[(4-methoxyphenyl)methyl]-5-[4-methylsulfonylphenyl]oxazole;
4-(4-fluorophenyl)-2-[(3-methoxyphenyl)methyl]-5-[4-methylsulfonylphenyl]oxazole;
2-(diphenylmethyl)-4-(4-fluorophenyl)-5-[4-methylsulfonylphenyl]oxazole;
2-[4-(4-fluorophenyl)-5-[4-methylsulfonylphenyl]]-2-oxazoleacetic acid;
ethyl 2-[4-(4-fluorophenyl)-5-[4-methylsulfonylphenyl]]-2-oxazoleacetate;
3-[4-(4-fluorophenyl)-5-[4-methylsulfonylphenyl]]-2-oxazolepropanoic acid;
methyl 3-[4-(4-fluorophenyl)-5-[4-methylsulfonylphenyl]]-2-oxazolepropanoate;
4-[4-(4-fluorophenyl)-5-[4-methylsulfonylphenyl]]-2-oxazolebutanoic acid;
methyl 4-[4-(4-fluorophenyl)-5-[4-methylsulfonyl phenyl]]-2-oxazolebutanoate;
3-[4-(4-fluorophenyl)-5-[4-methylsulfonylphenyl]]-2-oxazolepropanamide;
4-(4-fluorophenyl)-2-(cyclohexylethyl)-5-[4-(methylsulfonyl)phenyl]oxazole;
4-(4-fluorophenyl)-2-(3-fluorophenoxymethyl)-5-[4-(methylsulfonyl)phenyl]oxazole;
4-(4-fluorophenyl)-2-(3-chlorophenoxymethyl)-5-[4-(methylsulfonyl)phenyl]oxazole;
4-(4-fluorophenyl)-2-(pyridyloxymethyl)-5-[4-(methylsulfonyl)phenyl]oxazole;
4-(4-fluorophenyl)-5-[4-(methylsulfonyl)phenyl]-2-phenoxymethyloxazole;
4-(4-fluorophenyl)-2-(2-hydroxyethyl)-5-[4-(methylsulfonyl)phenyl]oxazole;
4-(4-fluorophenyl)-2-(hydroxymethyl)-5-[4-(methylsulfonyl)phenyl]oxazole;
4-(cyclohexyl)-2-phenyl-5-[4-(methylsulfonyl)phenyl]oxazole;
4-(4-fluorophenyl)-2-benzyloxymethyl-5-[4-(methylsulfonyl)phenyl]oxazole;

4-(4-fluorophenyl)-2-cyclohexyl-5-[4-(methylsulfonyl) phenyl]oxazole;

5-(4-fluorophenyl)-2-phenyl-4-[4-(methylsulfonyl)phenyl] oxazole;

[5-(3,4-dichlorophenyl)-2-trifluoromethyl-4-oxazolyl] benzenesulfonamide;

4-[4-(3-aminosulfonyl-5-fluoro-4-methoxyphenyl)-2-trifluoromethyl-5-oxazolyl]benzenesulfonamide;

4-(3-fluoro-4-methoxyphenyl)-5-(4-methylsulfonylphenyl)-2-trifluoromethyloxazole;

4-[4-(4-bromophenyl)-2-methyl-5-oxazolyl] benzenesulfonamide;

5-fluoro-4-methoxy-3-[5-phenyl-2-trifluoromethyl-4-oxazolyl]benzenesulfonamide;

4-[4-(3-fluoro-4-methoxyphenyl)-2-trifluoromethyl-5-oxazolyl]benzenesulfonamide;

ethyl 4-[[5-(4-aminosulfonylphenyl)-4-phenyl-2-oxazolyl] oxy]benzoate; and

4-[5-(3-chloro-4-fluorophenyl)-2-trifluoromethyl-4-oxazolyl]benzenesulfonamide.

Where the term "alkyl" is used, either alone or within other terms such as "haloalkyl", "alkoxyalkyl" and "hydroxyalkyl", embraces linear or branched radicals having one to about twenty carbon atoms or, preferably, one to about twelve carbon atoms. More preferred alkyl radicals are "lower alkyl" radicals having one to about ten carbon atoms. Most preferred are lower alkyl radicals having one to about six carbon atoms. Examples of such radicals include methyl, ethyl, n-propyl, isopropyl, n-butyl, isobutyl, sec-butyl, tert-butyl, pentyl, iso-amyl, hexyl and the like. The term "alkenyl" embraces linear or branched radicals having at least one carbon-carbon double bond of two to about twenty carbon atoms or, preferably, two to about twelve carbon atoms, provided that the double bond does not occur at the point of attachment of the radical. More preferred alkenyl radicals are "lower alkenyl" radicals having two to about six carbon atoms. Examples of such radicals include ethenyl, n-propenyl, butenyl, and the like. The term "alkynyl" embraces linear or branched radicals having two to about twenty carbon atoms or, preferably, two to about twelve carbon atoms, and containing a carbon-carbon triple bond. The more preferred "lower alkynyl" are radicals having two to ten carbons. Examples of such radicals include ethynyl, 1- or 2-propynyl, 1-, 2- or 3-butynyl and the like and isomers thereof. The term "hydrido" denotes a single hydrogen atom (H). This hydrido radical may be attached, for example, to an oxygen atom to form a hydroxyl radical, to a sulfur atom to form a mercapto radical, or two hydrido radicals may be attached to a carbon atom to form a methylene ($-CH_2-$) radical. The term "halo" means halogens such as fluorine, chlorine, bromine or iodine. The term "haloalkyl" embraces radicals wherein any one or more of the alkyl carbon atoms is substituted with halo as defined above. Specifically embraced are monohaloalkyl, dihaloalkyl and polyhaloalkyl radicals. A monohaloalkyl radical, for one example, may have either an iodo, bromo, chloro or fluoro atom within the radical. Dihalo and polyhaloalkyl radicals may have two or more of the same halo atoms or a combination of different halo radicals. "Lower haloalkyl" embraces radicals having 1–6 carbon atoms. Examples of haloalkyl radicals include fluoromethyl, difluoromethyl, trifluoromethyl, chloromethyl, dichloromethyl, trichloromethyl, trichloromethyl, pentafluoroethyl, heptafluoropropyl, difluorochloromethyl, dichlorofluoromethyl, difluoroethyl, difluoropropyl, dichloroethyl and dichloropropyl. The term "hydroxyalkyl" embraces linear or branched alkyl radicals having one to about ten carbon atoms any one of which may be substituted with one or more hydroxyl radicals. More preferred hydroxyalkyl radicals are "lower hydroxyalkyl" radicals having one to six carbon atoms and one or more hydroxyl radicals. Examples of such radicals include hydroxymethyl, hydroxyethyl, hydroxypropyl, hydroxybutyl and hydroxyhexyl. The term "hydroxyalkenyl" embraces linear or branched alkenyl radicals having two to about ten carbon atoms any one of which may be substituted with one or more hydroxyl radicals. The term "hydroxyalkynyl" embraces linear or branched alkynyl radicals having two to about ten carbon atoms any one of which may be substituted with one or more hydroxyl radicals. The terms "alkoxy" and "alkoxyalkyl" embrace linear or branched oxy-containing radicals each having alkyl portions of one to about twelve carbon atoms. More preferred alkoxy radicals are "lower alkoxy" radicals having one to six carbon atoms. Examples of such radicals include methoxy, ethoxy, propoxy, butoxy and tert-butoxy. The term "alkoxyalkyl" embraces alkyl radicals having one or more alkoxy radicals attached to the alkyl radical, that is, to form monoalkoxyalkyl and dialkoxyalkyl radicals. The "alkoxy" or "alkoxyalkyl" radicals may be further substituted with one or more halo atoms, such as fluoro, chloro or bromo, to provide haloalkoxy or haloalkoxyalkyl radicals. The term "aryl" embraces aromatic radicals such as phenyl, naphthyl and biphenyl. Preferred aryl radicals are those consisting of one, two, or three benzene rings. Aryl moieties may also be substituted at a substitutable position with one or more substituents selected independently from alkyl, alkoxyalkyl, alkylaminoalkyl, carboxyalkyl, alkoxycarbonylalkyl, aminocarbonylalkyl, alkoxy, amino, halo, nitro, alkylamino, alkylcarbonylamino, alkylsulfonyl, arylsulfonyl, acyl, cyano, carboxy, aminocarbonyl, alkoxycarbonyl and alkylthio. The terms "heterocycle" or "heterocyclic" embrace saturated, partially saturated and unsaturated heteroatom-containing ring-shaped radicals, where the heteroatoms may be selected from nitrogen, sulfur and oxygen. Examples of saturated heterocyclic radicals include saturated 5 to 7-membered heteromonocyclic group containing 1 to 4 nitrogen atoms [e.g. pyrrolidinyl, imidazolidinyl, piperidinyl, piperazinyl, tropanyl, homotropanyl, etc.]; saturated 5 to 7-membered heteromonocyclic group containing 1 to 2 oxygen atoms and 1 to 3 nitrogen atoms [e.g. morpholinyl, etc.]; saturated 5 to 7-membered heteromonocyclic group containing 1 to 2 sulfur atoms and 1 to 3 nitrogen atoms [e.g., thiazolidinyl, etc.]. Examples of partially saturated heterocyclic radicals include dihydrothiophene, dihydropyran, oxazolinyl, dihydrofuran and dihydrothiazole. Examples of unsaturated heterocyclic radicals, also termed "heteroaryl" radicals include unsaturated 5 to 7 membered heteromonocyclic group containing 1 to 4 nitrogen atoms, for example, pyrrolyl, pyrrolinyl, imidazolyl, pyrazolyl, pyridyl, pyrimidyl, azepinyl, pyrazinyl, pyridazinyl, triazolyl [e.g., 4H-1,2,4-triazolyl, 1H-1,2,3-triazolyl, 2H-1,2,3-triazolyl, etc.] tetrazolyl [e.g. 1H-tetrazolyl, 2H-tetrazolyl, etc.], etc.; unsaturated condensed heterocyclic group containing 1 to 5 nitrogen atoms, for example, indolyl, isoindolyl, indolizinyl, benzimidazolyl, quinolyl, isoquinolyl, indazolyl, benzotriazolyl, tetrazolopyridazinyl [e.g., tetrazolo[1,5-b] pyridazinyl, etc.], etc.; unsaturated 3 to 6-membered heteromonocyclic group containing an oxygen atom, for example, pyranyl, furyl, etc.; unsaturated 5 to 7-membered heteromonocyclic group containing a sulfur atom, for example, thienyl, etc.; unsaturated 5 to 7-membered heteromonocyclic group containing 1 to 2 oxygen atoms and 1 to 3 nitrogen atoms, for example, oxazolyl, isoxazolyl, oxadiazolyl [e.g., 1,2,4-oxadiazolyl, 1,3,4-oxadiazolyl, 1,2,5- oxadiazolyl, etc.] etc.; unsaturated condensed heterocyclic group containing 1 to 2 oxygen atoms and 1 to 3 nitrogen atoms [e.g. benzoxazolyl, benzoxadiazolyl, etc.]; unsaturated 5 to 7-membered heteromonocyclic group containing 1 to 2 sulfur atoms and 1 to 3 nitrogen atoms, for example, thiazolyl, thiadiazolyl [e.g., 1,2,4-thiadiazolyl, 1,3,4-thiadiazolyl, 1,2,5-thiadiazolyl, etc.] etc.; unsaturated condensed heterocyclic group containing 1 to 2 sulfur atoms and 1 to 3 nitrogen atoms [e.g., benzothiazolyl, benzothiadiazolyl, etc.] and the like. The term also embraces radicals where heterocyclic radicals are fused with aryl radicals. Examples of such fused bicyclic radicals include benzofuryl, benzothienyl, and the like. The heterocyclo moieties may also be substituted at a substitutable position with one or more substituents selected independently from alkyl, alkoxyalkyl, alkylaminoalkyl, carboxyalkyl, alkoxycarbonylalkyl, aminocarbonylalkyl, alkoxy, amino, halo, nitro, alkylamino, alkylcarbonylamino, alkylsulfonyl, arylsulfonyl, acyl, cyano, carboxy, aminocarbonyl, alkoxycarbonyl and alkylthio. The term "aralkyl" embraces aryl-substituted alkyl radicals. Preferable aralkyl radicals are "lower aralkyl" radicals having aryl radicals attached to alkyl radicals having one to six carbon atoms. Examples of such radicals include benzyl, diphenylmethyl, triphenylmethyl, phenylethyl and diphenylethyl. The terms benzyl and phenylmethyl are interchangeable. The term "aryloxy" embrace oxy-containing aryl radicals attached through an oxygen atom to other radicals. More preferred aryloxy radicals are "lower aryloxy" radicals having a phenyl radical. An example of such radicals is phenoxy. The term "aryloxyalkyl" embraces alkyl radicals having one or more aryloxy radicals attached to the alkyl radical, that is, to form monoaryloxyalkyl and diaryloxyalkyl radicals. The "aryloxy" or "aryloxyalkyl" radicals may be further substituted to provide haloaryloxyalkyl radicals alkylaryloxy radicals, and the like. Examples of such radicals include chlorophenoxy and methylphenoxy. The term "aralkyloxy" embrace oxy-containing aralkyl radicals attached through an oxygen atom to other radicals. The "aralkoxy" radicals may be further substituted on the aryl ring portion of the radical as described above. The term "aralkyloxyalkyl" embraces alkyl radicals having one or more aralkyloxy radicals attached to the alkyl radical, that is, to form monoaralkyloxyalkyl and diaralkyloxyalkyl radicals. The "aralkyloxy" or "aralkyloxyalkyl" radicals may be further substituted on the aryl ring portion of the radical. The term "heteroaryloxyalkyl" embraces alkyl radicals having one or more heteroaryloxy radicals attached to the alkyl radical, that is, to form monoheteroaryloxyalkyl and diheteroaryloxyalkyl radicals. The "heteroaryloxy" radicals may be further substituted on the heteroaryl ring portion of the radical. The term "arylthio" embraces radicals containing an aryl radical, as described above, attached to a divalent sulfur atom, such as a phenylthio radical. The term "arylthioalkyl" embraces alkyl radicals substituted with one or more arylthio radicals, as described above. The term "cycloalkyl" embraces radicals having three to ten carbon atoms. More preferred cycloalkyl radicals are "lower cycloalkyl" radicals having three to seven carbon atoms. Examples include radicals such as cyclopropyl, cyclobutyl, cyclopentyl, cyclohexyl and cycloheptyl. The term "cycloalkylalkyl" embraces alkyl radicals substituted with cycloalkyl radicals having three to ten carbon atoms, such as cyclopropylmethyl, cyclobutylmethyl, cyclopentylmethyl, cyclohexylmethyl, cyclohexylethyl, cyclohexylpropyl and cycloheptylmethyl. The term "cycloalkenyl" embraces unsaturated radicals having three to ten carbon atoms, such as cylopropenyl, cyclobutenyl, cyclopentenyl, cyclohexenyl and cycloheptenyl. The term "sulfonyl", whether used alone or linked to other terms such as alkylsulfonyl, denotes respectively divalent radicals —$SO_2$—. "Alkylsulfonyl" embraces alkyl radicals attached to a sulfonyl radical, where alkyl is defined as above. The "alkylsulfonyl" radicals may be further substituted with one or more halo atoms, such as fluoro, chloro or bromo, to provide haloalkylsulfonyl radicals. The term "alkylsulfinyl" embraces alkyl radicals attached to a sulfinyl (—S(O)—) radical, where alkyl is defined as above. More preferred alkylsulfinyl radicals are "lower alkylsulfinyl" radicals having one to six carbon atoms. Examples of such lower alkylsulfinyl radicals include methylsulfinyl, ethylsulfinyl, butylsulfinyl and hexylsulfinyl. The term "alkylthio" embraces alkyl radicals attached to a divalent sulfur radical, where alkyl is defined as above. More preferred alkylthio radicals are "lower alkylthio" radicals having alkyl radicals of one to six carbon atoms. Examples of such lower alkylthio radicals are methylthio, ethylthio, propylthio, butylthio and hexylthio. The terms "sulfamyl", "aminosulfonyl" and "sulfonamidyl" denote a sulfonyl radical substituted with an amine radical, forming a sulfonamide (—$SO_2NH_2$). The terms "carboxy" or "carboxyl", whether used alone or with other terms, such as "carboxyalkyl", denotes —$CO_2H$. The term "carboxyalkyl" embrace radicals having a carboxy radical as defined above, attached to an alkyl radical, which may be substituted, such as with halo radicals, or unsubstituted. Examples of such radicals include formyl, acetyl, propionyl, butyryl, isobutyryl, valeryl, isovaleryl, pivaloyl, hexanoyl, difluoroacetyl, trifluoroacetyl or the like, in which the preferable one is formyl, acetyl, propionyl or trifluoroacetyl. The term "carboxyalkylthio" embraces carboxyalkyl radicals as defined above, connected to a divalent sulfur atom. The term "alkoxycarbonyl" means a radical containing an alkoxy radical, as defined above, attached via an oxygen atom to a "carbonyl" (—C=O) radical. Examples of such "alkoxycarbonyl" ester radicals include substituted or unsubstituted methoxycarbonyl, ethoxycarbonyl, propoxycarbonyl, butoxycarbonyl and hexyloxycarbonyl. The term "alkoxycarbonylalkyl" embraces alkyl radicals having one or more alkoxycarbonyl radicals attached to the alkyl radical. The term "aminocarbonyl" embraces radicals having an amino radical radicals attached to a carbonyl radical forming —C(O)$NH_2$. The term "aminocarbonylalkyl" embraces alkyl radicals having one or more aminocarbonyl radicals attached to the alkyl radical. The term "alkylaminocarbonylalkyl" embraces alkyl radicals having aminocarbonyl radicals substituted with one or two alkyl radicals. Examples of such include N-alkylaminocarbonylalkyl and N,N-dialkylaminocarbonylalkyl radicals such as N-methylaminocarbonylmethyl and N,N-dimethylaminocarbonylmethyl. The term "alkylamino" denotes amino groups which have been substituted with one or two alkyl radicals. More preferred alkylamino radicals are "lower alkylamino" having alkyl radicals of one to six carbon atoms attached to the nitrogen atom of an amine. Suitable "lower alkylamino" may be mono or dialkylamino such as N-methylamino, N-ethylamino, N,N-dimethylamino, N,N-diethylamino or the like.

The present invention comprises a pharmaceutical composition for the treatment of inflammation and inflammation-associated disorders, such as arthritis, comprising a therapeutically-effective amount of a compound of Formula I in association with at least one pharmaceutically-acceptable carrier, adjuvant or diluent.

The present invention also comprises a therapeutic method of treating inflammation or inflammation-associated disorders in a subject, the method comprising administering to a subject having such inflammation or disorder a therapeutically-effective amount of a compound of Formula I.

Also included in the family of compounds of Formula I are the pharmaceutically-acceptable salts thereof. The term "pharmaceutically-acceptable salts" embraces salts commonly used to form alkali metal salts and to form addition salts of free acids or free bases. The nature of the salt is not critical, provided that it is pharmaceutically-acceptable. Suitable pharmaceutically-acceptable acid addition salts of compounds of Formula I may be prepared from an inorganic acid or from an organic acid. Examples of such inorganic acids are hydrochloric, hydrobromic, hydroiodic, nitric, carbonic, sulfuric and phosphoric acid. Appropriate organic acids may be selected from aliphatic, cycloaliphatic, aromatic, araliphatic, heterocyclic, carboxylic and sulfonic classes of organic acids, example of which are formic, acetic, propionic, succinic, glycolic, gluconic, lactic, malic, tartaric, citric, ascorbic, glucuronic, maleic, fumaric, pyruvic, aspartic, glutamic, benzoic, anthranilic, mesylic, salicylic, p-hydroxybenzoic, phenylacetic, mandelic, embonic (pamoic), methanesulfonic, ethylsulfonic, benzenesulfonic, pantothenic, toluenesulfonic, 2-hydroxyethanesulfonic, sulfanilic, stearic, cyclohexylaminosulfonic, algenic, β-hydroxybutyric, salicylic, galactaric and galacturonic acid. Suitable pharmaceutically-acceptable base addition salts of compounds of Formula I include metallic salts made from aluminum, calcium, lithium, magnesium, potassium, sodium and zinc or organic salts made from N,N'-dibenzylethylenediamine, choline, chloroprocaine, diethanolamine, ethylenediamine, meglumine (N-methylglucamine) and procaine. All of these salts may be prepared by conventional means from the corresponding compound of Formula I by reacting, for example, the appropriate acid or base with the compound of Formula I.

The compounds of the present invention may contain prodrugs of compounds of the current invention. The term "prodrug" embraces compounds which are metabolized in vivo into compounds of the invention.

The compounds of the present invention may contain asymmetric carbon atoms, and, therefore, the instant invention may also include the individual diastereomers and enantiomers, which may be prepared or isolated by methods known to those skilled in the art.

In other words, any resulting racemate can be resolved into the optical antipodes by known methods, for example, by separation of the diastereomeric salts thereof, with an optically active acid, and liberating the optically active amine compound by treatment with a base. Racemic compounds of the present invention can thus be resolved into their optical antipodes e.g., by fractional crystallization of d- or l-(tartrates, mandelates, or camphorsulfonate) salts.

Additional methods for resolving optical isomers, known to those skilled in the art may be used, for example, those discussed by J. Jaques et al in *Enantiomers, Racemates, and Resolutions*, John Wiley and Sons, New York (1981).

Compounds of the present invention also are meant to include, where possible, hydrated species.

GENERAL SYNTHETIC PROCEDURES

The compounds of the invention can be synthesized according to the following procedures of Schemes I–X, wherein the R-R$^4$ substituents are as defined for Formula I, above, except where further noted.

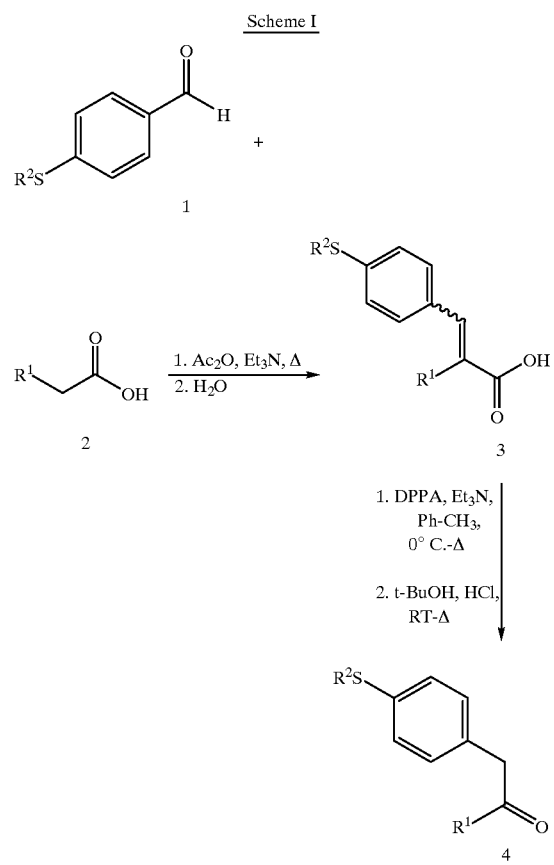

Synthetic Scheme I shows the four step procedure which can be used to prepare the substituted ketone compounds 4 from the substituted benzaldehyde 1 and acid 2, where R$^2$ is alkyl. In step one, benzaldehyde 1 and substituted acetic acid 2 are first heated in acetic anhydride and triethylamine via a Perkin condensation. In step two, hydrolysis produces the corresponding 2,3-disubstituted acrylic acids 3. In step three, the acrylic acids 3 are reacted with diphenylphosphorylazide (DPPA) and triethylamine in toluene at 0° C. and then warmed to room temperature to form acylazides. In step four, the crude acylazides are heated to form an isocyanate via a Curtius rearrangement. The isocyanate is trapped as the N-t-butyloxycarbonyl enamine derivative via the addition of tert-butanol. Acidic hydrolysis, such as by using concentrated HCl, provides the substituted ketone 4 intermediates.

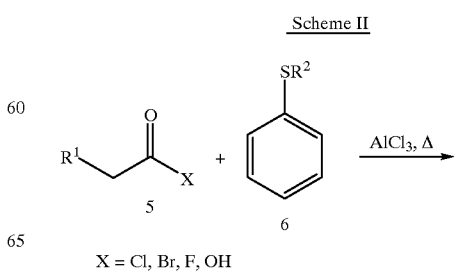

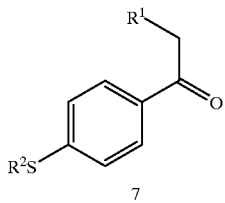

Synthetic Scheme II shows an alternative approach which can be used to prepare substituted ketone intermediates 7, isomers of 4 where $R^2$ is alkyl, via the use of Friedel-Crafts acylation. An acylating agent 5, such as an acid chloride, is treated with aluminum chloride in an inert solvent, such as methylene chloride, chloroform, nitrobenzene, dichlorobenzene or chlorobenzene, and reacted with alkylthiobenzene 6 to form ketone 7.

Other synthetic approaches are possible to form the desired ketones. These alternatives include reacting appropriate Grignard or lithium reagents with substituted acetic acids or corresponding esters.

5-(4-alkylsulfonylphenyl) oxazoles 12 of Formula I from ketone 4 (prepared in Scheme I). Preparation of the silyl enol ether 8 (where TBSCl is tert-butyl-dimethylsilyl chloride) is followed by oxidation, such as with m-chloroperoxybenzoic acid MCPBA), to give the appropriate silylated benzoin 9. Desilylation of this silylated benzoin 9 is achieved using aqueous acid, such as trifluoroacetic acid, to give the desired benzoin 10. Reaction of the benzoin 10 with the appropriate acid chloride in the presence of base, such as pyridine, gives the benzoin esters 11 which may be converted to the antiinflammatory oxazoles 12 of the present invention upon treatment with ammonium acetate in acetic acid at reflux.

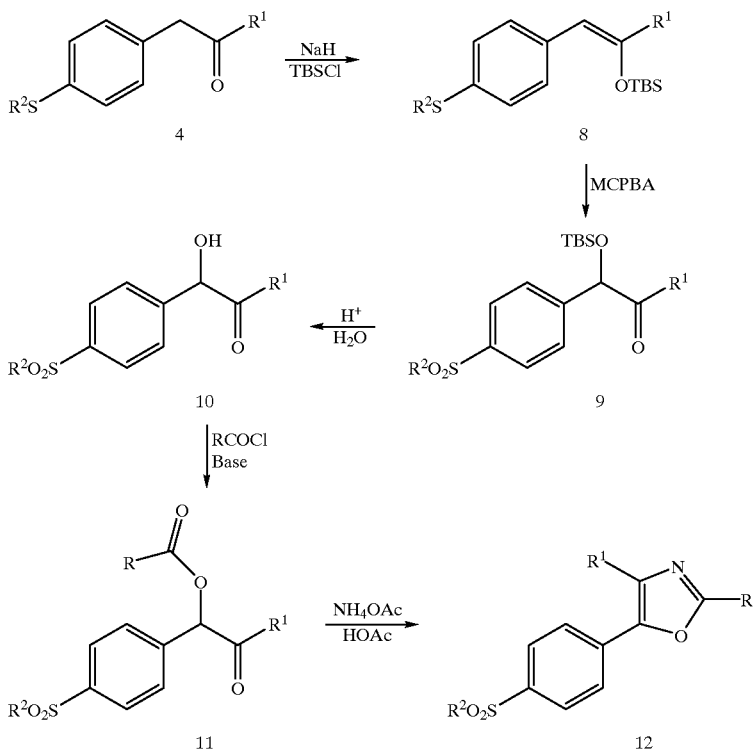

Scheme III shows the five step synthesis, as described in U.S. Pat. No. 3,647,858, which can be used to prepare the Scheme IV

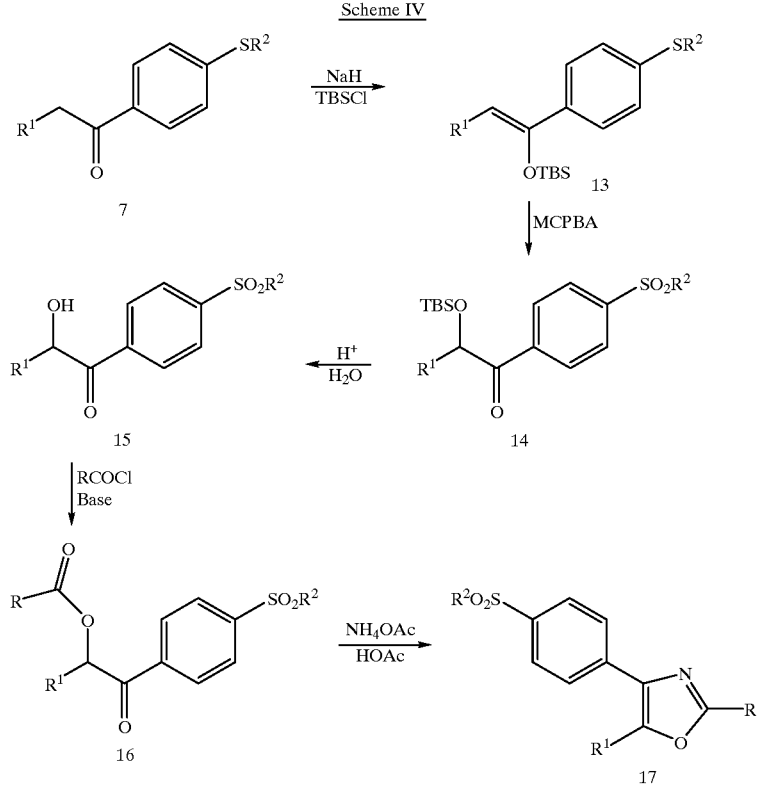

Scheme IV shows the five step synthesis, similar to that described above in Scheme III, which can be used to prepare the 4-(4-alkylsulfonylphenyl) oxazoles 17 of Formula I from ketone 7 (prepared in Scheme II). Preparation of the silyl enol ether 13 is followed by oxidation, such as with m-chloroperbenzoic acid, to give the appropriate silylated benzoin 14. Desilylation of this silylated benzoin 14 is achieved using aqueous acid, such as trifluoroacetic acid to give the desired benzoin 15. Reaction of the benzoin 15 with the appropriate acid chloride in the presence of base, such as pyridine, gives the benzoin esters 16 which may be converted to the antiinflammatory oxazoles 17 of the present invention upon treatment with ammonium acetate in acetic acid at reflux.

Scheme V

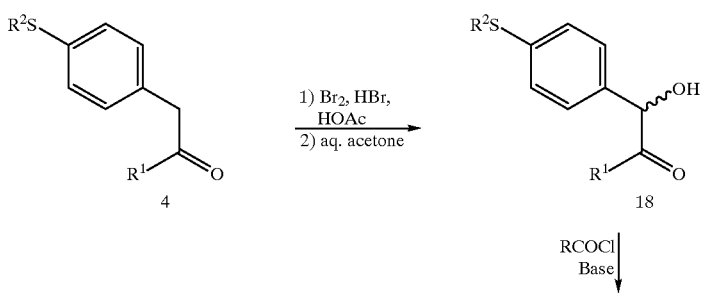

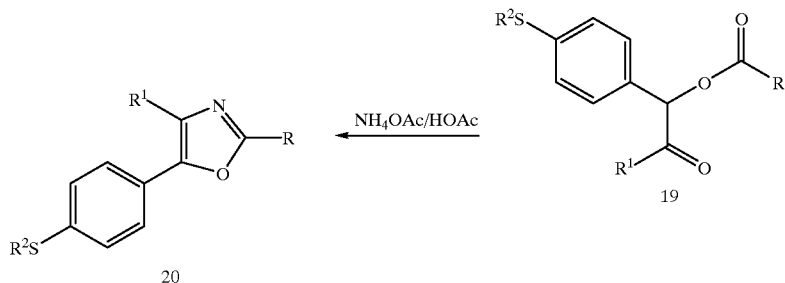

Scheme V shows the four step synthesis which can be used to prepare oxazoles 20 from ketones 4 (prepared in Synthetic Scheme I). In step one, ketones 4 are readily brominated via the addition of bromine in acetic acid to form the 2-bromoethanone intermediates. In step two, reaction of the bromoethanone with aqueous acetone yields the benzoin 18. In step three, reaction of the benzoin 18 with the appropriate acid chloride in the presence of base, such as pyridine, gives the benzoin esters 19. In step four, benzoin esters 19 are converted to the oxazoles 20 upon treatment with ammonium acetate in acetic acid at reflux.

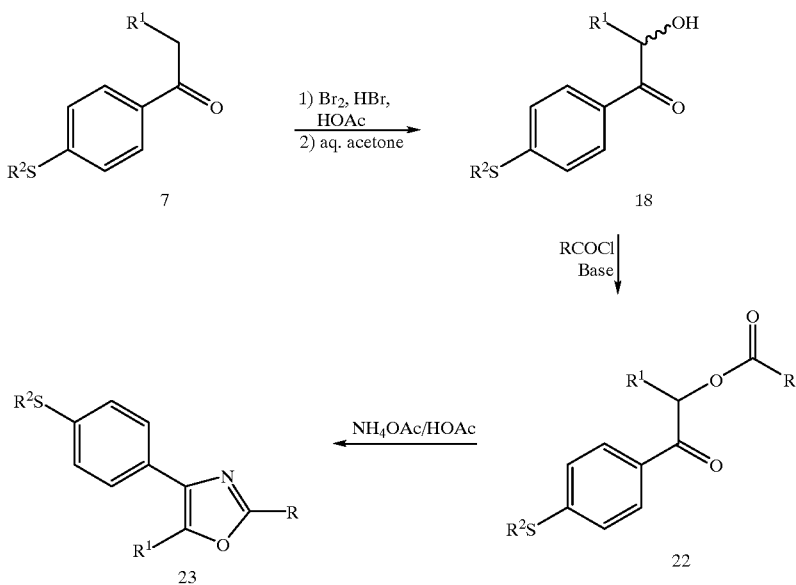

Similarly, Scheme VI shows the four step synthesis which can be used to prepare oxazoles 23 from ketones 7 (prepared in Synthetic Scheme II). In step one, ketones 7 are readily brominated via the addition of bromine in acetic acid to form the 2-bromoethanone intermediates. In step two, reaction of the bromoethanone with aqueous acetone yields the benzoin 21. In step three, reaction of the benzoin 21 with the appropriate acid chloride in the presence of base, such as pyridine, gives the benzoin esters 22. In step four, benzoin esters 22 are converted to the oxazoles 23 upon treatment with ammonium acetate in acetic acid at reflux.

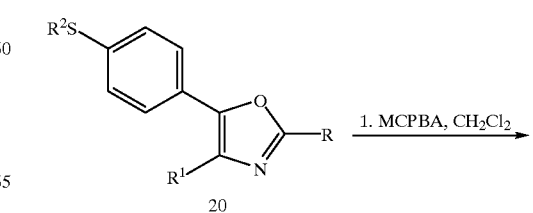

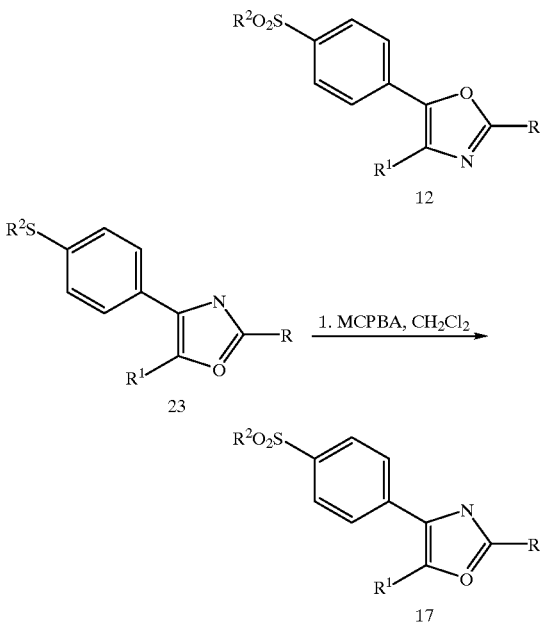

An alternative synthesis of the alkylsulfonylphenyloxazoles 12 and 17 is accomplished as shown in Synthetic Scheme VII from oxazoles 20 and 23 (prepared in Schemes V and VI). Oxazoles 20 and 23, where $R^2$ is an alkyl radical, are oxidized, such as with MCPBA (2 equivalents) in methylene chloride to form the antiinflammatory alkylsulfonyl oxazoles 12 and 17. Other suitable oxidizing agents include Oxone®, hydrogen peroxide, periodate, peracetic acid and the like.

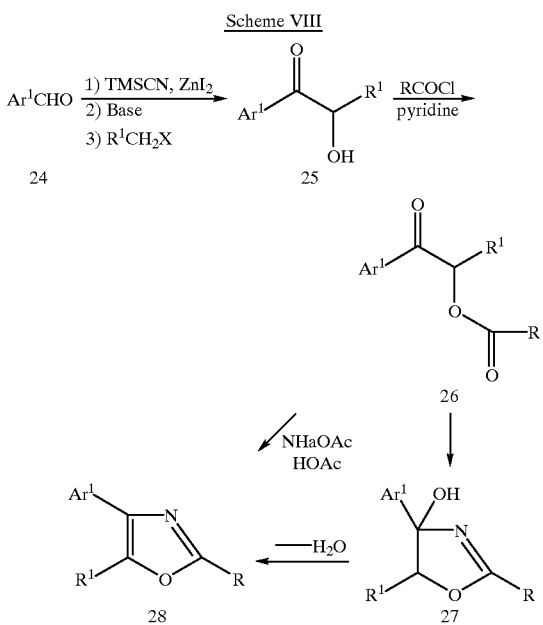

In a method similar to that shown in Scheme IV, Scheme VIII shows a method for preparing oxazoles 28 where $Ar^1$ represents an aromatic or heteroaryl radical without a sulfur substituent. A solution of aldehyde 24 and zinc iodide in an organic solvent such as dichloromethane (100 mL) is treated with trimethylsilylcyanide to give the trimethylsilyl cyano-hydrin. The trimethylsilyl cyanohydrin is added to a solution of $Ar^1$-magnesium bromide in diethyl ether while maintaining the temperature between 25–35° C. to give the keto-enol 25. The benzoin 25, pyridine, and acid chloride are reacted at room temperature to yield the benzoin ester 26. Addition of ammonium acetate to the benzoin ester 26 yields the oxazole 28. Alternatively, the hydroxy-oxazoline 27 is isolated. Dehydration of the hydroxy-oxazoline 27 yields the oxazoles 28. By reversing the positions of $R^1$ and $Ar^1$ in the keto-enol 25, oxazoles can be prepared with $R^1$ is at position 4.

Scheme IX

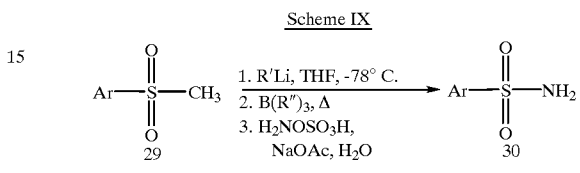

Synthetic Scheme VIII shows the three step procedure used to prepare sulfonamide antiinflammtory agents 30 from their corresponding methyl sulfones 29. In step one, a THF solution of the methyl sulfones 29 at −78° C. is treated with an alkyllithium reagent, e.g., methyllithium, n-butyllithium, etc. In step two, the anions generated in step one are treated with an organoborane, e.g., triethylborane, tributylborane, etc., at −78° C. then allowed to warm to ambient temperature prior to stirring at reflux. In step three, an aqueous solution of sodium acetate and hydroxyamine-O-sulfonic acid is added to provide the corresponding sulfonamide antiinflammatory agents 30 of this invention.

Scheme X

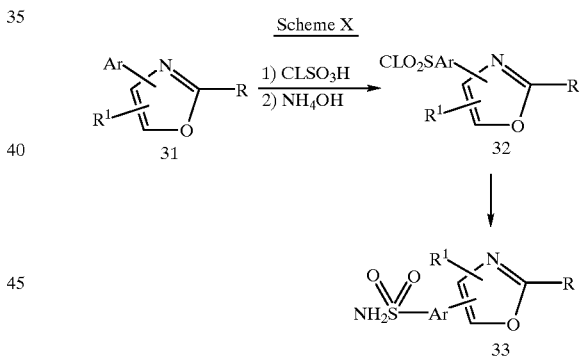

Scheme X shows another method of preparing oxazolylbenzenesulfonamides 33 of the present invention. The oxazole 31 is stirred with chlorosulfonic acid at 5° C. to give the sulfonyl chlorides 32. The sulfonyl chloride 32 is reacted at 5° C. with ammonium hydroxide to give the sulfonamides 33 of the current invention. In additon, disulfonamides can be formed by substitution on $R^1$ where $R^1$ is aryl or heteroaryl.

The following examples contain detailed descriptions of the methods of preparation of compounds of Formula I. These detailed descriptions fall within the scope, and serve to exemplify, the above described General Synthetic Procedures which form part of the invention. These detailed descriptions are presented for illustrative purposes only and are not intended as a restriction on the scope of the invention. All parts are by weight and temperatures are in Degrees centigrade unless otherwise indicated.

EXAMPLE 1

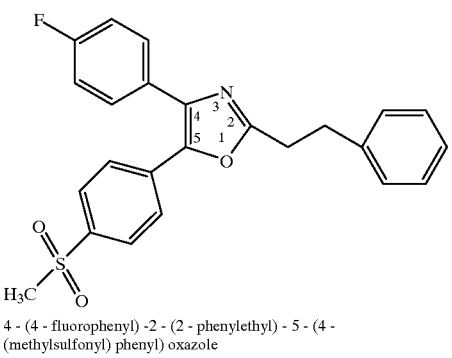

4 - (4 - fluorophenyl) -2 - (2 - phenylethyl) - 5 - (4 - (methylsulfonyl) phenyl) oxazole Step 1: Preparation of 1-(4-fluorophenyl)-2-hydroxy-2-(methylsulfonyl)phenyl)ethanone A suspension of 2.03 g sodium hydride in 125 mL tetrahydrofuran (THF) was stirred at 0° C. under a nitrogen atmosphere as a solution containing 20.0 g of 1-(4-fluorophenyl)-2-[4-(methylthio)phenyl]ethanone, as prepared in U.S. Pat. No. 3,647,858, in 100 mL of THF was added dropwise over 30 minutes. The reaction was allowed to warm to 25° C. for 18 hours. A solution containing 12.7 g (84.5 mmol) of tert-butyl-dimethylsilyl chloride (DBSCL) in 20 mL THF was added over 5 minutes and the resulting solution stirred at 25° C. for 18 hours. The reaction was quenched by pouring into aqueous sodium bicarbonate. The mixture was extracted with ethyl acetate and the combined organic extracts dried over sodium sulfate. Concentration in vacuo provides a yellow oil, which solidified on standing to give 27.9 g of the silyl enol ether. NMR spectra was consistent with the assigned structure. The silyl enol ether was used without further purification.

A solution containing 27.9 g of the silyl enol ether in 500 mL methylene chloride ($CH_2Cl_2$) was cooled to 0° C. under a nitrogen atmosphere while being stirred mechanically. 77.1 g of m-chloroperoxybenzoic acid (technical grade, 50–60%) was added and the reaction was stirred at 0° C. for 2 hours and allowed to warm to 25° C. over 1 hour. The reaction mixture was washed with an aqueous solution of sodium metabisulfite, followed by aqueous sodium bicarbonate. The organic solution was dried over sodium sulfate and concentrated in vacuo to give 24.5 g of 1-(4-fluorophenyl)-2-tert-butyldimethylsilyloxy-2-[4-(methylsulfonyl)phenyl]ethanone. NMR spectra were consistent with the assigned structure. This material was used without further purification.

The benzoin silyl ether was dissolved in 100 mL of 90% aqueous trifluoroacetic acid and stirred at 25° C. for 18 hours. The reaction was quenched by slowly pouring into saturated aqueous sodium bicarbonate solution. The product was extracted with ethyl acetate and the combined organic extracts were dried over sodium sulfate. Concentration in vacuo provided an oily solid, which was recrystallized from 50% ethyl acetate/isooctane to give 15.5 g of a crystalline white solid (mp 122–123° C.) whose structure was assigned as 1-(4-fluorophenyl)-2-hydroxy-2-(methylsulfonyl)phenyl) ethanone on the basis of its spectral properties.

The isomeric benzoin, 2-(4-fluorophenyl)-2-hydroxy-1-(4-(methylsulfonyl)phenyl)ethanone, was prepared analogously from 2-(4-fluorophenyl)-1-[4-(methylthio)phenyl ethanone.

Step 2: Preparation of 4-(4-fluorophenyl)-2-(2-phenylethyl)-5-(4-(methylsulfonyl)phenyl)oxazole.

A solution containing 5.00 g of 1-(4-fluorophenyl)-2-hydroxy-2-(4-(methylsulfonyl)phenyl)ethanone in 100 mL methylene chloride ($CH_2Cl_2$) was stirred at 25° C. as 6.60 mL of pyridine was added, followed by 3.61 mL of hydrocinnamoyl chloride.

The reaction was stirred at 25° C. for 48 hours, after which the organic solution was washed with 1N HCl, dried over sodium sulfate and concentrated in vacuo to give an oily solid. This material was recrystallized from 50% ethyl acetate/isooctane to give 4.40 g of a beige crystalline solid (mp 152–153.5° C.). NMR spectra were consistent with the assigned structure of 1-(4-fluorophenyl)-2-[4-(methylsulfonyl)phenyl]-2-(2-phenyl)propionyloxy ethanone. This material was dissolved in 100 mL of glacial acetic acid and 7.70 g of ammonium acetate was added. The reaction was heated to reflux with stirring for 1.5 hours, after which it was cooled to room temperature and poured into 100 mL of water. The product was extracted with ethyl acetate and the combined organic extracts washed with aqueous sodium bicarbonate, dried over sodium sulfate and concentrated in vacuo to give an oily solid which was recrystallized from 50% ethyl acetate/isooctane to give 3.55 g of 4-(4-fluorophenyl)-2-(2-phenylethyl)-5-(4-(methylsulfonyl) phenyl)oxazole as a white crystalline solid (mp 117–118° C.). NMR spectra was consistent with the assigned structure.

EXAMPLE 2

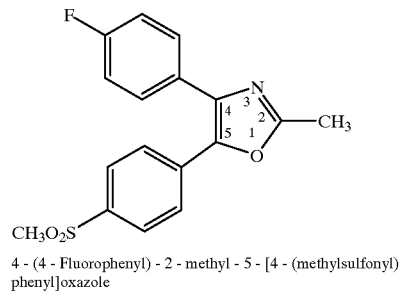

4 - (4 - Fluorophenyl) - 2 - methyl - 5 - [4 - (methylsulfonyl) phenyl]oxazole 4-(4-Fluorophenyl)-2-methyl-5-[4-(methylsulfonyl) phenyl]oxazole was prepared in an analogous manner to that shown in Example 1. Melting point: 158–159° C.

EXAMPLE 3

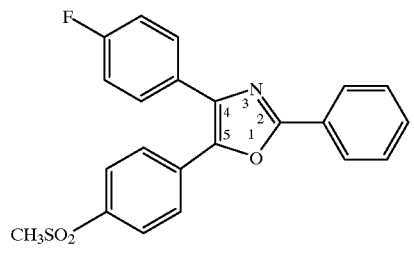

4 - (4 - Fluorophenyl) - 5 - [4 - (methylsulfonyl) phenyl] - 2 - phenyloxazole 4-(4-Fluorophenyl)-5-[4-(methylsulfonyl) phenyl]-2-phenyloxazole was prepared in a manner analogous to Example 1. Melting point: 204–205° C.

EXAMPLE 4

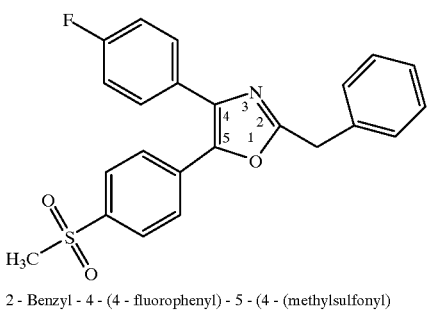

2 - Benzyl - 4 - (4 - fluorophenyl) - 5 - (4 - (methylsulfonyl) phenyloxazole

2-Benzyl-4-(4-fluorophenyl)-5-(4-(methylsulfonyl) phenyloxazole was prepared in a manner analogous to Example 1. The m/z 408 (M+H)+ was consistent with the assigned structure.

EXAMPLE 5

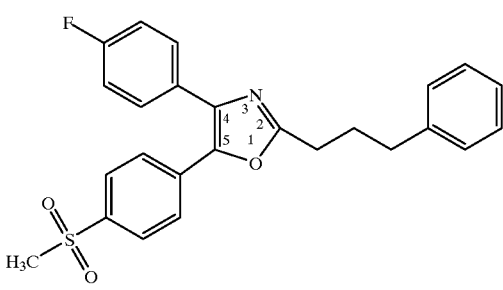

4 - (4 - Fluorophenyl) - 5 - [4 - (methylsulfonylphenyl] - 2 - (3 - phenylpropyl)oxazole 4-(4-Fluorophenyl)-5-[4-methylsulfonyl phenyl]-2-(3-phenylpropyl)oxazole was prepared in a manner analogous to Example 1. The m/z 436 (M+H)+ was consistent with the assigned structure.

EXAMPLE 6

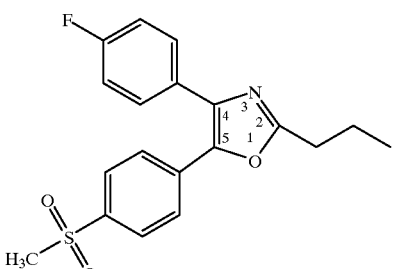

4 - (4 - Fluorophenyl) - 2 - (4 - (methyloxylphenyl) - 5 - [4 - methylsulfonylpheny]oxazole 4-(4-Fluorophenyl)-5-[4-methylsulfonyl phenyl]-2-propyloxazole was prepared in a manner analogous to Example 1. The m/z 360 (M+H)+ was consistent with the assigned structure.

EXAMPLE 7

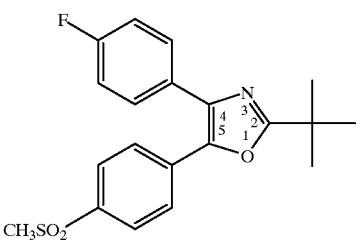

2 - (tert - Butyl) - 4 - (4 - fluorophenyl) - 5 - [4 - (methylsulfonyl)phenyl]oxazole 2-(Tert-butyl)-4-(4-fluorophenyl)-5-[4-(methylsulfonyl) phenyl]oxazole was prepared in a manner analogous to Example 1. Melting point: 130–131° C.

EXAMPLE 8

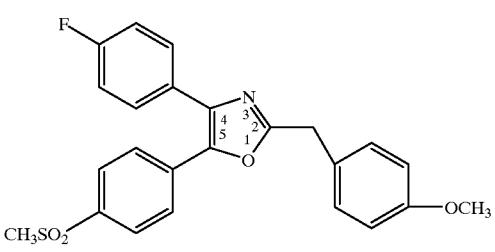

4 - (4 - Fluorophenyl) - 2 - (4 - methoxyphenyl)methyl - 5- [4 - methylsulfonylphenyl]oxazole 4-(4-Fluorophenyl)-2-(4-methoxyphenyl)methyl-5-[4-methylsulfonylphenyl]oxazole was prepared in a manner analogous to Example 1. Melting point: 123–124° C.

EXAMPLE 9

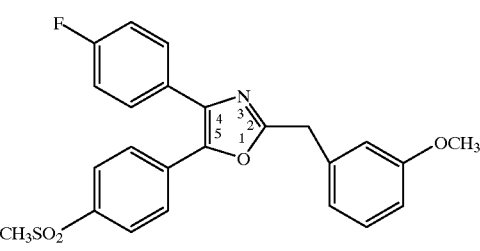

4 - (4 - Fluorophenyl) - 2 - (3 - methoxyphenyl)methyl - 5- [4 - methylsulfonylphenyl]oxazole 4-(4-Fluorophenyl)-2-(3-methoxyphenyl)methyl-5-[4-methylsulfonylphenyl]oxazole was prepared in a manner analogous to Example 1. The m/z 437 (M+H)+ was consistent with the assigned structure.

EXAMPLE 10

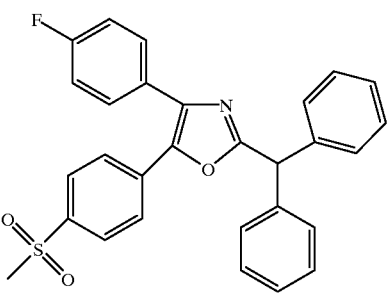

2 - Diphenylmethyl - 4 - (4 - fluorophenyl) - 5 - [4 - methylsulfonylphenyl]oxazole 2-Diphenylmethyl-4-(4-fluorophenyl)-5-[4-methylsulfonylphenyloxazole] was prepared in a manner analogous to Example 1. Melting Point: 155–156° C.

EXAMPLE 11

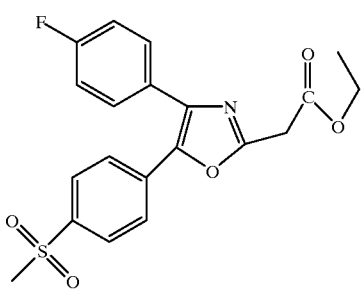

Ethyl 2 - [4 - (4 - fluorophenyl) - 5 - (4 - methylsulfonylphenyl)] - 2 - oxazoleacetate Ethyl 2-[4-(4-fluorophenyl)-5-(4-methylsulfonylphenyl)-2-oxazoleacetate was prepared in a manner analogous to Example 1. Melting point: 123–124° C.

EXAMPLE 12

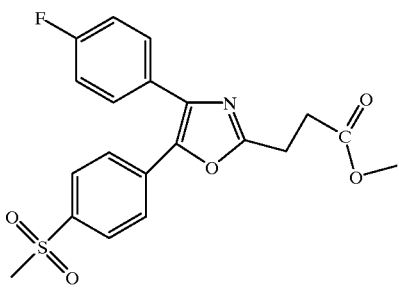

Methyl 3 - [4 - (4 - fluorophenyl) - 5 - (4 - methylsulfonylphenyl)] - 2 - oxazolepropanate Methyl 3-[4-(4-fluorophenyl)-5-[4-methylsulfonylphenyl]oxazol-2-yl]propanate was prepared in a manner analogous to Example 1. The m/z 404 (M+H)$^+$ was consistent with the assigned structure.

EXAMPLE 13

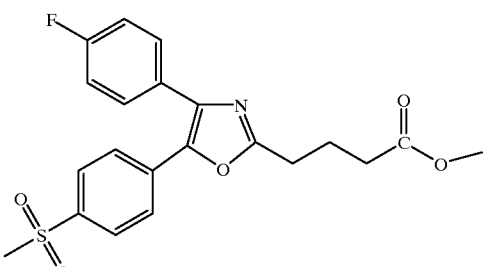

Methyl 4 - (4 - fluorophenyl) - 5 - [4 - (methylsulfonyl) phenyl]] - 2 - oxazolebutanate Methyl 4-[4-(4-fluorophenyl)-5-[4-(methylsulfonyl)phenyl]]-2-oxazolebutanate was prepared in a manner analogous to Example 1. Melting point: 89–91° C.

EXAMPLE 14

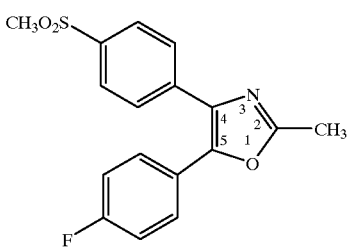

5 - (4 - Fluorophenyl) - 2 - methyl - 4- [ 4 - (methylsulfonyl) phenyl]oxazole 5-(4-Fluorophenyl)-2-methyl-4-[4-(methylsulfonyl)phenyl]oxazole was prepared in a manner analogous to Example 1 but with 2-(4-fluorophenyl)-1-[4-(methylthio)phenyl]ethanone as the starting material. The m/z 332 (M+H)$^+$ was consistent with the assigned structure.

EXAMPLE 15

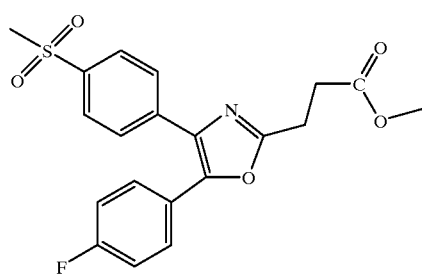

Methyl 3 - [5 - (4 - fluorophenyl) - 4 - [4 - (methylsulfonyl) phenyl]] - 2 - oxazolepropanoate Methyl 3-[5-(4-fluorophenyl)-4-[4-(methylsulfonyl)phenyl]]-2-oxazolepropanoate was prepared in a manner analogous to Example 14. The m/z 404 (M+H)$^+$ was consistent with the assigned structure.

EXAMPLE 16

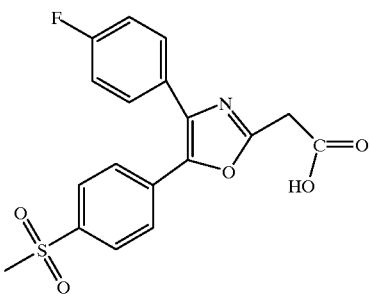

2 - [4 - (4 - Fluorophenyl) - 5 - [4 - (methylsulfonyl) phenyl]] - 2 - oxazoleleacetic acid 2-[4-(4-Fluorophenyl)-5-[4-(methylsulfonyl) phenyl]oxazol-2-yl]acetic acid was prepared from Example 11 via alkaline hydrolysis using 1 N sodium hydroxide in methanol and appropriate reaction conditions. Melting point: 118–120° C.

EXAMPLE 17

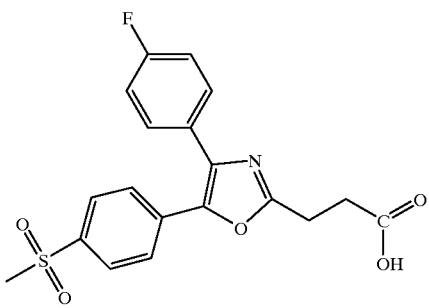

3-[4-(4-Fluorophenyl)-5-[4-(methylsulfonyl)phenyl]]-2-oxazolepropanoic acid

3-[4-(4-Fluorophenyl)-5-[4-(methylsulfonyl) phenyl]]-2-oxazolepropanoic acid was prepared from Example 12 in a manner analogous to Example 17. Melting point: 197–198° C. The m/z 390 (M+H)+ was consistent with the assigned structure.

EXAMPLE 18

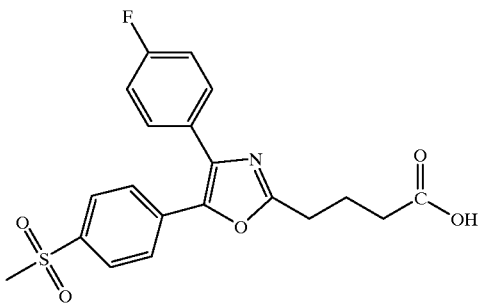

4-[4-(4-Fluorophenyl)-5-[4-(methylsulfonyl)phenyl]]-2-oxazolebutanoic acid

4-[4-(4-Fluorophenyl)-5-[4-(methylsulfonyl) phenyl]]-2-oxazolebutanoic acid was prepared from Example 13 in a manner analogous to Example 17. Melting point: 140–141° C. The m/z 404 (M+H)+ was consistent with the assigned structure.

EXAMPLE 19

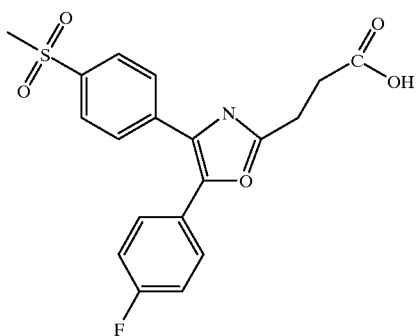

3-[5-(4-Fluorophenyl)-4-[4-(methylsulfonyl)phenyl]]-2-oxazolepropanoic acid

3-[5-(4-Fluorophenyl)-4-[4-(methylsulfonyl) phenyl]]-2-oxazolpropanoic acid was prepared from Example 15 in a manner analogous to Example 17. The m/z 390 (M+H)+ was consistent with the assigned structure.

EXAMPLE 20

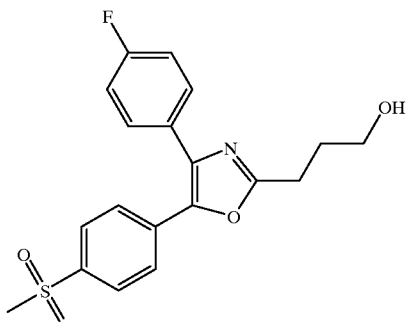

4-(4-Fluorophenyl)-2-(3-hydroxypropyl)-5-[4-(methylsulfonyl)phenyl]oxazole

A solution containing 100 mg (0.239 mmol) of 3-[4-(4-fluorophenyl)-5-[4-(methylsulfonyl)phenyl]oxazol-2-yl] propanoic acid, methyl ester in 10 mL of tetrahydrofuran was cooled to 0° C. with stirring under a nitrogen atmosphere as 0.53 mL of diisobutylaluminum hydride (1M in toluene, 0.523 mmol) was added dropwise over 5 minutes. The reaction was allowed to warm to 25° C. and poured into 100 mL of a saturated solution of sodium potassium tartarate. Ethyl acetate (100 mL) was added and the mixture was stirred until the layers separated (approx. 1 hour). The organic layer was separated and dried over sodium sulfate. Concentration in vacuo gave an oily solid, which was recrystallized from 50% ethyl acetate-isooctane to give 75 mg of a white crystalline solid (mp 123–124° C.) which was characterized on the basis of its spectral characteristics: $^1$H-NMR (CDCl$_3$, 300 MHz) δ 2.10 (m, 2H) 2.56 (bs, 1H), 3.01 (t, 2H, J=7.0 Hz), 3.07 (s, 3H), 3.80 (t, 2H, J=5.9 Hz), 7.09 (t, 2H, J=8.5 Hz), 7.57 (dd, 2H, J=8.5 and 5.5 Hz), 7.73 (d, 2H, J=8.5 Hz) and 7.89 (d, 2H, J=8.5 Hz). $^{19}$F-NMR (CDCl$_3$, 280 MHz), δ −111.97. LRMS m/z 376 (M+H)+. HRMS calc. for C$_{19}$H$_{18}$NO$_4$FS: 376.1019. Observed: 376.1026. Analysis calc. for C$_{19}$H$_{18}$NO$_4$FS-C: 60.79, H: 4.83, N: 3.73. Observed-C: 60.53, H: 4.85, N: 3.66.

EXAMPLE 21

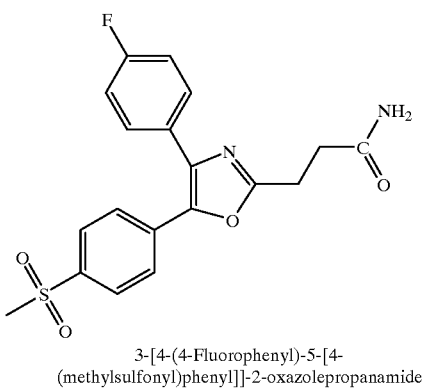

3-[4-(4-Fluorophenyl)-5-[4-(methylsulfonyl)phenyl]]-2-oxazolepropanamide

3-[4-(4-fluorophenyl)-5-[4-(methylsulfonyl) phenyl]]-2-oxazolepropanamide was prepared by treating methyl 3-[4-(4-fluorophenyl)-5-(4-(methylsulfonyl)phenyl)-2-oxazolepropanoic acid, (Example 12) with excess ammonia in methanol for 5 days. Melting point: 193–195° C.

EXAMPLE 22

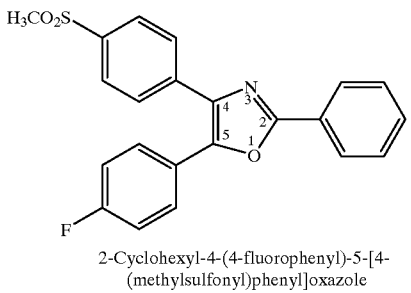

2-Cyclohexyl-4-(4-fluorophenyl)-5-[4-(methylsulfonyl)phenyl]oxazole

Step 1: Preparation of 5-(fluorophenyl)-4-[4-(methylthio) phenyl]-2-phenyloxazole A solution containing 560 mg (2.03 mmol) of 2-(4-fluorophenyl)-2-hydroxy-1-[4-(methylthio)phenyl]ethanone in 50 mL of methylene chloride was stirred at 25° C. as 0.82 mL (10.15 mmol) of pyridine was added, followed by 0.28 mL (2.44 mmol) of benzoyl chloride. The reaction was stirred at 25° C. for 2 days, after which it was washed with 1N HCl, dried over sodium sulfate and concentrated in vacuo to give a crude oil which was characterized as the benzoin ester on the basis of its spectral characteristics: $^1$H-NMR (CDCl$_3$, 300 MHz) δ2.53 (s, 3H), 7.08 (s, 1H), 7.12 (t, 2H, J=8.7 Hz), 7.27 (d, 2H, J=8.7 Hz), 7.49 (t, 2H, J=7.7 Hz), 7.60 (m, 3H), 7.94 (d, 2H, J=8.7 Hz) and 8.14 (d, 2H, J=8.7 Hz). This material was dissolved in 50 mL of glacial acetic acid and 1.56 g (20.3 mmol) of ammonium acetate was added. The reaction was heated at reflux for 2 hours, cooled to 25° C. and poured into 100 mL of water. The aqueous solution was extracted with ethyl acetate and the combined organic extracts were washed with water and sodium bicarbonate solution, dried over sodium sulfate and concentrated in vacuo. The crude solid was purified by flash chromatography using a silica gel column and 50% ethyl acetate/hexane as the eluent to give a white solid which was recrystallized from 50% ethyl acetate/isooctane to give 450 mg (61%) of a white crystalline solid (mp 118–119° C.) whose structure was assigned as 5-(4-fluorophenyl)-4-[4-(methylthio) phenyl]-2-phenyl oxazole on the basis of its spectral characteristics: $^1$H-NMR (CDCl$_3$, 300 MHz) δ2.52 (s, 3H), 7.10 (t, 2H, J=8.8 Hz), 7.28 (d, 2H, J=8.5 Hz), 7.47 (m, 3H) , 7.62 (m, 4H) and 8.13 (m, 2H). $^{19}$F-NMR (CDCl$_3$, 280 MHz) δ –111.96. LRMS m/z 361 (M)+. HRMS Calc'd. for C$_{22}$H$_{16}$NOFS: 361.0937. Observed: 361.0970. Analysis Calc'd. for C$_{22}$H$_{16}$NOFS: C, 71.51; H, 6.55; N, 3.79. Observed: C, 72.85; H, 4.52; N, 3.84.

Step 2: Preparation of 5-(4-fluorophenyl)-4-[4-(methylsulfinyl)phenyl]-2-phenyloxazole.

A solution containing 64 mg (0.173 mmol) of 5-(4-fluorophenyl)-4-[4-(methylthio)phenyl]-2-phenyloxazole in 10 mL of methylene chloride was stirred at –78° C. as 60 mg (0.173 mmol based on 50% purity) of m-chloroperoxybenzoic acid was added all at once. The reaction was stirred at –78° C. for 1 hour. Thin-layer chromatography (TLC) (silica, 50% hexane-ethyl acetate) indicated that the reaction mixture consisted of mostly sulfoxide, with a minor amount of sulfide and sulfone. The reaction was poured into a solution of aqueous sodium metabisulfite. The aqueous solution was extracted using ethyl acetate and the organic layer was washed with saturated sodium metabisulfite, saturated sodium bicarbonate and brine. The resulting clear solution was dried over sodium sulfate and concentrated in vacuo to give a white solid which was purified by flash chromatography on a silica gel column using 50% ethyl acetate/hexane as the eluent. Recrystallization from 50% ethyl acetate/isooctane gave 48 mg (74%) of a white crystalline solid (mp 164–165° C.) whose structure was assigned as 5-(4-fluorophenyl)-4-[4-(methylsulfinyl)phenyl]-2-phenyl oxazole on the basis of its spectral characteristics: $^1$H-NMR (CDCl$_3$, 300 MHz) δ 2.80 (s, 3H), 7.16 (t, 2H, J=8.5 Hz), 7.54 (m, 3H), 7.66–7.75 (m, 4H), 7.93 (d, 2H, J=8.5 Hz) and 8.19 (m, 2H). LRMS m/z 377 (M)+. HRMS Calc'd. for C$_{22}$H$_{16}$NO$_2$FS: 377.0886. Observed: 377.0868. Analysis Calc'd. for C$_{22}$H$_{16}$NO$_2$FS: C,70.01; H, 4.27; N, 3.71. Observed: C, 68.18; H, 4.19; N, 3.58.

Step 3: Preparation of 5-(4-fluorophenyl)-4-[4-(methylsulfonyl)phenyl]-2-phenyloxazole.

A solution containing 64 mg (0.173 mmol) of 5-(4-fluorophenyl)-4-(4-(methylthio)phenyl]-2-phenyloxazole in 10 mL of methylene chloride was stirred at –78° C. as 120 mg (0.346 mmol based on 50% purity) of m-chloroperoxybenzoic acid was added all at once. The reaction was stirred at –78° C. for 1 hour and TLC (silica, 50% hexane-ethyl acetate) indicated that the reaction mixture consisted of mostly sulfone. The reaction was poured into a solution of aqueous sodium metabisulfite. The aqueous solution was extracted using ethyl acetate and the organic layer was washed with saturated sodium metabisulfite, saturated sodium bicarbonate and brine. The resulting clear solution was dried over sodium sulfate and concentrated in vacuo to give a white solid which was purified by flash chromatography on a silica gel column using 50% ethyl acetate/hexane as the eluent. Recrystallization from 50% dichloromethane/isooctane gave 62 mg (91%) of a white crystalline solid (mp 175–176° C.) whose structure was assigned as 5-(4-fluorophenyl)-4-[4-(methylsulfonyl)phenyl]-2-phenyl oxazole on the basis of its spectral characteristics: $^1$H-NMR (CDCl$_3$, 300 MHz) δ 3.13 (s, 3H), 7.19 (t, 2H, J=8.6 Hz), 7.55 (m, 3H), 7.69 (m, 2H), 8.00 (m, 2H), 8.17 (m, 2H). LRMS m/z 393 (M)+. HRMS Calc'd. for C$_{22}$H$_{16}$NO$_3$FS: 393.0835. Observed: 393.0865.

EXAMPLE 23

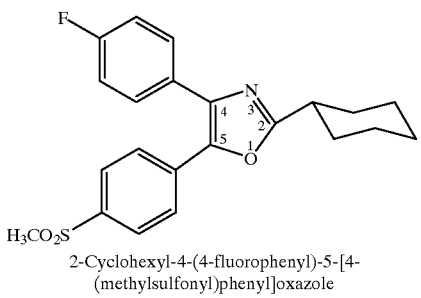

2-Cyclohexyl-4-(4-fluorophenyl)-5-[4-(methylsulfonyl)phenyl]oxazole

2-Cyclohexyl-4-(4-fluorophenyl)-5-[4-(methylsulfonyl) phenyl]oxazole was prepared in a manner analogous to Example 1. Melting point: 127–128° C.

EXAMPLE 24

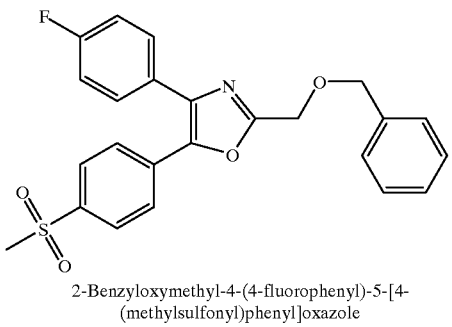

2-Benzyloxymethyl-4-(4-fluorophenyl)-5-[4-(methylsulfonyl)phenyl]oxazole

Step 1: Preparation of the benzoin ester

A solution containing 2.07 g (6.71 mmol) of 1-(4-fluorophenyl)-2-hydroxy-2-[4-(methylsulfonylphenyl) ethanone in 100 mL of methylene chloride was stirred at 25° C. as 2.71 mL (33.55 mmol) of pyridine was added, followed by the addition of 1.27 mL (8.05 mmol) of benzyloxyacetyl chloride. The reaction was stirred at 25° C. for 48 hours, after which the resulting yellow solution was washed with 1N HCl, dried over sodium sulfate and concentrated in vacuo. The oily yellow solid was purified via flash chromatography on a silica gel column using 20% ethyl acetate/hexane as the eluent. This provided 2.22 g (73%) of a white foam, which was characterized as the benzoin ester on the basis of its NMR spectra: $^1$H-NMR (CDCl$_3$, 300 MHz) δ 3.03 (s, 3H), 4.23 (d, 1H, J=17.0 Hz), 4.33 (d, 1H, J=17.0 Hz), 4.67 (s, 2H), 6.95 (s, 1H), 7.13 (t, 2H, J=8.5 Hz), 7.35 (m, 5H), 7.66 (d, 2H, J=8.1 Hz) and 7.98 (m, 4H). $^{19}$F-NMR (CDCl$_3$, 280 MHz) δ −102.5.

Step 2: Preparation of 2-benzyloxymethyl-4-(4-fluorophenyl)-5-[4-(methylsulfonyl)phenyl]oxazole.

A solution containing 2.22 g (4.86 mmol) of the benzoin ester and 3.74 g (48.6 mmol) of ammonium acetate in 100 mL of acetic acid was heated to 80° C. for 2 hours. The reaction was cooled to 25° C. and poured into water. The product was extracted into ethyl acetate and the combined organic extracts washed with an aqueous solution of sodium bicarbonate. The solution was dried over sodium sulfate and concentrated in vacuo to give a yellow oil. This crude material was purified by flash chromatography on a silica gel column using 25% ethyl acetate/hexane as the eluent to give 1.92 g (90%) of a clear oil, which was characterized as 2-benzyloxymethyl-4-(4-fluorophenyl)-5-[4-(methylsulfonyl)phenyl]oxazole on the basis of its spectral properties: $^1$H-NMR (CDCl$_3$, 300 MHz) δ 3.07 (s, 3H), 4.70 (s, 2H), 4.72 (s, 2H), 7.11 (t, 2H, J=8.8 Hz), 7.22–7.40 (m, 5H), 7.58 (m, 2H), 7.76 (d, 2H, J=8.8 Hz) and 7.91 (d, 2H, J=8.8 Hz). $^{19}$F-NMR (CDCl$_3$, 280 MHz) δ −111.88.

EXAMPLE 25

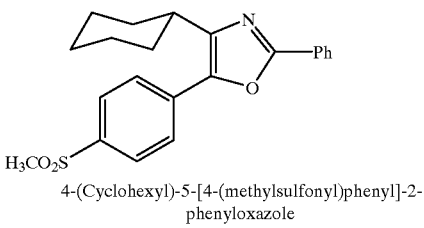

4-(Cyclohexyl)-5-[4-(methylsulfonyl)phenyl]-2-phenyloxazole

Step 1: Preparation of 1-(cyclohexyl)-2-hydroxy-2-[4-(methylthiophenyl)ethanone

A 250 mL round bottomed flask was equipped with a mechanical stirrer and reflux condenser and charged with 30 mL of absolute ethanol, 3,4-dimethyl-5-(2-hydroxyethyl) thiazolium iodide (2.00 g, 7.0 mmol), 4-methylthiobenzaldehyde (10.66 g, 70.0 mmol), and freshly distilled cyclohexanecarboxaldehyde (7.68 g, 70.1 mmol). The solution was stirred vigorously, treated with triethylamine (4.27 g, 42.2 mmol) and heated to reflux for 24 hours. The solution was treated with additional portions of 3,4-dimethyl-5-(2-hydroxyethyl)thiazolium iodide (2.05 g, 7.01 mmol), triethylamine (4.84 g, 48.0 mmol), and cyclohexanecarboxaldehyde (7.01 g, 62.5 mmol), and heated to reflux for an additional 42 hours. The solution was concentrated in vacuo, the residue dissolved in chloroform, washed with 3 N HCl, saturated aqueous sodium bicarbonate, brine, dried over anhydrous magnesium sulfate, filtered and concentrated in vacuo to afford 18.75 g, (>100%) of a yellow oil that solidified upon standing. The crude solid was purified by trituration with ether providing the desired compound in pure form 15.80 g, (86%, mp 110–111.5° C.) which was characterized as 1-(cyclohexyl)-2-hydroxy-2-[4-(methylthiophenyl)ethanone on the basis of its NMR spectra. $^1$H-NMR (CDCl$_3$, 300 MHz) δ 1.00–1.47 (m, 6H), 1.60–1.95 (m, 4H), 2.45 (m, 1H), 2.52 (s, 3H), 4.38(d, J=3.9 Hz, 1H), 7.55 (d, J=3.9 Hz, 1H), 7.25 (m, 4H). HRMS Calc'd. for $C_{15}H_{20}NO_2S$: 264.1184. Observed: 264.1207.

Step 2: Preparation of benzoin ester

A solution containing 162 mg (0.62 mmol) of 1-(cyclohexyl)-2-hydroxy-2-[4-(methylthiophenyl) ethanone in 10 mL of methylene chloride was stirred at 25° C. as 251 µL (31 mmol) of pyridine was added, followed by the addition of 86 µL (1.24 mmol) of benzoyl chloride. The reaction was stirred at 25° C. for 48 hours, after which the resulting yellow solution was washed with 1N HCl, dried over sodium sulfate and concentrated in vacuo. The crude solid was purified via flash chromatography on a silica gel column using 10% ethyl acetate/hexane as the eluent. This provided 131 mg (57%) of a white foam, which was characterized as the benzoin ester on the basis of its NMR spectra: $^1$H-NMR (CDCl$_3$, 300 MHz) δ 1.03–1.48 (m, 6H), 1.56–1.88 (m, 3H), 2.03–2.14 (m, 1H), 2.48 (s, 3H), 2.53 (m, 1H), 6.28 (s, 1H), 7.20–7.70 (m, 5H), 8.05–8.17 (m, 4H).

Step 3: Preparation of 4-cyclohexyl-5-[4-(methythio) phenyl]-2-phenyloxazole

A solution containing 131 mg (0.355 mmol) of the benzoin ester and 273 mg (35 mmol) of ammonium acetate in 10 mL of acetic acid was heated to 80° C. for 2 hours. The reaction was cooled to 25° C. and poured into water. The product was extracted into ethyl acetate and the combined organic extracts washed with an aqueous solution of sodium bicarbonate. The solution was dried over sodium sulfate and concentrated in vacuo to give the crude oxazole. This crude material was purified crystallization from admixture of dichloromethane and isooctane to give 89 mg, (72%, mp 151–151.5° C.) of material, which was characterized as 4-(cyclohexyl)-5-[4-(methythio)phenyl]-2-phenyloxazole on the basis of its spectral properties: $^1$H-NMR (CDCl$_3$, 300 MHz) δ 1.30–1.45 (m, 3H), 1.70–1.94 (m, 7H), 2.54 (s, 3H), 2.80–2.90 (m, 1H), 7.34 (d, J=8.5Hz, 2H), 7.42 (m, 3H), 7.55 (d, J=8.5Hz, 2H), 8.08 (d, J=7.7Hz, 2H). HRMS Calc'd. for $C_{22}H_{23}NOS$ (M+H): 350.1579. Observed: 350.1597. The material from this experiment was used directly in the next step without further purification.

Step 4: Preparation of 4-(cyclohexyl)-5-[4-(methylsulfonyl) phenyl]-2-phenyloxazole A solution of 38 mg (0.11 mmol) of 2-phenyl-4-(cyclohexyl)-5-[4-(methythio)phenyl]oxazole in 4 mL of methylene chloride was stirred at −78° C. as 75 mg (0.22 mmol based on 50% purity) of m-chloroperoxybenzoic acid was added all at once. The reaction was stirred at −78° C. for 1 hour. Thin-layer chromatography (TLC) (silica, 50% hexane/ethyl acetate) indicated the reaction mixture consisted of mostly sulfone. The reaction was poured into a solution of aqueous sodium metabisulfite. The aqueous solution was extracted using ethyl acetate and the organic layer was washed with saturated sodium metabisulfite, saturated sodium bicarbonate and brine. The resulting clear solution was dried over sodium sulfate and concentrated in vacuo to give a white solid which was purified by crystallization from 50% dichloromethane/isooctane gave 26 mg (62%) of pure product, whose structure was assigned as 4-(cyclohexyl)-5-[4-(methylsulfonyl)phenyl]-2-phenyloxazole on the basis of its spectral characteristics: mp 231° C. $^1$H-NMR (CDCl$_3$, 300 MHz) δ 1.34–1.43 (m, 3H), 1.72–1.95 (m, 7H), 2.84 (m, 1H), 3.10 (s, 3H), 7.47 (m, 3H), 7.82 (d, J=8Hz, 2H), 8.03 (d, J=8Hz, 2H) , 8.10 (m, 2H). LRMS m/z 382 (M)+. HRMS Calc'd. for $C_{22}H_{23}NO_3S$: 382.1477. Observed: 382.1436. Analysis Calc'd. for $C_{22}H_{23}NO_3S$: C, 69.27; H, 6.08; N, 3.67. Observed: C, 68.99; H, 6.07; N, 3.63.

EXAMPLE 26

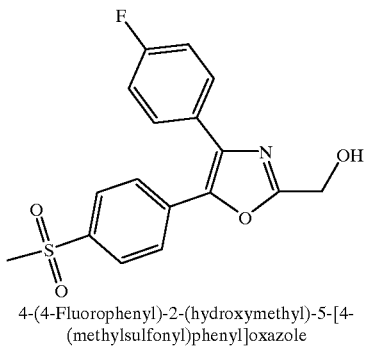

4-(4-Fluorophenyl)-2-(hydroxymethyl)-5-[4-(methylsulfonyl)phenyl]oxazole

To a solution containing 5.0 g (11.4 mmol) of 2-benzyloxymethyl-4-(4-fluorophenyl)-5-[4-(methylsulfonyl)phenyl]oxazole (prepared in Example 24) in 20 mL of 50% THF-methanol, was added 100 mg of 10% Pd on charcoal in a Fisher-Porter bottle. The reaction vessel was evacuated and then charged with hydrogen at 50 psi for 24 hours. The Pd on carbon was removed by filtration through diatomaceous earth and the filtrate concentrated in vacuo to give 3.8 g (97%) of a white crystalline solid (mp 156–157° C.) (recrystallized from 50% ethyl acetate/isooctane) whose structure was assigned as 4-(4-fluorophenyl)-2-hydroxymethyl-5-[4-(methylsulfonyl) phenyl]oxazole on the basis of its spectral characteristics: $^1$H-NMR (CDCl$_3$, 300 MHz) δ 3.07 (s, 3H), 3.21 (bs, 1H), 4.81 (s, 2H), 7.10 (t, 2H, J=8.5 Hz), 7.56 (m, 2H), 7.72 (d, 2H, J=8.8 Hz) and 7.90 (d, 2H, J=8.8 Hz). $^{19}$F-NMR (CDCl$_3$, 280 MHz) δ −111.5. LRMS m/z 348 (M+H)+. HRMS Calc'd. for $C_{17}H_{14}NO_4FS$: 348.0706. Observed: 348.0681. Analysis Calc'd. for $C_{17}H_{14}NO_4FS$: C:, 58.78; H, 4.06; N, 4.03. Observed: C, 58.67; H, 4.02; N, 4.01.

EXAMPLE 27

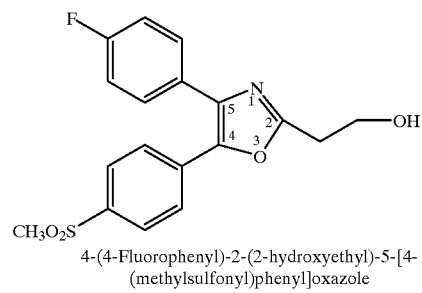

4-(4-Fluorophenyl)-2-(2-hydroxyethyl)-5-[4-(methylsulfonyl)phenyl]oxazole 4-(4-Fluorophenyl)-2-(2-hydroxyethyl)-5-[4-(methylsulfonyl)phenyl]oxazole was prepared in a manner consistent with that described in Example 20. The m/z 362 (M+H)$^+$ was consistent with the assigned structure.

EXAMPLE 28

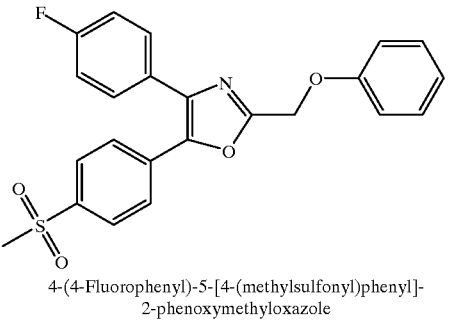

4-(4-Fluorophenyl)-5-[4-(methylsulfonyl)phenyl]-2-phenoxymethyloxazole

A solution containing 1.69 g (4.87 mmol) of 4-(4-fluorophenyl)-2-hydroxymethyl-5-[4-(methylsulfonyl) phenyl]oxazole (Example 26) in 100 mL of methylene chloride was stirred at 25° C. as 1.36 mL (9.74 mmol) of triethylamine was added dropwise, followed by the addition of 560 uL (7.30 mmol) of methanesulfonyl chloride. The reaction was stirred for 20 minutes, r which the organic solution was washed with 1N HCl, d over sodium sulfate and concentrated in vacuo to methyl [4-(4-fluorophenyl)-5-(4- methylsulfonyl)phenyl]oxazol-2-yl]methanesulfonate as a ow oil which was characterized as the expected late by its NMR spectrum: $^1$H-NMR (CDCl$_3$, 400 MHz) δ (s, 3H), 3.17 (s, 3H), 5.37 (s, 2H), 7.12 (t, 2H, 8 Hz), 7.58 (m, 2H), 7.78 (d, 2H, J=8.8 Hz) and 7.94 (2H, J=8.8 Hz). This material was used without further purification. A solution containing 544 mg 8 mmol) of methyl [4-(4-fluorophenyl)-

5-[4-(methylsulfonyl)phenyl]oxazol-2-yl]methanesulfonate in L of DMF was stirred at 25° C. as 353 mg (2.56 mmol) potassium carbonate and 240 mg (2.56 mmol) of phenol added. The reaction was stirred for 2 days at 25° C. poured into 100 mL of water. To this mixture was 100 mL of ethyl acetate and the layers separated. organic layer was washed with water, dried over um sulfate and concentrated in vacuo to give a crude a solid which was purified by flash chromatography silica gel column using 25% ethyl acetate/hexane as eluent to give 475 mg (88%) of a white solid which recrystallized from 50% ethyl acetate/isooctane to a white crystalline solid (mp 168–169° C.) whose structure was assigned as 4-(4-fluorophenyl)-5-[4-(methylsulfonyl)-phenyl]-2-phenoxymethyloxazole on the s of its spectral characteristics: $^1$H-NMR (CDCl$_3$, MHz) δ 3.07 (s, 3H), 5.23 (s, 2H), 6.98 (m, 5H), (t, 2H, J=8.2 Hz), 7.60 (m, 2H), 7.77 (d, 2H, J=8.5 and 7.92 (d, 2H, J=8.5 Hz). $^{19}$F-NMR (CDCl$_3$, 280 MHz) 11.9. Analysis calc. for C$_{23}$H$_{18}$NC$_4$FS- C: 65.24, H: 3.31. Observed- C: 65.10, H: 4.29, N: 3.28.

EXAMPLE 29

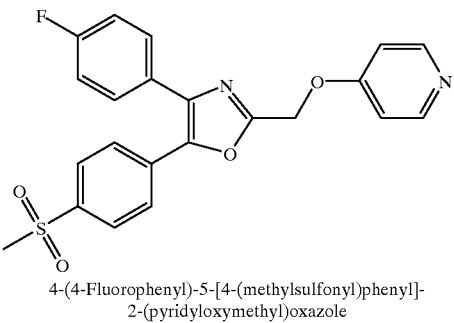

4-(4-Fluorophenyl)-5-[4-(methylsulfonyl)phenyl]-
2-(pyridyloxymethyl)oxazole 4-(4-Fluorophenyl)-5-[4-(methylsulfonyl)phenyl]-2-(pyridyloxymethyl)oxazole was prepared in a manner consistent with Example 28. Melting point: 276–278° C.

EXAMPLE 30

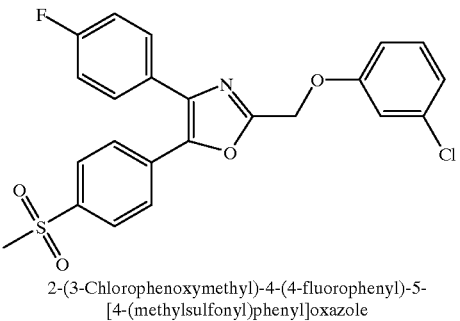

2-(3-Chlorophenoxymethyl)-4-(4-fluorophenyl)-5-
[4-(methylsulfonyl)phenyl]oxazole A solution containing 612 mg (1.44 mmol) of methyl [4-(4-fluorophenyl)-5-[4-(methylsulfonyl)phenyl]oxazol-2-yl]methanesulfonate (as prepared in Example 28) in 20 mL of DMF was stirred at 25° C. as 397 mg (2.88 mmol) of potassium carbonate and 0.3 mL (2.88 mmol) of 3-chlorophenol were added. The reaction was stirred for 2 days at 25° C. and poured into 100 mL of water. To this mixture was added 100 mL of ethyl acetate and the layers separated. The organic layer was washed with water, dried over sodium sulfate and concentrated in vacuo to give the crude solid which was purified by flash chromatography on a silica gel column using 50% ethyl acetate/hexane as the eluent to give 528 mg (80%) of a white solid which was recrystallized from 50% dichloromethane/isooctane to give a white crystalline solid (mp 112–114° C.) whose structure was assigned as 4-(4-fluorophenyl)-5-[4-(methylsulfonyl)phenyl]-2-(3-chlorophenoxy)methyloxazole on the basis of its spectral characteristics: $^1$H-NMR (CDCl$_3$, 300 MHz) δ 3.08 (s, 3H), 5.22 (s, 2H), 7.08 (m, 2H), 7.13 (m, 3H), 7.26 (m, 1H), 7.59 (dd, 2H, J=8.8, 5.4 Hz), 7.62 (dd, 2H, J=8.8, 5.4 Hz), 7.78 (d, 2H, J=8.8 Hz), 7.93 (d, 2H, J=8.8 Hz). $^{19}$F-NMR (CDCl$_3$, 280 MHz) δ −111.8. Analysis Calc'd. for C$_{23}$H$_{17}$NO$_4$FSCl: C, 60.33; H, 3.74; N, 3.06. Observed: C, 60.19; H, 3.80; N, 3.03.

EXAMPLE 31

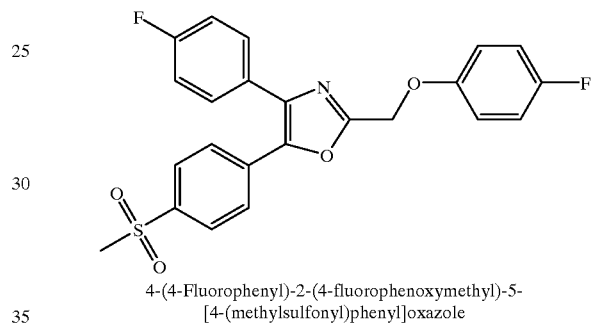

4-(4-Fluorophenyl)-2-(4-fluorophenoxymethyl)-5-
[4-(methylsulfonyl)phenyl]oxazole A solution containing 585 mg (1.37 mmol) of methyl [4-(4-fluorophenyl)-5-[4-(methylsulfonyl)phenyl]oxazol-2-yl]methanesulfonate (as prepared in Example 28) in 15 mL of DMF was stirred at 25° C. as 380 mg (2.74 mmol) of potassium carbonate and 308 mg (2.74 mmol) of 4-fluorophenol are added. The reaction was stirred for 2 days at 25° C. and poured into 100 mL of water. To this mixture was added 100 mL of ethyl acetate and the layers separated. The organic layer was washed with water, dried over sodium sulfate and concentrated in vacuo to give the crude solid which was purified by flash chromatography on a silica gel column using 50% ethyl acetate/hexane as the eluent to give 528 mg (80%) of a white solid which was recrystallized from 50% dichloromethane/isooctane to give a white crystalline solid (mp 133–134° C.) whose structure was assigned as 4-(4-fluorophenyl)-5-[4-(methylsulfonyl)-phenyl]-2-[(4-fluorophenoxy)methyl]oxazole on the basis of its spectral characteristics: $^1$H-NMR (CDCl$_3$, 300 MHz) δ 3.08 (s, 3H), 5.19 (S, 2H), 7.00 (m, 4H), 7.13 (m, 2H), 7.58 (dd, 2H, J=8.8, 5.2 Hz), 7.61 (dd, 2H, J=8.8, 5.2 Hz), 7.77 (d, 2H, J=8.7 Hz), 7.93 (d, 2H, J=8.7 Hz). $^{19}$F-NMR (CDCl$_3$, 280 MHz) δ −111.8, −122.5. Analysis Calc'd. for C$_{23}$H$_{17}$NO$_4$F$_2$S: C, 62.58; H, 3.88; N, 3.17. Observed: C, 62.44; H, 4.04; N, 3.11.

EXAMPLE 32

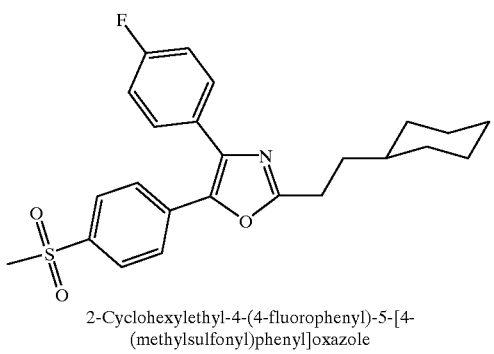

2-Cyclohexylethyl-4-(4-fluorophenyl)-5-[4-(methylsulfonyl)phenyl]oxazole

A solution containing 2.02 g (7.24 mmol) of 1-(4-fluorophenyl)-2-hydroxy-2-[4-(methylthiophenyl)ethanone in 100 mL of methylene chloride was stirred at 25° C. as 1.76 mL (21.72 mmol) of pyridine was added, followed by the addition of 1.52 g (8.69 mmol) of 2-cyclohexylpropionyl chloride. The reaction was stirred at 25° C. for 48 hours, after which the resulting yellow solution was washed with 1N HCl, dried over sodium sulfate and concentrated in vacuo. The crude solid was purified via flash chromatography on a silica gel column using 10% ethyl acetate/hexane as the eluent. This provided 2.87 g (96%) of a white foam, which was characterized as the benzoin ester on the basis of its NMR spectra: $^1$H-NMR (CDCl$_3$, 300 MHz) δ 0.80–0.96 (m, 2H), 1.10–1.25 (m, 4H), 1.45–1.78 (m, 7H), 2.40 (m, 2H), 2.43 (s, 3H), 6.75 (s, 1H), 7.05 (m, 2H), 7.23 (d, 2H, J=8 Hz), 7.35 (d, 2H, J=8 Hz) and 7.95 (m, 2H). $^{19}$F-NMR (CDCl$_3$, 280 MHz) δ −104.4.

A solution containing 2.87 g (6.92 mmol) of the benzoin ester and 5.3 g (69 mmol) of ammonium acetate in 100 mL of acetic acid was heated to 80° C. for 2 hours. The reaction was cooled to 25° C. and poured into water. The product was extracted into ethyl acetate and the combined organic extracts washed with an aqueous solution of sodium bicarbonate. The solution was dried over sodium sulfate and concentrated in vacuo to give the crude oxazole. This crude material was purified by flash chromatography on a silica gel column using 25% ethyl acetate/hexane as the eluent to give 1.87 g (68%) of a clear oil, which was characterized as 2-(2-cyclohexylethyl)-4-(4-fluorophenyl)-5-[4-(methythio)phenyl]oxazole on the basis of its spectral properties: $^1$H-NMR (CDCl$_3$, 400 MHz) δ 0.90–1.02 (m, 2H), 1.10–1.40 (m, 4H), 1.62–1.82 (m, 7H), 2.49 (s, 3H), 2.84 (t, J=8.0 Hz, 2H), 7.03 (d, J=8.7Hz, 1H), 7.06 (d, J=8.7Hz, 1H), 7.22 (d, J=8.6Hz, 2H), 7.45 (d, J=8.6Hz, 2H), 7.58 (d, J=5.4Hz, 1H), 7.61 (d, J=5.4Hz, 1H). The material from this experiment was used directly in the next step without further purification.

A solution of 1.87 g (4.73 mmol) of 2-(2-cyclohexylethyl)-4-(4-fluorophenyl)-5-[4-(methythio)phenyl]oxazole in 100 mL of methylene chloride was stirred at −78° C. as 3.26 g (9.46 mmol based on 50% purity) of m-chloroperoxybenzoic acid was added all at once. The reaction was stirred at −78° C. for 1 hour and TLC (silica, 50% hexane/ethyl acetate) indicated that the reaction mixture consisted of mostly sulfone. The reaction was poured into a solution of aqueous sodium metabisulfite. The aqueous solution was extracted using ethyl acetate and the organic layer was washed with saturated sodium metabisulfite, saturated sodium bicarbonate and brine. The resulting clear solution was dried over sodium sulfate and concentrated in vacuo to give a white solid which was purified by flash chromatography on a silica gel column using 50% ethyl acetate/hexane as the eluent. Recrystallization from 50% ethyl acetate/isooctane gave 1.76 g (87%) of a low melting semi-solid whose structure was assigned as 2-(2-cyclohexylethyl)-4-(4-fluorophenyl)-5-[4-(methylsulfonyl)phenyl]oxazole on the basis of its spectral characteristics: $^1$H-NMR (CDCl$_3$, 300 MHz) δ 0.90–1.06 (m, 2H), 1.11–1.40 (m, 7H), 2.87 (apparent t, J=8.1Hz, 2H), 3.07 (s, 3H), 7.10 (t, J=8.7Hz, 2H), 7.59 (m, 2H), 7.74 (d, J=8.7Hz, 2H), 7.90 (d, J=8.7Hz, 2H). $^{19}$F-NMR (CDCl$_3$, 280 MHz) δ −112.49. LRMS m/z 427 (M)+. HRMS Calc'd. for C$_{24}$H$_{26}$NO$_3$FS: 421.1617. Observed: 421.1611. Analysis Calc'd. for C$_{24}$H$_{26}$NO$_3$FS: C, 67.43; H, 6.13; N, 3.28. Observed: C, 67.27; H, 6.15; N, 3.24.

EXAMPLE 33

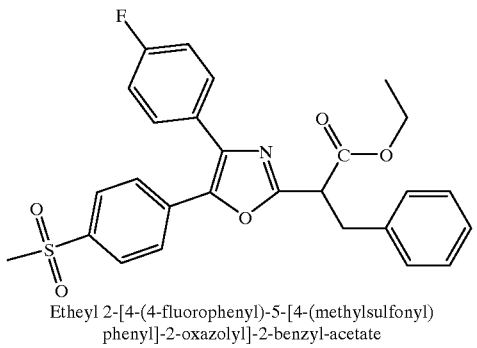

Etheyl 2-[4-(4-fluorophenyl)-5-[4-(methylsulfonyl)phenyl]-2-oxazolyl]-2-benzyl-acetate Step 1: Preparation of 2-(4-fluorophenyl)-3-(4-methylthiophenyl)propenoic acid Acetic anhydride (500 mL), 4-(methylthio)benzaldehyde (100.2 g, 0.66 mol), 4-fluorophenylacetic acid (101.6 g, 0.66 mol), and triethylamine (68.1 g, 0.67 mol) were placed in a 3 L round bottom flask and heated to reflux for 1.75 hours. The reaction was cooled to 110° C., and water (500 mL) was added cautiously through an addition funnel. This caused the solution to reflux vigorously and the temperature to rise to 135° C. A yellow precipitate formed, and after cooling to room temperature, was collected by filtration, washed with water, and recrystallized from ethyl acetate/isooctane to provide the diarylacrylic acid as yellow needles (135.2 g, 71%): mp 172–176° C. $^1$H NMR (acetone d$^6$) 300 MHz 7.84 (s, 1H), 7.03–7.28 (m, 10H), 2.46 (s, 3H). $^{19}$F NMR (acetone d$^6$) −116.11 (m). Mass spectrum M+ 288.

Step 2: Preparation of 1-(4-fluorophenyl)-2-(4-methylthiophenyl)ethanone

The diaryl acrylic acid (226.5 g, 0.78 mol) was placed in a 2 L round bottom flask with anhydrous toluene (800 mL) and triethylamine (81.2 g, 0.80 mol). After cooling to 0° C., diphenylphosphoryl azide (217.4 g, 0.79 mol) was added, the solution was stirred at 0° C. for 20 minutes and at room temperature for 2.50 hours. The reaction was poured into water, extracted with ether, dried over magnesium sulfate, and concentrated in vacuo to remove the ether. The remaining toluene solution was heated to reflux and a vigorous evolution of gas occurred. After 1.25 hours, tert-butyl alcohol (80 mL, 0.84 mol) was added to the reaction. After an additional 20 minutes, concentrated hydrochloric acid (41 mL) was added slowly causing the reaction to foam. The reaction was heated at 90° C. overnight (14 hours) and a white precipitate formed after cooling. The precipitate was isolated by filtration, washed with cold ether, and air dried to yield the desired intermediate (182.7 g, 89%): mp 134.5–138° C. $^1$H NMR (acetone d$^6$) 300 MHz 8.16 (m, 2H), 7.24 (m, 6H), 4.34 (s, 2H), 2.46 (s, 3H). $^{19}$F NMR (acetone d$^6$) −107.88 (m).

Step 3: Preparation of 1-(4-fluorophenyl)-2-(4-methylthiophenyl)-2-hydroxy-ethanone A 1 L three necked round bottomed flask equipped with reflux condenser, magnetic stir bar, thermometer adapter, and constant pressure addition funnel was charged with the intermediate from Step 2, (55.5 g, 0.21 mol), acetic acid (250 mL) and 33% HBr in acetic acid (120 mL). The solution was stirred and treated with bromine (11.1 mL, 0.21 mol) from the addition funnel at such a rate that the bromine color was discharged rapidly, ca. 15 minutes. After an additional 10 minutes at room temperature, the solution was filtered through a Buchner funnel and the filtrate concentrated in vacuo to give an orange solid. The crude bromoketone was dissolved in dichloromethane and washed with 1N NaHSO$_3$, dried over anhydrous MgSO$_4$, filtered and concentrated in vacuo to give 68.8 g of 1-(4-fluorophenyl)-2-(4-methylthiophenyl)-2-bromoethanone as a yellow solid which was used directly without further purification. The crude bromoketone was dissolved in 300 mL acetone and 150 mL of water and heated to reflux for 2.5 hours. The solution was concentrated in vacuo and the residue taken up in dichloromethane, washed with saturated aqueous sodium bicarbonate, brine, dried over anhydrous magnesium sulfate, filtered and reconcentrated in vacuo to give a light yellow solid that was crystallized from a mixture of dichloromethane and isooctane to provide 37.8 g (65%) of pure 1-(4-fluorophenyl)-2-(4-methylthiophenyl)-2-hydroxy-ethanone: mp 90–92° C.

Step 4: Preparation of ethyl 2-[4-(4-fluorophenyl)-5-[4-methylthiophenyl]]-2-oxazoleacetate A solution containing 8.00 g (29 mmol) of 1-(4-fluorophenyl)-2-hydroxy-2-[4-(methylthiophenyl)ethanone in 100 mL of methylene chloride was stirred at 25° C. as 7.0 mL (31 mmol) of pyridine was added, followed by the addition of 4.5 mL (35 mmol) of ethyl malonyl chloride. The reaction was stirred at 25° C. for 48 hours, after which the resulting yellow solution was washed with 1N HCl, dried over sodium sulfate and concentrated in vacuo. The crude solid was purified via flash chromatography on a silica gel column using 10% ethyl acetate/hexane as the eluent. This provided 7.31 g (64%) of a white foam, which was used directly without further purification. The product from above (7.31 g, 18.7 mmol) and 7.2 g of ammonium acetate (93.5 mmol, 5 equivalents) in 50 mL of glacial acetic were heated to reflux for 2 hours. The reaction mixture was cooled to 25° C. and poured into 100 mL of water. The aqueous solution was extracted with ethyl acetate and the combined organic extracts were washed with water and sodium bicarbonate solution, dried over sodium sulfate and concentrated in vacuo. The crude solid was purified by flash chromatography using a silica gel column and 20% ethyl acetate/hexane as the eluent to give a white solid which was recrystallized from 50% ethyl acetate/isooctane to give 5.55 g (80%) of a white solid whose structure was assigned as ethyl 2-[4-(4-fluorophenyl)-5-[4-methylthio)phenyl]oxazol-2-yl]acetate and was judged suitable for taking onto the next step.

Step 5: Preparation of ethyl 2-[4-(4-fluorophenyl)-5-[4-methylsulfonyl)phenyl]-2-oxazolyl]-2-benzyl-acetate A solution of 755 mg (2.03 mmol) of ethyl 2-[4-(4-fluorophenyl)-5-[4-methylthio)phenyl]oxazol-2-yl]acetate (from Step 4) was dissolved in 20 mL of anhydrous tetrahydrofuran (THF) and cooled to −78° C. and treated with a solution of potassium bid(trimethylsilyl)amide (2.44 mL, 1.2 equivalents, 1M in THF via syringe. The solution was maintained at −78° C. for 15 minutes and treated with a solution of 290 uL (2.44 mmol) of benzyl bromide. The solution was warmed to room temperature and poured into a saturated aqueous solution of ammonium chloride. The aqueous solution was extracted with ethyl acetate, washed with brine, dried over anhydrous sodium sulfate, filtered and concentrated in vacuo to give an oil that was purified by flash chromatography on silica gel eluting with 10% ethyl acetate/hexane to provide 396 mg of the dialkylated product and 182 mg (19%) of ethyl 2-[4-(4-fluorophenyl)-5-[4-methylthio)phenyl]oxazol-2-yl]-1-benzyl-acetate that was used directly in the next step. A solution of 182 mg (0.344 mmol) of ethyl 2-[4-(4-fluorophenyl)-5-[4-methylthio)phenyl]oxazol-2-yl]-1-benzyl-acetate in 5 mL of dichloromethane was cooled to −78° C. and treated with 272 mg (2 equivalents) of m-chloroperoxybenzoic acid for 2 hours. The reaction was poured into a solution of aqueous sodium metabisulfite. The aqueous solution was extracted using ethyl acetate and the organic layer was washed with saturated sodium metabisulfite, saturated sodium bicarbonate and brine. The resulting clear solution was dried over sodium sulfate and concentrated in vacuo to give a transparent oil which was purified by flash chromatography on a silica gel column using 30% ethyl acetate/hexane as the eluent. The purified material was an oil whose structure was assigned as ethyl 2-[4-(4-fluorophenyl)-5-[4-methylsulfonyl)phenyl]oxazol-2-yl]-2-benzyl-acetate on the basis of its spectral characteristics: $^1$H-NMR (CDCl$_3$, 300 MHz) δ 1.20 (t, J=7.0Hz, 3H), 3.07 (s, 3H), 3.53 (m, 2H), 4.19 (q, J=7.0Hz, 2H), 4.23 (m, 1H), 7.10 (d, J=8.7Hz, 2H), 7.25 (m, 5H), 7.57 (m, 2H), 7.70 (d, J=8.7Hz, 2H), 7.90 (d, J=8.7Hz, 2H). $^{19}$F-NMR (CDCl$_3$, 280 MHz) δ −112.15. LRMS m/z 493 (M)+. HRMS Calc'd. for $C_{27}H_{24}NO_5FS$: 493.1359. Observed: 493.1371.

EXAMPLE 34

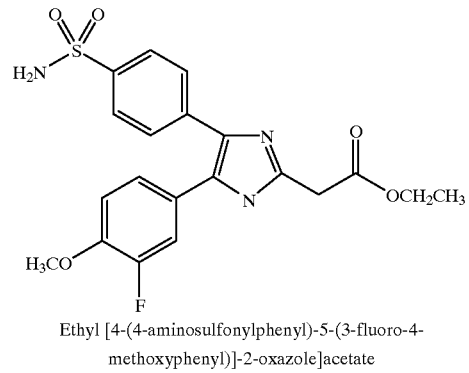

Ethyl [4-(4-aminosulfonylphenyl)-5-(3-fluoro-4-methoxyphenyl)]-2-oxazole]acetate Step 1. Preparation of 2-hydroxy-2-(3-fluoro-4-methoxyphenyl)-1-phenylethanone A solution of 3-fluoro-para-anisaldehyde (25.00 g, 162 mmol) and zinc iodide (0.27 g) in dichloromethane (100 mL) was treated with a solution of trimethylsilylcyanide (22 mL, 165 mmol) in dichloromethane (20 mL). The solution was stirred for 0.4 hours at room temperature, washed with saturated NaHCO$_3$, dried over MgSO$_4$, and concentrated in vacuo to give the trimethylsilyl cyanohydrin as an orange oil (37.83 g). The trimethylsilyl-cyanohydrin was dissolved in diethyl ether (50 mL) and added dropwise to a solution of phenylmagnesium bromide (174 mmol) in diethyl ether (658 mL) while maintaining the temperature between 25–35° C. with an ice water bath. The reaction was stirred for 0.4 hours at room temperature then quenched by adding 3N HCl. The reaction mixture was extracted with ethyl acetate, washed with saturated NaHCO₃ and brine, dried over MgSO₄, and concentrated in vacuo to give an orange oil (39.57 g). The orange oil was dissolved in 9:1 trifluoroacetic acid/water (80 mL) and stirred for 1.4 hours at room temperature. The reaction was neutralized with solid sodium carbonate, extracted with ethyl acetate, washed with 10% Na₂CO₃ and brine, dried over MgSO₄, and concentrated in vacuo to give a brown solid which was recrystallized from diethyl ether/hexane to give the benzoin (13.87 g, 33%): mp 76–79° C. ¹H NMR (CDCl₃) 300 MHz δ 7.89 (d, J=7.3 Hz, 2H) 7.55 (m, 1H) 7.42 (m, 2H) 7.05 (m, 2H) 6.90 (m, 1H) 5.88 (br d, J=3.0 Hz, 1H) 4.50 (br d, 1H). ¹⁹F NMR (CDCl₃) 282 MHz −134.05 (m).

Step 2. Esterification of 2-hydroxy-2-(3-fluoro-4-methoxyphenyl)-1-phenylethanone A solution of benzoin from Step 1 (3.25 g, 12.5 mmol), pyridine (4.94 g, 62.5 mmol), and ethyl malonyl chloride (2.38 g, 15.8 mmol) in dichloromethane (20 mL) was stirred for 94 hours at room temperature. The reaction mixture was washed with 3N HCl, saturated NaHCO₃ and water, dried over MgSO₄, concentrated in vacuo and passed through a column of silica gel eluting with 25% ethyl acetate/hexane to give a yellow oil (1.93 g, 41%): ¹H NMR (CDCl₃) 300 MHz δ 7.89 (d, J=7.7 Hz, 2H) 7.53 (m, 1H) 7.41 (m, 2H) 7.16 (m, 2H) 6.92 (m, 1H) 6.84 (s, 1H) 4.50 (q, J=7.0 Hz, 2H) 3.85 (d, J=1.0 Hz, 3H) 3.52 (s, 2H) 1.25 (t, J=7.0 Hz, 3H). ¹⁹F NMR (CDCl₃) 282 MHz −133.67 (m). Mass spectrum: M+Li=381.

Step 3. Preparation of ethyl [4-phenyl-5-(3-fluoro-4 methoxyphenyl)]-2-oxazoleacetate.

The ketone from the Step 2 (1.83 g, 4.9 mmol) was dissolved in acetic acid (25 mL), treated with ammonium acetate (3.86 g, 50.0 mmol), and heated to reflux for 2.0 hours. The reaction mixture was diluted with ethyl acetate, washed with water, saturated NaHCO₃, and brine, dried over MgSO₄, concentrated in vacuo, and passed through a column of silica gel eluting with 16% ethyl acetate/hexane to give a yellow solid (0.67 g, 39%): mp 85–86° C. ¹H NMR (CDCl₃) 300 MHz δ 7.61 (d, J=7.5 Hz, 2H) 7.35 (m, 5H) 6.93 (m, 1H) 4.24 (q, J=7.1 Hz, 2H) 3.93 (s, 2H) 3.91 (s, 3H) 1.30 (t, J=7.1 Hz, 3H). ¹⁹F NMR (CDCl₃) 282 MHz δ 134.77 (m). High resolution mass spectrum Calc'd. for C₂₀H₁₈FNO₄: 356.1298. Found: 356.1303.

Step 4. Preparation of ethyl [4-(4-aminosulfonylphenyl)-5-(3-fluoro-4-methoxyphenyl)]-2-oxazoleacetate The compound from Step 3 (0.63 g, 1.8 mmol) was stirred with chlorosulfonic acid (15 mL) for 1.1 hours at 5° C. The reaction mixture was slowly added to ice water, and extracted with dichloromethane. The dichloromethane solution was stirred at 5° C. with ammonium hydroxide for 3.0 hours. The organic layer was collected, washed with 3N HCl, dried over MgSO₄, concentrated in vacuo, and the residue recrystallized from ethyl acetate/hexane to give a white solid (0.02 g, 2.6%): mp 127–130° C. ¹H NMR (acetone-d₆) 300 MHz δ 7.90 (d, J=8.7 Hz, 2H) 7.84 (d, J=8.7 Hz, 2H) 7.38 (m, 2H) 7.26 (m, 1H) 6.64 (br s, 1H) 4.20 (q, J=7.0 Hz, 2H) 4.01 (s, 2H) 3.95 (s, 3H) 1.27 (t, J=7.0 Hz, 3H). ¹⁹F NMR (acetone-d₆) 282 MHz −135.76 (m). High resolution mass spectrum Calc'd. for C₂₀H₂₀F₁N₂O₆S1: 435.1026. Found: 435.1036.

EXAMPLE 35

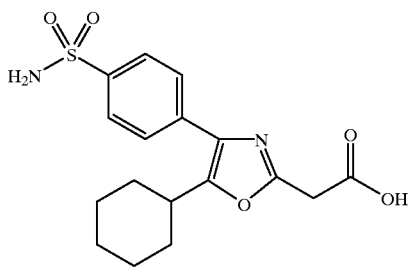

[4-(4-Aminosulfonylphenyl)-5-cyclohexyl]-2-oxazoleacetic acid

Step 1. Preparation of 2-hydroxy-2-cyclohexyl-1-phenylethanone

A solution of cyclohexanecarboxaldehyde (8.5 g, 76 mmol) and zinc iodide (0.11 g) in dichloromethane (40 mL) was treated with a solution of trimethylsilylcyanide (10 mL, 76 mmol) in dichloromethane (20 mL). The solution was stirred for 0.33 hours at room temperature, washed with water and saturated NaHCO₃, dried over MgSO₄, and concentrated in vacua to give the trimethylsilyl cyanohydrin as an orange oil (13.02 g). The trimethylsilyl cyanohydrin was dissolved in diethyl ether (50 mL) and added dropwise to a solution of phenylmagnesium bromide (54 mmol) in diethyl ether (268 mL) while maintaining the temperature between 25–35° C. with an ice water bath. The reaction was stirred for 0.67 hours at room temperature then quenched by adding 3N HCl (60 mL). The organic layer was collected, washed with saturated NaHCO₃ and brine, dried over MgSO₄, and concentrated in vacuo to give a white solid (12.96 g). The white solid was dissolved in 9:1 trifluoroacetic acid/water (50 mL) and stirred for 2.0 hours at room temperature. The reaction was neutralized with solid sodium carbonate, extracted with ethyl acetate, washed with saturated NaHCO₃ and brine, dried over MgSO₄, concentrated in vacuo and recrystallized from diethyl ether/hexane to give the benzoin (2.55 g, 25%): mp 87–92° C. ¹H NMR (CDCl₃) 300 MHz δ 7.88 (d, J=7.1 Hz, 2H) 7.62 (m, 1H) 7.50 (m, 2H) 4.93 (d, J=2.2 Hz 1H) 3.60 (br s, 1H) 1.52–1.82 (m, 6H) 1.02 1.24 (m, 5H). Mass spectrum: M+Li=225.

Step 2. Esterification of 2-hydroxy-2-cyclohexyl-1-phenylethanone

The ethanone of Step 1 (2.55 g, 11.7 mmol) was dissolved in THF (10 mL), 2,2-dimethyl-1,3-dioxane-4,6-dione (1.73 g, 12.0 mmol) was added and the reaction was heated to reflux for 17.3 hours. The reaction mixture was partitioned between saturated NaHCO₃ and diethyl ether. The aqueous layer was acidified with concentrated HCl, extracted with diethyl ether, washed with brine, dried over MgSO₄, and concentrated in vacuo to give a yellow oil (2.26 g) which was used in the next step without further purification.

Step 3. Preparation of 2-carboxymethyl-4-hydroxy-4-phenyl-5-cyclohexyloxazoline

The ethanone from the Step 2 (1.87 g, 6.1 mmol) was dissolved in ethanol (20 mL), treated with ammonium acetate (4.94 g,16.3 mmol), and heated to reflux for 4.3 hours. The reaction mixture was concentrated in vacuo, and the residue was partitioned between saturated NaHCO₃ and ethyl acetate. The aqueous layer was acidified with 3N HCl, extracted with diethyl ether, washed with brine, dried over MgSO₄, and concentrated in vacuo dissolved in ethyl acetate, washed with water, saturated NaHCO₃, and brine, dried over MgSO₄, and concentrated in vacuo to give a white solid (0.75 g, 43%): mp 151–155° C. dec. Mass spectrum: M+Li=310.

Step 4. Preparation of [4-(4-aminosulfonylphenyl)-5-cyclohexyl]-2-oxazoleacetic acid The compound from Step 3 (0.47 g, 1.6 mmol) was stirred with chlorosulfonic acid (2.5 mL) for 1.25 hours at 5° C. The reaction mixture was slowly added to ice water, and extracted with dichloromethane. The dichloromethane was stirred at room temperature with ammonium hydroxide (20 mL) for 23.1 hours. The aqueous layer was collected, acidified with concentrated HCl, and filtered to give a white solid (0.17 g, 28%): mp 223–230° C. $^1$H NMR (acetone-$d_6$) 300 MHz δ 7.95 (d, 2H) 7.85 (d, 2H) 6.60 (br s, 2H) 3.90 (s, 2H) 3.20 (m, 1H) 1.20–1.95 (m, 10H). High resolution mass spectrum Calc'd. for $C_{17}H_{21}N_2O_5S$: 365.1171. Found: 365.1187.

EXAMPLE 36

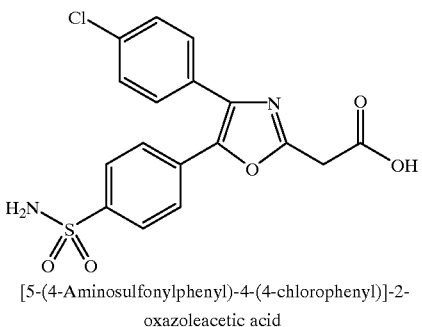

[5-(4-Aminosulfonylphenyl)-4-(4-chlorophenyl)]-2-oxazoleacetic acid

Step 1. Preparation of 2-hydroxy-2-phenyl-1-(4-chlorophenyl)ethanone

The trimethylsilyl cyanohydrin of benzaldehyde, prepared similar to that described in Example 34, Step 1, (10.18 g, 50 mmol) was dissolved in diethyl ether (10 mL) and added dropwise to a solution of 4-chlorophenylmagnesium bromide (59 mmol) in diethyl ether (319 mL) while maintaining the temperature between 23–35° C. with an ice water bath. The reaction was stirred for 1.2 hours at room temperature then quenched by adding 3N HCl (50 mL). The organic layer was collected, washed with saturated NaHCO$_3$ and brine, dried over MgSO$_4$, and concentrated in vacuo to give a yellow oil (15.57 g). The yellow oil was dissolved in 9:1 trifluoroacetic acid/water (30 mL) and stirred for 1.75 hours at room temperature. The reaction was neutralized with solid sodium carbonate, extracted with ethyl acetate, washed with 10% Na$_2$CO$_3$ and brine, dried over MgSO$_4$, concentrated in vacuo and recrystallized from diethyl ether/hexane to give the benzoin (5.76 g, 47%): mp 87–92° C.

Step 2. Esterification of 2-hydroxy-2-phenyl-1-(4-chlorophenyl)ethanone

The ethanone from Step 1 (4.28 g,17.3 mmol) was dissolved in THF (15 mL), 2,2 dimethyl-1,3-dioxane-4,6-dione (2.52 g, 17.5 mmol) was added and the reaction heated to reflux for 15.7 hours. The reaction mixture was partitioned between saturated NaHCO$_3$ and diethyl ether. The aqueous layer was acidified with concentrated HCl, extracted with diethyl ether, washed with brine, dried over MgSO$_4$, and concentrated in vacuo to give a yellow oil (4.55 g) which was used in the next step without further purification: Mass spectrum: M+Li=339.

Step 3. Preparation of [4-(4-chlorophenyl)-5-phenyl]-2-oxazoleacetic acid

The ester from Step 2 (4.69 g, 14.1 mmol) was dissolved in ethanol (20 mL), treated with ammonium acetate (10.87 g, 141.0 mmol), and heated to reflux for 4.75 hours. The ethanol was removed in vacuo and the residue was dissolved in water, acidified with 3N HCl, precipitated with diethyl ether and hexane and filtered to give an orange solid (2.71 g, 61%): mp 158–160° C. $^1$H NMR (DMSO-$d_6$) 300 MHz δ 14.8 (br s, 1H) 7.48 (m, 9H) 4.19 (s, 2H).

Step 4. Preparation of [5-(4-aminosulfonylphenyl)-4-(4-chlorophenyl)]-2-oxazoleacetic acid The compound from Step 3 (1.71 g, 5.4 mmol) was stirred with chlorosulfonic acid (7 mL) for 1.25 hours at 5° C. The reaction mixture was added to ice water, and extracted with dichloromethane. The dichloromethane was stirred with ammonium hydroxide (30 mL) for 1.2 hours at room temperature. The aqueous layer was collected and acidified with concentrated HCl, extracted with ethyl acetate, dried over MgSO$_4$, and concentrated in vacuo to give a white solid (0.11 g, 5%): $^1$H NMR (DMSO-$d_6$) 300 MHz δ 13.5 (br s, 1H) 7.81 (d, J=8.5 Hz, 2H) 7.62 (d, J=8.3 Hz, 2H) 7.47 (m, 6H) 3.90 (s, 2H)

EXAMPLE 37

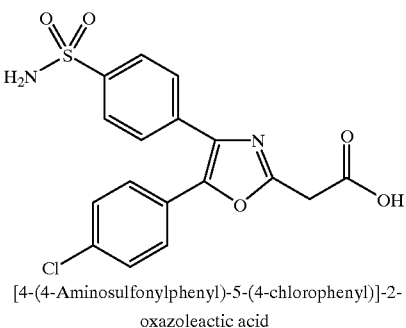

[4-(4-Aminosulfonylphenyl)-5-(4-chlorophenyl)]-2-oxazoleactic acid

Step 1. Preparation of 2-hydroxy-2-(4-chlorophenyl)-1-phenylethanone.

A solution of 4-chlorobenzaldehyde (9.86 g, 70 mmol) and zinc iodide (0.18 g) in dichloromethane (40 mL) was treated with a solution of trimethylsilylcyanide (9 mL, 71 mmol) in dichloromethane (20 mL). The solution was stirred for 0.33 hours at room temperature, washed with water and saturated NaHCO$_3$, dried over MgSO$_4$, and concentrated in vacuo to give the trimethylsilyl cyanohydrin as an orange oil (13.90 g). The trimethylsilyl cyanohydrin was dissolved in diethyl ether (50 mL) and added dropwise to a solution of phenylmagnesium bromide (69 mmol) in diethyl ether (269 mL) while maintaining the temperature between 15–28° C. with an ice water bath. The reaction was stirred for 0.75 hours at room temperature then quenched by adding 3N HCl (50 mL). The organic layer was collected, washed with saturated NaHCO$_3$ and brine, dried over MgSO$_4$, and concentrated in vacuo to give a yellow solid (13.06 g). The yellow solid was dissolved in 9:1 trifluoroacetic acid/water (30 mL) and stirred for 1.6 hours at room temperature. The reaction was neutralized with solid sodium carbonate, extracted with ethyl acetate, washed with 10% Na$_2$CO$_3$ and brine, dried over MgSO$_4$, concentrated in vacuo to give a yellow solid (9.43 g) and used in the next step without further purification.

Step 2. Esterification of 2-hydroxy-2-(4-chlorophenyl)-1-phenylethanone

The ethanone from Step 1 (4.34 g, 17.6 mmol) was dissolved in THF (40 mL), 2,2 dimethyl-1,3-dioxane-4,6-dione (2.56 g, 17.8 mmol) was added and the reaction heated to reflux for 18.3 hours. The reaction mixture was partitioned between saturated NaHCO$_3$ and diethyl ether. The aqueous layer was acidified with concentrated HCl, extracted with diethyl ether, washed with brine, dried over MgSO$_4$, and concentrated in vacuo to give a yellow oil (4.66 g, 68%): $^1$H NMR (CDCl$_3$) 300 MHz δ 7.89 (d, J=8.5 Hz, 2H) 7.54 (m, 1H) 7.35 (m, 6H) 6.90 (s, 1H) 3.59 (s, 2H). Mass spectrum M+Li=339.

Step 3. Preparation of [5-(4-chlorophenyl)-4-phenyl]-2-oxazoleacetic acid

The ester from Step 2 (2.88 g, 12.4 mmol) was dissolved in ethanol (20 mL), treated with ammonium acetate (6.74 g, 87.4 mmol), and heated to reflux for 4.1 hours. The reaction mixture was concentrated in vacuo, and the residue was partitioned between water and diethyl ether. The aqueous layer was acidified with 3N HCl, allowed stand at room temperature then filtered to give a white solid (0.75 g, 28%): mp 212.5–219° C. Mass spectrum: M+=313.

Step 4. Preparation of [4-(4-aminosulfonylphenyl)-5-(4-chlorophenyl)]-2-oxazoleacetic acid The compound from Step 3 (0.71 g, 2.3 mmol) was stirred with chlorosulfonic acid (7 mL) at 5° C. for 1.0 hour. The reaction mixture was added to ice water, and extracted with dichloromethane. The dichloromethane was stirred with ammonium hydroxide for 1.3 hours at room temperature. The aqueous layer was collected and acidified with concentrated HCl, extracted with ethyl acetate, dried over MgSO$_4$, and concentrated in vacuo to give a white solid (0.18 g, 20%): mp 118–120° C. (dec). $^1$H NMR (DMSO-d$_6$) 300 MHz δ 7.86 (d, J=8.3 Hz, 2H) 7.66 (d, J=8.5 Hz, 2H) 7.56 (m, 4H) 4.15 (s, 2H).

EXAMPLE 38

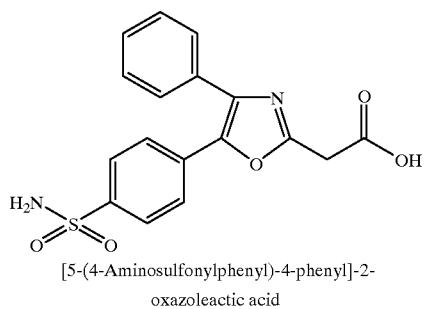

[5-(4-Aminosulfonylphenyl)-4-phenyl]-2-oxazoleactic acid

Step 1. Esterification of benzoin

Benzoin (33.32 g, 157 mmol) was dissolved in THF (65 mL), 2,2-dimethyl-1,3-dioxane-4,6-dione (22.85 g, 159 mmol) was added and the reaction heated to reflux for 22.6 hours. The reaction mixture was partitioned between saturated NaHCO$_3$ and ethyl acetate. The aqueous layer was acidified with concentrated HCl, extracted with diethyl ether, dried over MgSO$_4$, and concentrated in vacuo to give a yellow oil (35.08 g) which was used in the next step without further purification.

Step 2. Preparation of ethyl [4-hydroxy-4,5-diphenyl-2-oxazolinyl]acetate.

The compound from step 1 (2.26 g, 7.6 mmol) was dissolved in methanol (25 mL), treated with ammonium acetate (1.26 g, 16.3 mmol), and heated to reflux. After 1.8 hours, the reaction was cooled, acidified by adding concentrated sulfuric acid and heated to reflux for an additional 2.0 hours. The reaction mixture was concentrated in vacuo, and the residue was dissolved in ethyl acetate, washed with water, saturated NaHCO$_3$, and brine, dried over MgSO$_4$, and concentrated in vacuo to give an orange oil (1.50 g) which was used in the next step without further purification.

Step 3. Preparation of ethyl [5-(4-aminosulfonylphenyl)-4-phenyl]-2-oxazoleacetate.

The compound from Step 2 (1.32 g, 4.2 mmol) was stirred with chlorosulfonic acid (13 mL) for 1.25 hours at 5° C. The reaction mixture was slowly added to ice water, and extracted with dichloromethane. The dichloromethane was stirred with ammonium hydroxide (40 mL) for 1.9 hours at 5° C. The organic layer was collected, washed with 3N HCl, dried over MgSO$_4$, concentrated in vacuo, and passed through a column of silica gel eluting with 40% ethyl acetate/hexane to give a white solid (0.30 g, 19%): mp 84–88° C. $^1$H NMR (acetone-d$_6$) 300 MHz δ 7.92 (d, J=8.5 Hz, 2H) 7.77 (d, J=8.5 Hz, 2H) 7.63 (m, 2H) 7.41 (m, 3H) 6.71 (br s, 2H) 4.06 (s, 2H) 3.74 (s, 3H). High resolution mass spectrum Calc'd. for C$_{18}$H$_{17}$N$_2$O$_5$S: 373.0858. Found: 373.0833.

Step 4. Preparation of [5-(4-aminosulfonylphenyl)-4-phenyl]-2-oxazoleacetic acid The oxazole ester from Step 3 (0.65 g, 1.7 mmol) was dissolved in methanol (10 mL), treated with NaOH (0.09 g dissolved in 5 mL water, 2.2 mmol), and stirred at room temperature. After 0.33 hours, additional NaOH (0.10 g, 2.5 mmol) was added and stirring continued for 0.4 hours. Water was added and the reaction mixture was extracted with ethyl acetate. The aqueous layer was acidified with concentrated HCl and extracted with ethyl acetate. The ethyl acetate was washed with brine, dried over MgSO$_4$, and concentrated in vacuo to give a yellow solid (0.43 g, 69%): mp 134–137° C. (dec). $^1$H NNR (acetone-d$_6$) 300 MHz δ 7.92 (d, J=8.5 Hz, 2H) 7.78 (d, J=8.7 Hz, 2H) 7.64 (m, 2H) 7.42 (m, 3H) 6.68 (br s, 1H) 4.03 (s, 2H). High resolution mass spectrum Calc'd. for C$_{17}$H$_{15}$N$_2$O$_5$S: 359.0702. Found: 359.0722.

EXAMPLE 39

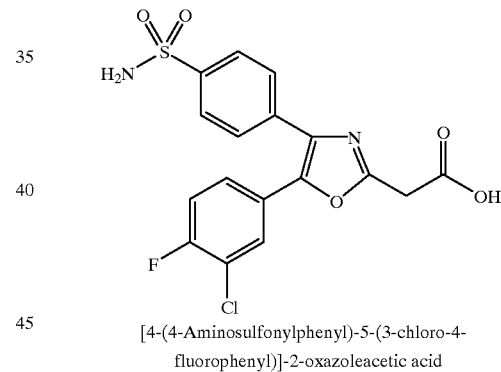

[4-(4-Aminosulfonylphenyl)-5-(3-chloro-4-fluorophenyl)]-2-oxazoleacetic acid

Step 1. Preparation of 2-hydroxy-2-(3-chloro-4-fluorophenyl)-1-phenylethanone.

A solution of 3-chloro-4-fluorobenzaldehyde (14.00 g, 89 mmol) and zinc iodide (0.16 g) in dichloromethane (50 mL) was treated with a solution of trimethylsilylcyanide (12 mL, 90 mmol) in dichloromethane (15 mL). The solution was stirred for 0.5 hours at room temperature, washed with saturated NaHCO$_3$ and brine, dried over MgSO$_4$, and concentrated in vacuo to give the trimethylsilyl cyanohydrin as an orange oil (20.18 g). The trimethylsilyl cyanohydrin was dissolved in diethyl ether (20 mL) and added dropwise to a solution of phenylmagnesium bromide (90 mmol) in diethyl ether (200 mL) while maintaining the temperature between 25–33° C. with an ice water bath. The reaction was stirred for 0.6 hours at room temperature then quenched by adding 3N HCl (90 mL). The organic layer was collected, washed with saturated NaHCO$_3$ and brine, dried over MgSO$_4$, and concentrated in vacuo to give the an orange oil (24.13 g). The orange oil was dissolved in 9:1 trifluoroacetic acid/ water (100 mL) and stirred for 1.5 hours at room temperature. The reaction was neutralized with solid sodium carbonate, extracted with diethyl ether, washed with saturated NaHCO$_3$ and brine, dried over MgSO$_4$, and concentrated in vacuo to give a brown solid which was recrystallized from diethyl ether/hexane to give the benzoin (9.78 g, 41%): mp 58–63° C. $^1$H NMR (CDCl$_3$) 300 MHz δ 7.88 (d, J=7.0 Hz, 2H) 7.57 (m, 1H) 7.44 (m, 3H) 7.20 (m, 1H) 7.08 (t, J=8.7 Hz, 1H) 5.92 (s, 1H) 4.60 (br s, 1H). $^{19}$F NMR (CDCl$_3$) 282 MHz –115.88 (m).

Step 2. Esterification of 2-hydroxy-2-(3-chloro-4-fluorophenyl)ethanone

The ketone from Step 1 (5.54 g, 20.9 mmol) was dissolved in THF (5 mL), 2,2 dimethyl-1,3-dioxane-4,6-dione (4.65 g, 32.2 mmol) was added and the reaction heated to reflux for 17.2 hours. The reaction mixture was partitioned between saturated NaHCO$_3$ and diethyl ether. The aqueous layer was acidified with concentrated HCl, extracted with diethyl ether, washed with brine, dried over MgSO$_4$, and concentrated in vacuo to give a brown oil (6.94 g) which was used in the next step without further purification.

Step 3. Preparation of methyl [5-(3-chloro-4-fluorophenyl)-4-hydroxy-4-phenyl-2-oxazolinyl]acetate.

A solution of the ester from Step 2 (6.86 g, 19.6 mmol) dissolved in methanol (11 mL) was treated with ammonium acetate (3.17 g, 41.1 mmol), and heated to reflux. After 1.9 hours, the reaction was cooled, additional methanol (65 mL) was added, and the reaction mixture was acidified by adding concentrated sulfuric acid and heated to reflux for an additional 1.4 hours. The reaction mixture was concentrated in vacuo, and the residue was dissolved in ethyl acetate, washed with water, saturated NaHCO$_3$, and brine, dried over MgSO$_4$, concentrated in vacuo, and passed through a column of silica gel eluting with 50% ethyl acetate/hexane to give a yellow oil (2.10 g, 29%): $^1$H NMR (acetone-d$_6$) 300 MHz δ 8.30 (br s, 1H) 8.18 (dd, J=7.3 Hz 2.2 Hz, 1H) 8.12 (m, 1H) 7.30–7.50 (m, 6H) 6.60 (d, J=6.8 Hz, 1H) 3.65 (S, 3H) 3.41 (s, 2H). $^{19}$F NMR (acetone-d$_6$) 282 MHz –109.78 (m). Mass spectrum: M+Li=370.

Step 4. Preparation of methyl [4-(4-aminosulfonylphenyl)-5-(3-chloro-4-fluorophenyl)]-2-oxazoleacetate The compound from Step 3 (2.05 g, 5.6 mmol) was stirred with chlorosulfonic acid (10 mL) for 0.33 hours at room temperature and then for 0.25 hours at 75° C. The reaction was cooled, slowly added to ice water, and extracted with dichloromethane. The dichloromethane layer was stirred with ammonium hydroxide for one hour at room temperature. The organic layer was concentrated in vacuo, dissolved in ethyl acetate, washed with 3N HCl, brine, dried over MgSO$_4$, concentrated in vacuo and recrystallized from ethyl acetate/hexane to give a white solid (0.58 g, 24%): mp 142–144° C. $^1$H NMR (acetone-d$_6$) 300 MHz δ 7.92 (d, J=8.5 Hz, 2H) 7.85 (d, J=8.7 Hz, 2H) 7.78 (dd, J=7.1 Hz 2.2 Hz, 1H) 7.62 (m, 1H) 7.44 (t, J=8.8 Hz, 1H) 6.66 (br s, 1H) 4.06 (s, 2H) 3.75 (s, 3H). $^{19}$F NMR (acetone-d$_6$) 282 MHz –115.94 (m). High resolution mass spectrum Calc'd. for C$_{18}$H$_{15}$ClFN$_2$O$_5$S: 425.0374. Found: 425.0379.

Step 5. Preparation of [4-(4-aminosulfonylphenyl)-5-(3-chloro-4-fluorophenyl)]-2-oxazoleacetic acid The ester from Step 4 (0.55 g, 1.3 mmol) was dissolved in methanol (10 mL), treated with NaOH (0.09 g dissolved in 5 mL water, 2.2 mmol), and stirred at room temperature. After 1 hour, additional NaOH (0.10 g, 2.5 mmol) was added and stirring was continued for 1.4 hours. Water was added and the reaction mixture was extracted with ethyl acetate. The aqueous layer was then acidified with concentrated HCl and extracted with ethyl acetate.

The ethyl acetate was washed with brine, dried over MgSO$_4$, and concentrated in vacuo to give a white solid (0.39 g, 74%): mp 222–223° C. $^1$H NMR (acetone-d$_6$) 300 MHz δ 7.92 (d, J=8.5 Hz, 2H) 7.85 (d, J=8.6 Hz, 2H) 7.79 (dd, J=7.0 Hz 2.2 Hz, 1H) 7.62 (m, 1H) 7.44 (t, J=8.9 Hz, 1H) 6.67 (br s, 1H) 4.04 (s, 2H). $^{19}$F NMR (acetone-d$_6$) 282 MHz –116.41 (m).

EXAMPLE 40

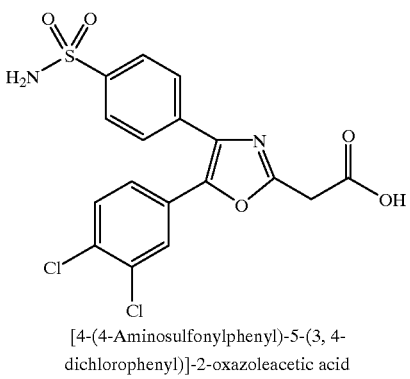

[4-(4-Aminosulfonylphenyl)-5-(3, 4-dichlorophenyl)]-2-oxazoleacetic acid

Step 1. Preparation of 2-hydroxy-2-(3,4-dichlorophenyl)-1-phenylethanone.

A solution of 3,4-dichlorobenzaldehyde (25.35 g, 145 mmol) and zinc iodide (0.42 g) in dichloromethane (100 mL) was treated with a solution of trimethylsilylcyanide (20 mL, 150 mmol) in dichloromethane (25 mL). The solution was stirred for 0.33 hours at room temperature, washed with saturated NaHCO3 and brine, dried over MgSO$_4$, and concentrated in vacuo to give the trimethylsilyl cyanohydrin as an orange oil (36.79 g). The trimethylsilyl cyanohydrin was dissolved in diethyl ether (50 mL) and added dropwise to a solution of phenylmagnesium bromide (144 mmol) in diethyl ether (500 mL) while maintaining the temperature between 25–33° C. with an ice water bath. The reaction was allowed to stir for 1.8 hours at room temperature then quenched by adding 3N HCl (160 mL). The organic layer was collected, washed with saturated NaHCO$_3$ and brine, dried over MgSO$_4$, and concentrated in vacuo to give an orange oil (49.07 g). The orange oil was dissolved in 9:1 trifluoroacetic acid/water (100 mL) and stirred for 1.5 hours at room temperature. The reaction was neutralized with solid sodium carbonate, extracted with diethyl ether, washed with brine, dried over MgSO$_4$, and concentrated in vacuo to give a yellow solid which was recrystallized from ethyl acetate/iso-octane to give the benzoin (16.35 g, 37%): mp 68–71° C. $^1$H NMR (CDCl$_3$) 300 MHz δ 7.88 (d, J=7.5 Hz, 2H) 7.57 (m, 1H) 7.44 (m, 3H) 7.37 (d, J=8.3 Hz, 1H) 7.07 (dd, J=8.3 Hz 2.0 Hz, 1H) 5.92 (s, 1H) 4.60 (br s, 1H).

Step 2. Esterification of 2-hydroxy-2-(3,4-dichlorophenyl)-1-phenylethanone

The ketone from Step 1 (7.43 g, 26.4 mmol) was dissolved in THF (8 mL), 2,2-dimethyl-1,3 dioxane-4,6-dione (5.92 g, 41.1 mmol) was added and the reaction heated to reflux for 19.9 hours. The reaction mixture was partitioned between saturated NaHCO$_3$ and diethyl ether. The aqueous layer was acidified with concentrated HCl, extracted with diethyl ether, washed with brine, dried over MgSO$_4$, and concentrated in vacuo to give a brown oil (6.67 g) which was used in the next step without further purification.

Step 3. Preparation of methyl [5-(3,4-dichlorophenyl)-4-hydroxy-4-phenyl-2-oxazolinyl]acetate The ester from Step 2 (6.67 g, 18.2 mmol) was dissolved in methanol (10 mL), treated with ammonium acetate (2.90 g, 37.6 mmol), and heated to reflux. After 2.0 hours, the reaction was cooled, additional methanol (50 mL) was added, and the reaction mixture was acidified by adding concentrated sulfuric acid and heated to reflux for an additional 0.6 hours. The reaction mixture was concentrated in vacuo, and the residue was dissolved in ethyl acetate, washed with water, saturated NaHCO$_3$, and brine, dried over MgSO$_4$, and concentrated in vacuo to give an orange oil (4.38 g) which was used in the next step without further purification.

Step 4. Preparation of methyl [4-(4-aminosulfonylphenyl)-5-(3,4-dichlorophenyl)]-2-oxazoleacetate.

The compound from Step 3 (4.32 g,11.4 mmol) was stirred with chlorosulfonic acid (13 mL) for 0.4 hours at room temperature and then for 0.6 hours at 75° C. The reaction was cooled, slowly added to ice water, and extracted with dichloromethane. The dichloromethane was stirred with ammonium hydroxide (20 mL) for 1.1 hours at room temperature. The organic layer was concentrated in vacuo, dissolved in ethyl acetate, washed with 3N HCl, brine, dried over MgSO$_4$, concentrated in vacuo, passed through a column of silica gel eluting with 50% ethyl acetate/hexane, and recrystallized from ethyl acetate/hexane to give a tan solid (1.20 g, 24%): mp 144–153° C. $^1$H NMR (acetone-d$_6$) 300 MHz 7.94 (d, J=8.5 Hz, 2H) 7.86 (d, J=8.3 Hz, 2H) 7.80 (d, J=1.8 Hz, 1H) 7.67 (d, J=8.3 Hz, 1H) 7.60 (dd, J=8.5 Hz 2.0 Hz, 1H) 6.67 (br s, 1H) 4.07 (s, 2H) 3.75 (s, 3H). High resolution mass spectrum Calc'd. for C$_{18}$H$_{15}$C$_{12}$N$_2$O$_5$S: 441.0079. Found: 441.0088.

Step 5. Preparation of [4-(4-aminosulfonylphenyl)-5-(3,4-dichlorophenyl)]-2-oxazoleacetic acid.

The oxazole ester from Step 4 (0.35 g, 0.8 mmol) was dissolved in methanol (10 mL), treated with NaOH (0.07 g dissolved in 5 mL water, 1.8 mmol), and stirred at room temperature. After 1.1 hours, additional NaOH (0.10 g, 2.5 mmol) was added and stirring continued for 1.4 hours. Water was added and the reaction mixture was extracted with ethyl acetate. The aqueous layer was then acidified with concentrated HCl and extracted with ethyl acetate. The ethyl acetate was washed with brine, dried over MgSO$_4$, and concentrated in vacuo to give a yellow solid (0.33 g, 97%): mp 204–209° C. $^1$H NMR (acetone-d6) 300 MHz δ 7.94 (d, J=8.9 Hz, 2H) 7.87 (d, J=8.7 Hz, 2H) 7.82 (d, J=2.0 Hz, 1H) 7.67 (d, J=8.3 Hz, 1H) 7.60 (dd, J=8.5 Hz 2.2 Hz, 1H) 6.68 (br s, 1H) 4.05 (s, 2H).

EXAMPLE 41

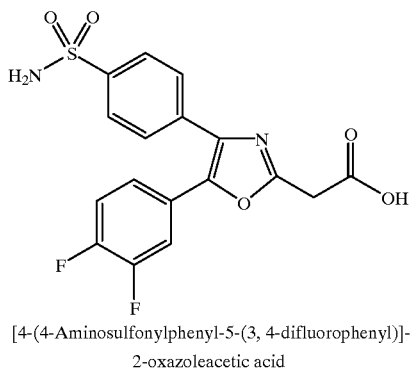

[4-(4-Aminosulfonylphenyl-5-(3, 4-difluorophenyl)]-2-oxazoleacetic acid

Step 1. Preparation of 2-hydroxy-2-(3,4-difluorophenyl)-1-phenylethanone.

A solution of 3,4-difluorobenzaldehyde (25.33 g, 178 mmol) and zinc iodide (0.13 g) in dichloromethane (100 mL) was treated with a solution of trimethylsilylcyanide (24.5 mL, 184 mmol) in dichloromethane (20 mL). The solution was stirred for 0.25 hours at room temperature, washed with saturated NaHCO$_3$ and brine, dried over MgSO$_4$, and concentrated in vacuo to give the trimethylsilyl cyanohydrin as a yellow oil (41.03 g). The trimethylsilyl cyanohydrin was dissolved in diethyl ether (50 mL) and added dropwise to a solution of phenylmagnesium bromide (186 mmol) in diethyl ether (560 mL) while maintaining the temperature between 25–33° C. with an ice water bath. The reaction was stirred for 0.5 hours at room temperature then quenched by adding 3N HCl (150 ML). The organic layer was collected, washed with saturated NaHCO$_3$ and brine, dried over MgSO$_4$, and concentrated in vacuo to give an orange oil (49.71 g). The orange oil was dissolved in 9:1 trifluoroacetic acid/water (100 mL) and stirred for 0.5 hours at room temperature. The reaction was neutralized with solid sodium carbonate, extracted with ethyl acetate, washed with brine, dried over MgSO$_4$, and concentrated in vacuo to give a brown solid which was recrystallized from diethyl ether/hexane to give the benzoin (16.35 g, 37%): mp 68–71° C. $^1$H NMR (CDCl$_3$) 300 MHz δ 7.87 (d, J=7.1 Hz, 2H) 7.56 (m, 1H) 7.42 (m, 2H) 7.07 (m, 3H) 5.92 (s, 1H) 4.40 (br s, 1H). $^{19}$F NMR (CDCl$_3$) 282 MHz -136.37 (m) -137.70 (m). Mass spectrum: M+Li=255.

Step 2. Esterification of 2-hydroxy-2-(3.4-difluorophenyl)-1-phenylethanone

The ethanone from Step 1 (5.93 g, 23.9 mmol) was dissolved in THF (6 mL), 2,2-dimethyl-1,3-dioxane-4,6-dione (3.70 g, 25.7 mmol) was added and the reaction heated to reflux for 23.7 hours. Additional 2,2-dimethyl-1,3-dioxane-4,6-dione (1.46 g, 10.1 mmol) was added and the reaction was stirred at reflux an additional 19.7 hours. The reaction mixture was partitioned between saturated NaHCO$_3$ and diethyl ether. The aqueous layer was acidified with concentrated HCl, extracted with diethyl ether, washed with brine, dried over MgSO$_4$, and concentrated in vacuo to give a yellow oil (6.05 g) which was used in the next step without further purification.

Step 3. Preparation of methyl [5-(3,4-difluorophenyl)-4-hydroxy-4-phenyl-2-oxazolinyl]acetate The ester from Step 2 (6.03 g, 18.0 mmol) was dissolved in methanol (10 mL), treated with ammonium acetate (3.07 g, 39.8 mmol), and heated to reflux. After 2.4 hours, the reaction was cooled, additional methanol (60 mL) was added, and the reaction mixture was acidified by adding concentrated sulfuric acid and heated to reflux for an additional 1.9 hours. The reaction mixture was concentrated in vacuo, and the residue was dissolved in ethyl acetate, washed with water, saturated NaHCO$_3$, and brine, dried over MgSO$_4$, and concentrated in vacuo to give an orange oil (4.64 g, 74%) which was used in the next step without further purification.

Step 4. Preparation of methyl-[4-(4-aminosulfonylphenyl)-5-(3.4-difluorophenyl)]-2-oxazoleacetate.

The oxazoline from Step 3 (3.34 g, 9.6 mmol) was stirred with chlorosulfonic acid (13 mL) for 0.4 hours at room temperature and then for 0.75 hours at 75° C. The reaction was cooled, slowly added to ice water, and extracted with dichloromethane. The dichloromethane was stirred at room temperature with ammonium hydroxide (20 mL) for 1.1 hours. The organic layer was concentrated in vacuo, dissolved in ethyl acetate, washed with 3N HCl, brine, dried over MgSO$_4$, concentrated in vacuo, passed through a column of silica gel eluting with 45% ethyl acetate/hexane, and recrystallized from ethyl acetate/hexane to give a yellow solid (0.71 g, 27%): mp 144–149° C. $^1$H NMR (acetone-d$_6$)

300 MHz δ 7.92 (d, J=8.7 Hz, 2H) 7.84 (d, J=8.5 Hz, 2H) 7.58 (m, 1H) 7.47 (m, 2H) 6.67 (br s, 1H) 4.06 (s, 2H) 3.75 (s, 3H). $^{19}$F NMR (acetone-d$_6$) 282 MHz −138.46 (m) −138.79 (m). High resolution mass spectrum Calc'd. for C$_{18}$H$_{15}$F$_2$N$_2$O$_5$S: 409.0670. Found: 409.0686.

Step 5. Preparation of [4-(4-aminosulfonylphenyl-5-(3,4-difluorophenyl)]-2-oxazoleacetate.

The oxazole ester from Step 4 (0.64 g, 1.3 mmol) was dissolved in methanol (10 mL), treated with NaOH (0.07 g dissolved in 5 mL water, 1.8 mmol), and stirred at room temperature. After one hour, additional NaOH (0.11 g, 2.8 mmol) was added and stirring continued for 1.4 hours. Water was added and the reaction mixture was extracted with ethyl acetate. The aqueous layer was acidified with concentrated HCl and extracted with ethyl acetate. The ethyl acetate was washed with brine, dried over MgSO$_4$, and concentrated in vacuo to give a white solid (0.49 g, 80%): mp 223–227° C. $^1$H NMR (acetone-d$_6$) 300 MHz δ 7.92 (d, J=8.7 Hz, 2H) 7.85 (d, J=8.7 Hz, 2H) 7.58 (m, 1H) 7.48 (m, 2H) 6.66 (br s, 1H) 4.04 (s, 2H). $^{19}$F NMR (acetone-d$_6$) 282 MHz −138.97 (m) −139.24 (m)

EXAMPLE 42

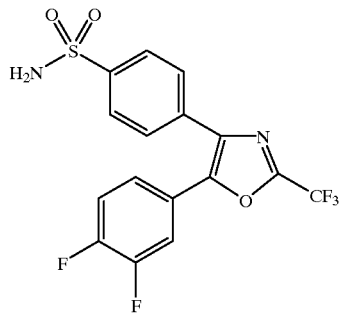

[2-Trifluoromethyl-5-(3, 4-difluorophenyl)-4-oxazolyl]benzenesulfonamide

Step 1. Preparation of 3-trifluoromethyl-4-phenyl-5-(3,4-difluorophenyl)oxazole.

A solution of 2-hydroxy-2-(3,4-difluorophenyl)-1-phenylethanone (Example 41, Step 1) (3.48 g, 14.0 mmol) in dimethylformamide (DMF) (15 mL) was added to a solution of trifluoroacetonitrile (1.85 g, 19.5 mmol) in DMF (150 mL). The reaction was cooled to 5° C., treated with 1,8-diazabicyclo[5.4.0]undecane (DBU) (2.31 g, 15.2 mmol), and stirred for 15.3 hours at room temperature and 3.5 hours at 90° C. The reaction mixture was diluted with ethyl acetate, washed with 3N HCl, saturated NaHCO$_3$, brine, dried over MgSO$_4$, concentrated in vacuo, and passed through a column of silica gel eluting with 10% diethyl ether/hexane to give a clear oil (2.35 g, 52%): $^1$H NMR (acetone-d$_6$) 300 MHz δ 7.66 (m, 3H) 7.47 (m, 5H). $^{19}$F NMR (acetone-d$_6$) 282 MHz −67.02 (s) −137.15 (m) −138.58 (m).

Step 2. Preparation of 4-[5-(3.4-difluorophenyl)-2-trifluoromethyl-4-oxazolyl]benzenesulfonamide 3-Trifluoromethyl-4-phenyl-5-(3,4-difluorophenyl) oxazole from Step 1 (1.02 g, 3.14 mmol) was stirred with chlorosulfonic acid (9.5 mL) for 0.9 hours at room temperature and then for 2.5 hours at 75° C. The reaction was cooled, slowly added to ice water, and extracted with dichloromethane. The dichloromethane was stirred with ammonium hydroxide (100 mL) for 14.7 hours at room temperature. The organic layer was concentrated in vacuo, dissolved in ethyl acetate, washed with 3N HCl, brine, dried over MgSO$_4$, concentrated in vacuo, and recrystallized from ethyl acetate/hexane to give a tan solid (0.87 g, 69%): mp 146–148° C. $^1$H NMR (acetone-d$_6$) 300 MHz δ 7.97 (d, J=8.5 Hz, 2H) 7.88 (d, J=8.7 Hz, 2H) 7.71 (m, 1H) 7.58 (m, 2H) 6.70 (br s, 1H). $^{19}$F NMR (acetone-d$_6$) 282 MHz −67.04 (s) −136.52 (m) −138.30 (m). High resolution mass spectrum Calc'd. for C$_{16}$H$_{10}$F$_5$N$_2$O$_3$S: 405.0332. Found: 405.0323.

EXAMPLE 43

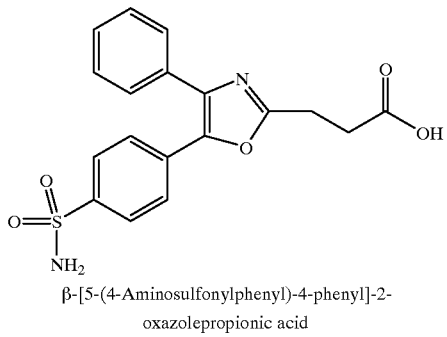

β-[5-(4-Aminosulfonylphenyl)-4-phenyl]-2-oxazolepropionic acid 4,5-Diphenyl-2-oxazolepropionic acid (1.0 g, 34 mmol), prepared as in U.S. Pat. No. 3,578,671, was added to chlorosulfonic acid cooled to 0° C. (25 mL), and the stirred solution was warmed to room temperature for 1.0 hour. The mixture was added dropwise to ice and dichloromethane (50 mL) with stirring. The resultant layers were separated, and the organic layer was washed once with water and added to a 0° C. stirred solution of ammonium hydroxide (10 mL). The mix was stirred for 1.0 hour and extracted with dichloromethane (3×50 mL). The combined organic layers were washed with 1 N HCl followed by brine and water, dried over MgSO$_4$ and concentrated. The crude product was purified by recrystallization from ethyl acetate/hexane to afford a white solid (0.6 g, 47.4%): mp 236–239° C. $^1$H NMR (DMSO-d$_6$) 300 MHz δ 12.15 (bs, 1H) 7.84 (d, J=8.5 Hz, 2H) 7.68 (d, J=8.5 Hz, 2H) 7.4–7.5 (m, 7H) 3.07 (t, J=7.1 Hz, 2H) 2.78 (t, J=7.1 Hz, 2H). Anal. Calc'd. for C$_{18}$H$_{16}$N$_2$O$_5$S: C, 58.06; C, 58.22; H, 4.33; H, 4.52; N, 7.52; N, 7.30.

EXAMPLE 44

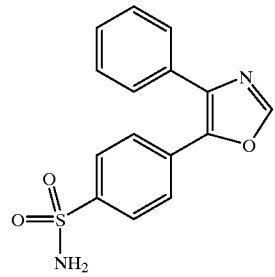

4-[4-Phenyl-5-oxazolyl]benzenesulfonamide

Step 1. Preparation of 4.5-diphenyloxazole.

Benzoin (4.25 g, 20 mmol) was stirred at 0° C. in dichloromethane (150 mL) with triethylamine (2.23 g, 22 mmol). Methanesulfonyl chloride (2.52 g, 22 mmol) was added dropwise. The solution was warmed to room temperature for 1.0 hour. Formamide (10 mL) was added and the mixture was concentrated to remove dichloromethane. The residue was heated to 50° C. overnight, cooled, diluted with ether, washed with 1 N HCl, brine, water dried over $MgSO_4$, concentrated in vacuo, and passed through a column of silica gel eluting with (1:16) ethyl acetate/hexane to give a clear oil (3.1 g, 70%): $^1$H NMR ($CDCl_3$) 300 MHz 7.96 (s, 1H) 7.60–7.70 (m, 4H) 7.31–7.41 (m, 6H). Anal. Calc'd. for $C_{15}H_{11}NO·1.5 H_2O$: C, 80.20; H, 5.10; N, 6.24. Found: C, 80.20; H, 5.07; N, 6.25.

Step 2. Preparation of 4-[4-phenyl-5-oxazolyl]benzenesulfonamide 4,5-Diphenyloxazole from Step 1 (0.5 g, 2.3 mmol) was added to chlorosulfonic acid cooled to 0° C. (5 mL), and the stirred solution was warmed to room temperature for 1.0 hour. The mixture was added dropwise to ice and dichloromethane (50 mL) with stirring. The resultant layers were separated, and the organic layer was washed once with water and added to a 0° C. stirred solution of ammonium hydroxide (10 mL) and stirred for 1.0 hour and extracted with dichloromethane (3×50 mL). The combined organic layers were washed with 1 N HCl followed by brine and water, dried over $MgSO_4$ and concentrated. The residue was purified by recrystallization from ether/hexanes to give a white solid (0.3 g, 44%): mp 122–125° C. $^1$H NMR (acetone-$d_6$) 300 MHz δ 8.35 (s, 1H) 7.88 (d, J=8.7 Hz, 2H) 7.79 (d, J=8.7 Hz, 2H) 7.64–7.70 (m, 2H) 7.40–7.5 (m, 3H) 6.68 (bs, 2H). Anal. Calc'd. for $C_{15}H_{12}N_2O_3S$: C, 59.99; H, 4.03; N, 9.33. Found: C, 60.09; H, 4.05; N, 9.27.

EXAMPLE 45

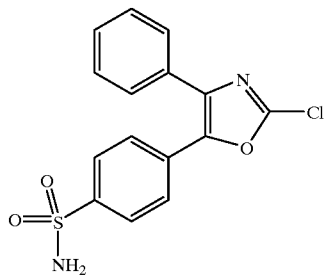

4-[2-Chloro-4-phenyl-5-oxazolyl]benzenesulfonamide

Step 1. Preparation of 4,5-diphenyloxazolone.

Benzoin (31.8 g, 0.15 mol) and urethane (42.79 g, 0.45 mol) were heated to reflux for 3.0 hours. The hot mixture was poured into water (150 mL). Acetone (150 mL) was added and heat was applied until the mixture dissolved. The solution was cooled and filtered yielding a white solid which was used in the next step without further purification: $^1$H NMR (DMSO-$d_6$) 300 MHz δ 7.2–7.5 (m, 11H).

Step 2. Preparation of 2-chloro-4,5-diphenyl-oxazole.

4,5-Diphenyloxazolone from Step 1 (30 g, 0.126 mol), triethylamine (12.8 g, 0.126 mol), and phosphorous oxychloride (96.6 g, 0.63 mol) were stirred at reflux for 4.0 hours. The mixture was concentrated in vacuo and dissolved in ether (250 mL), washed with 1 N HCl, brine, water, dried over $MgSO_4$ and concentrated to a light yellow oil which was used in the next step without further purification or characterization.

Step 3. Preparation of 4-[2-chloro-4-phenyl-5-oxazolyl]benzenesulfonamide.

2-Chloro-4,5-diphenyl-oxazole from Step 2 (1.53 g, 6 mmol) was added to chlorosulfonic acid cooled to 0° C. (20 mL), and the stirred solution was warmed to room temperature for 1.0 hour. The mixture was added dropwise to ice and dichloromethane (50 mL) with stirring. The resultant layers were separated, and the organic layer was washed once with water and added to a 0° C. stirred solution of ammonium hydroxide (10 mL). The mixture was stirred for 1.0 hour and extracted with dichloromethane (3×50 mL). The combined organic layers were washed with 1 N HCl followed by brine and water, dried over $MgSO_4$ and concentrated. Recrystallization from ethyl acetate/hexanes gave a white solid (1.5 g, 75%): mp 158–159° C. $^1$H NMR (acetone-$d_6$) 300 MHz δ 7.98 (d, J=8.7 Hz, 2H) 7.78 (d, J=8.7 Hz, 2H) 7.64–7.70 (m, 2H) 7.42–7.5 (m, 3H) 6.72 (bs, 2H). Anal. Calc'd. for $C_{15}H_{11}N_2O_3SCl$: C, 53.82; H, 3.31; N, 8.37. Found: C, 53.92; H, 3.32; N, 8.33.

EXAMPLE 46

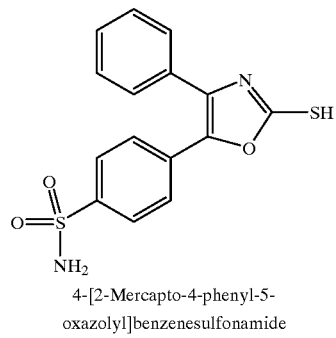

4-[2-Mercapto-4-phenyl-5-oxazolyl]benzenesulfonamide

4-[2-Chloro-4-phenyl-5-oxazolyl]benzenesulfonamide (Example 45) (1.67 g, 5 mmol), dimethylsulfoxide (50 mL), and sodium thiomethoxide (0.70 g, 10 mmol) were stirred at room temperature for 16.0 hours. The mixture was diluted with ethyl acetate (100 mL) washed with 1 N HCl, brine, water, dried over $MgSO_4$ and concentrated. Recrystallization from ethyl acetate/hexanes gave the product as a brown solid (0.8 g, 48%): mp 247–249° C. $^1$H NMR (acetone-$d_6$) 300 MHz δ 12.1 (bs, 1H) 7.89 (d, J=8.7 Hz, 2H) 7.62–7.68 (m, 4H) 7.54–7.59 (m, 3H) 6.7 (bs, 2H). Anal. Calc'd. for $C_{15}H_{12}N_2O_3S_2$: C, 54.20; H, 3.64; N, 8.43. Found: C, 54.27; H, 3.68; N, 8.41.

EXAMPLE 47

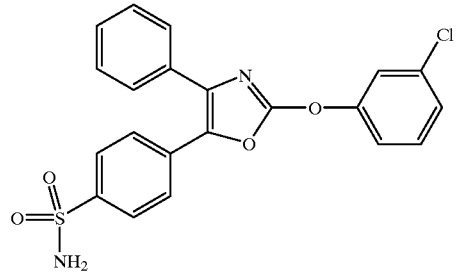

4-[2-(3-Chlorophenoxy)-4-phenyl-5-oxazolylbenzenesulfonamide

4-[2-Chloro-4-phenyl-5-oxazolyl]benzenesulfonamide (Example 45) (1.67 g, 5 mmol), DMF (20 mL), potassium carbonate (1.38 g, 10 mmol), and 3-chlorophenol (0.64 g, 5 mmol) were stirred at room temperature for 16.0 hours, diluted with ethyl acetate (100 mL), washed with 1 N HCl, brine and water, dried over $MgSO_4$ and concentrated. The residue was dissolved in ethyl acetate/hexanes (1:1) and filtered through silica. The eluant was concentrated and the residue recrystallized from ethyl acetate/hexanes to afford the product as a light yellow solid (1.4 g, 66%): mp 138–140° C. $^1$H NMR (acetone-d$_6$) 300 MHz δ 7.92 (d, J=8.9 Hz, 2H) 7.75 (d, J=8.9 Hz, 2H) 7.7 (m, 1H) 7.60–7.65 (m, 2H) 7.54–7.56 (m, 2H) 7.38–7.46 (m, 4H) 6.90 (bs, 2H). Anal. Calc'd. for C$_{21}$H$_{15}$N$_2$O$_4$SCl: C, 59.09; H, 3.54; N, 6.56. Found: C, 59.02; H, 3.55; N, 6.61.

EXAMPLE 48

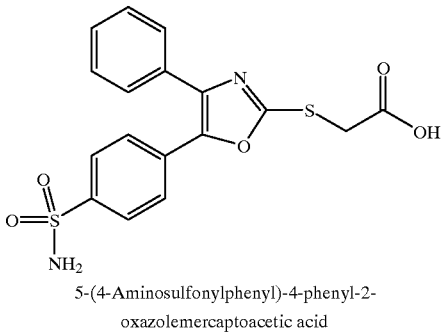

5-(4-Aminosulfonylphenyl)-4-phenyl-2-oxazolemercaptoacetic acid

4-[2-Chloro-4-phenyl-5-oxazolyl]benzenesulfonamide (Example 45) (1.67 g, 5 mmol), DMF (20 mL), sodium hydride (1.32 g, 5.5 mmol), and mercaptoacetic acid, sodium salt (0.63 g, 5.5 mmol) were stirred at room temperature for 16.0 hours. The solution was diluted with ethyl acetate (100 mL), washed with 1 N HCl, brine and water, dried over MgSO$_4$ and concentrated. The residue was purified by flash column chromatography eluting with ethyl acetate:methanol:water (20:10:1) to provide the product as a light yellow solid (0.8 g, 41%): mp 235–238° C. $^1$H NMR (D$_2$O) 300 MHz δ 7.62 (d, J=8.7 Hz, 2H) 7.43 (d, J=8.7 Hz, 2H) 7.32 (m, 5H) 3.76 (s, 2H). High resolution mass spectrum Calc'd. for C$_{17}$H$_{15}$N$_2$O$_5$S$_2$: 391.0422. Found: 391.0423.

EXAMPLE 49

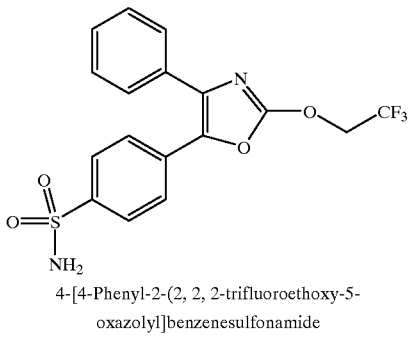

4-[4-Phenyl-2-(2, 2, 2-trifluoroethoxy-5-oxazolyl]benzenesulfonamide

4-[2-Chloro-4-phenyl-5-oxazolyl]benzenesulfonamide (Example 45) (1.67 g, 5 mmol), DMF (20 mL), potassium carbonate (1.38 g, 10 mmol), and 2,2,2-trifluoroethanol (0.75 g, 7.5 mmol) were stirred at room temperature for 16.0 hours. The solution was diluted with ethyl acetate (100 mL), washed with 1 N HCl, brine and water, dried over MgSO$_4$ and concentrated. The residue was dissolved in ethyl acetate/ hexanes (1:1) and filtered through silica. The eluant was concentrated and recrystallized from ethyl acetate/hexanes to provide the product was a white solid (1.4 g, 70%): mp 180–182° C. $^1$H NMR (CDCl$_3$) 300 MHz δ 7.85 (d, J=8.5 Hz, 2H) 7.65 (d, J=8.5 Hz, 2H) 7.6 (m, 2H) 7.4 (m, 3H) 4.9 (dd, J=8.1 Hz, 2H) 4.85 (bs, 2H). Anal. Calc'd. for C$_{17}$H$_{13}$N$_2$O$_4$S$_1$F$_3$: C, 51.26; H, 3.29; N, 7.03. Found: C, 51.32; H, 3.30; N, 7.01.

EXAMPLE 50

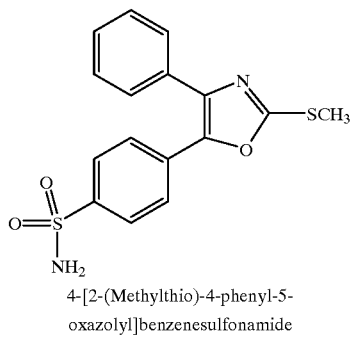

4-[2-(Methylthio)-4-phenyl-5-oxazolyl]benzenesulfonamide

4-[2-Chloro-4-phenyl-5-oxazolyl]benzenesulfonamide (Example 45) (1.67 g, 5 mmol), methanol (50 mL), and sodium thiomethoxide (0.39 g, 5.5 mmol) were stirred at room temperature for 16.0 hours. The solution was concentrated and dissolved in ethyl acetate (100 mL), washed with 1 N HCl, brine and water, dried over MgSO$_4$ and concentrated. The residue was recrystallized from ethyl acetate/ hexanes to give the product was a light yellow solid (1.4 g, 81%): mp 162–164° C. $^1$H NMR (CDCl$_3$) 300 MHz δ 7.85 (d, J=8.9 Hz, 2H) 7.68 (d, J=8.9 Hz, 2H) 7.6 (m, 2H) 7.4 (m, 3H) 4.85 (bs, 2H) 2.75 (s, 3H). Anal. Calc'd. for C$_{16}$H$_{14}$N$_2$O$_3$S$_2$: C, 55.48; H, 4.07; N, 8.09. Found: C, 55.56; H, 4.10; N, 8.15.

EXAMPLE 51

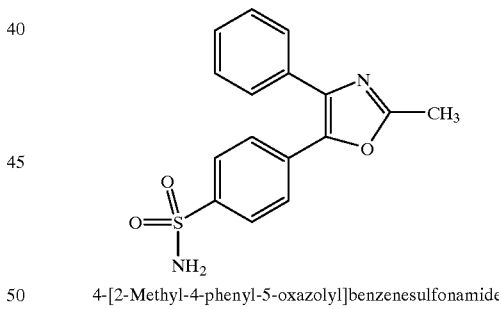

4-[2-Methyl-4-phenyl-5-oxazolyl]benzenesulfonamide

Chlorosulfonic acid (25 mL) was cooled to −78° C. with stirring and 2-methyl-4,5-diphenyloxazole (Aldrich) (2.0 g, 8.5 mmol) was added, and the stirred solution was warmed to room temperature for 4.0 hours. The mixture was then added dropwise to ice and dichloromethane (100 mL) with stirring. The resultant layers were separated, and the organic layer was washed once with water and added to a 0° C. stirred solution of ammonium hydroxide (20 mL). The solution was stirred for 1.0 hour and extracted with dichloromethane (3×50 mL). The combined organic layers were washed with 1 N HCl followed by brine and water, dried over MgSO$_4$ and concentrated. The residue was purified by recrystallization from ethanol/water to give the product as a white solid (1. 6 g, 60%): mp 176–178° C. $^1$H NMR (acetone-d$_6$) 300 MHz δ 7.92 (d, J=8.7 Hz, 2H) 7.74 (d, J=8.7 Hz, 2H) 7.61–7.66 (m, 2H) 7.40–7.48 (m, 3H) 6.68 (bs, 2H) 2.53 (s, 3H). Anal. Calc'd. for $C_{16}H_{14}N_2O_3S$: C, 61.13; H, 4.49; N, 8.91. Found: C, 60.89; H, 4.53; N, 8.85.

EXAMPLE 52

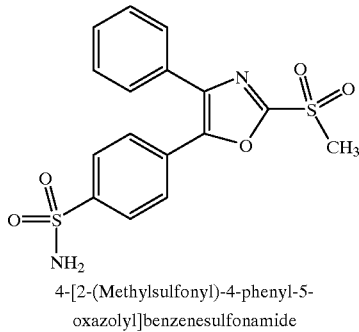

4-[2-(Methylsulfonyl)-4-phenyl-5-oxazolyl]benzenesulfonamide

EXAMPLE 53

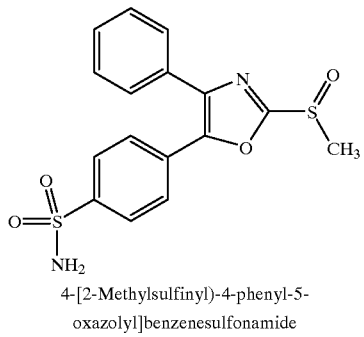

4-[2-Methylsulfinyl)-4-phenyl-5-oxazolyl]benzenesulfonamide

4-[2-Methylthio-4-phenyl-5-oxazolyl] benzenesulfonamide (Example 50) (0.5 g, 1.44 mmol), ethanol (100 mL), water (50 mL), and Oxone® (potassium peroxymonosulfate, 0.88 g, 1.44 mmol) were stirred at room temperature for 16.0 hours. Sodium metabisulfite (5 g) and water (50 mL) were added and the resulting mixture stirred for 0.25 hours before the addition of ethyl acetate (200 mL). The organic layer was separated and washed with brine and water, dried over $MgSO_4$ and concentrated. The residue was purified by flash chromatography eluting with ethyl acetate-:hexanes (1:3). The first material collected was concentrated and recrystallized to yield 4-[$^2$-methylsulfonyl)-4-phenyl-5-oxzolyk]benzenesulfonamide as a white solid (0.3 g, 55%): mp 186–188° C. $^1$H NMR (DMSO-$d_6$) 300 MHz δ 7.92 (d, J=8.5 Hz, 2H) 7.81 (d, J=8.5 Hz, 2H) 7.6 (m, 2H) 7.48 (m, 5H) 3.3 (s, 3H). Anal. Calc'd. for $C_{16}H_{14}N_2O_5S_2$: C, 50.78; H, 3.73; N, 7.40. Found: C, 50.79; H, 3.72; N, 7.38. The second material collected was concentrated and recrystallized to yield 4-[2-methylsulfinyl)-4-phenyl-5-oxazolyl] benzenesulfonamide as a white solid (0.16 g, 31%): mp 174–176° C. $^1$H NMR (DMSO-$d_6$) 300 MHz δ 7.9 (d, J=8.5 Hz, 2H) 7.8 (d, J=8.5 Hz, 2H) 7.6 (m, 2H) 7.48 (m, 5H) 3.2 (s, 3H). Anal. Calc'd. for $C_{16}H_{14}N_2O_4S_2$: C, 53.03; H, 3.89; N, 7.73. Found: C, 53.08; H, 3.85; N, 7.66.

EXAMPLE 54

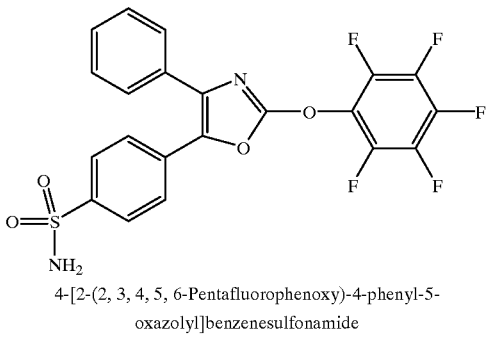

4-[2-(2, 3, 4, 5, 6-Pentafluorophenoxy)-4-phenyl-5-oxazolyl]benzenesulfonamide

4-[2-Chloro-4-phenyl-5-oxazolyl]benzenesulfonamide (Example 45) (1.0 g, 3 mmol), DMF (20 mL), potassium carbonate (0.83 g, 6 mmol), and pentafluorophenol (0.55 g, 3 mmol) were stirred at room temperature for 16.0 hours. The solution was diluted with ethyl acetate (100 mL), washed with 1 N HCl, brine and water, dried over $MgSO_4$ and concentrated. The residue was dissolved in ethyl acetate/hexanes (1:1) and filtered through silica and the eluant concentrated and recrystallized from ethyl acetate/hexanes to afford the product was a white solid (0.4 g, 28%): mp 146–148° C. $^1$H NMR (DMSO-$d_6$) 300 MHz δ 7.88 (d, J=8.5 Hz, 2H) 7.71 (d, J=8.5 Hz, 2H) 7.56 (m, 2H) 7.42–7.48 (m, 5H).

EXAMPLE 55

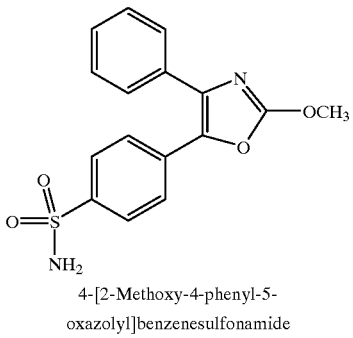

4-[2-Methoxy-4-phenyl-5-oxazolyl]benzenesulfonamide

4-[2-Chloro-4-phenyl-5-oxazolyl]benzenesulfonamide (Example 45) (1.0 g, 3 mmol), methanol (15 mL), and sodium methoxide (25% in methanol) (0.65 g, 6 mmol) were stirred at room temperature for 16.0 hours. Water was added until crystals appeared that were isolated by filtration to afford the desired product as a white solid (0.6 g, 61%): mp 180–182° C. $^1$H NMR (DMSO-$d_6$) 300 MHz δ 7.81 (d, J=8.5 Hz, 2H) 7.62 (d, J=8.5 Hz, 2H) 7.57 (m, 2H) 7.38–7.46 (m, 5H) 4.12 (s, 3H). Anal. Calc'd. for $C_{16}H_{14}N_2O_4S$: C, 58.17; H, 4.27; N, 8.48. Found: C, 8.12; H, 4.31; N, 8.44.

EXAMPLE 56

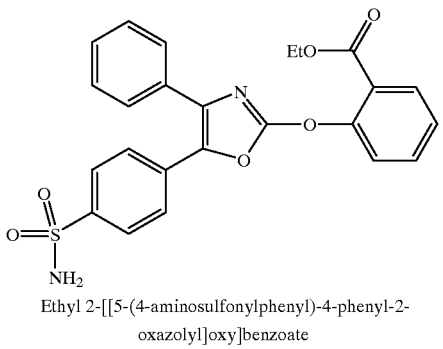

Ethyl 2-[[5-(4-aminosulfonylphenyl)-4-phenyl-2-oxazolyl]oxy]benzoate

4-[2-Chloro-4-phenyl-5-oxazolyl]benzenesulfonamide (Example 45) (1.0 g, 3 mmol), DMF (20 mL), potassium carbonate (0.46 g, 3.3 mmol), and ethyl salicylate (0.55 g, 3.3 mmol) were stirred at room temperature for 16.0 hours, diluted with ethyl acetate (100 mL), washed with 1 N HCl, brine and water, dried over $MgSO_4$ and concentrated. The residue was dissolved in ethyl acetate/hexanes (1:1) and filtered through silica. The eluant was concentrated and recrystallized from ethyl acetate/hexanes to give the product was a white solid (0.7 g, 50%): mp 183–184° C. $^1$H NMR ($CDCl_3/CD_3OD$) 300 MHz 8.12 (dd, J=1.8 Hz and J=7.8 Hz, 1H) 7.86 (d, J=8.5 Hz, 2H) 7.62–7.72 (m, 3H) 7.38–7.54 (m, 7H) 4.35 (dd, J=7.2 Hz, 2H) 1.3 (t, J=7.2 Hz, 3H). Anal. Calc'd. for $C_{24}H_{20}N_2O_6S$: C, 62.06; H, 4.34; N, 6.03. Found: C, 61.85; H, 4.37; N, 5.91.

EXAMPLE 57

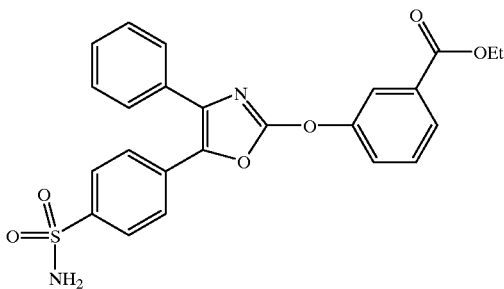

Ethyl 3-[[5-(4-aminosulfonylphenyl)-4-phenyl-2-oxazolyl]oxy]benzoate

4-[2-Chloro-4-phenyl-5-oxazolyl]benzenesulfonamide (Example 45) (1.0 g, 3 mmol), DMF (20 mL), potassium carbonate (0.46 g, 3.3 mmol), and ethyl 3-hydroxybenzoate (0.55 g, 3.3 mmol) were stirred at room temperature for 16.0 hours. The solution was diluted with ethyl acetate (100 mL), washed with 1 N HCl, brine and water, dried over $MgSO_4$ and concentrated. The residue was dissolved in ethyl acetate/hexanes (1:1), filtered through silica and the eluant was concentrated and recrystallized from ethyl acetate/hexanes to give the product as a white solid (0.6 g, 43%): mp 157–158° C. $^1$H NMR ($CDCl_3/CF_3CO_2H$) 300 MHz δ 8.12 (dd, J=1.6 Hz and J=0.6 Hz, 1H) 7.94–8.0 (dt, J=1.0 Hz and J=7.8 Hz, 1H) 7.89 (d, J=8.7 Hz, 2H) 7.72 (d, J=8.7 Hz, 2H) 7.67 (m, 1H) 7.60 (m, 2H) 7.52 (m, 1H) 7.4 (m, 3H) 4.56 (s, 2H) 4.4 (q, J=7.1 Hz, 2H) 1.4 (t, J=7.1 Hz, 3H). Anal. Calc'd. for $C_{24}H_{20}N_2O_6S$: C, 62.06; H, 4.34; N, 6.03. Found: C, 62.00; H, 4.36; N, 5.95.

EXAMPLE 58

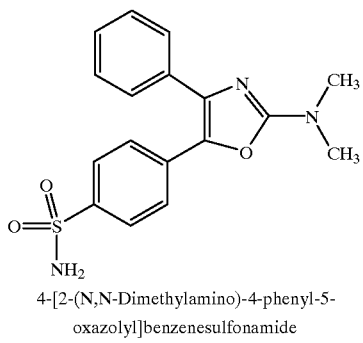

4-[2-(N,N-Dimethylamino)-4-phenyl-5-oxazolyl]benzenesulfonamide

4-[2-Chloro-4-phenyl-5-oxazolyl]benzenesulfonamide (Example 45) (1.0 g, 3 mmol) and 40% aqueous dimethylamine (25 mL) were stirred at room temperature for 16.0 hours, diluted with ethyl acetate (100 mL), washed with brine and water, dried over $MgSO_4$ and concentrated. The residue was recrystallized from ethyl acetate/hexanes to afford the product as a light yellow/green solid (0.6 g, 58%): mp 254–256° C. $^1$H NMR (DMSO-$d_6$) 300 MHz 7.74 (d, J=8.7 Hz, 2H) 7.56 (m, 4H) 7.38–7.46 (m, 3H) 7.33 (bs, 2H) 3.08 (s, 6H). Anal. Calc'd. for $C_{17}H_{17}N_3O_3S$: C, 57.31; H, 5.21; N, 11.79. Found: C, 57.32; H, 5.23; N, 11.73.

EXAMPLE 59

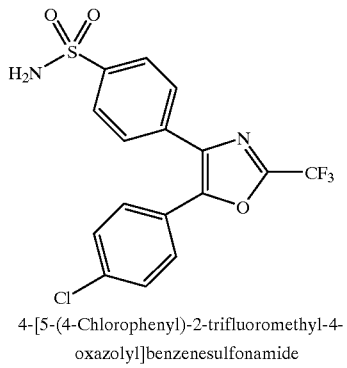

4-[5-(4-Chlorophenyl)-2-trifluoromethyl-4-oxazolyl]benzenesulfonamide

Step 1. Preparation of 2-hydroxy-2-(4-chlorophenyl)-1-phenylethanone.

A solution of 4-chlorobenzaldehyde (9.86 g, 70 mmol) and zinc iodide (0.18 g) in dichloromethane (40 mL) was treated with a solution of trimethylsilylcyanide (9 mL, 71 mmol) in dichloromethane (20 mL). The solution was stirred for 0.33 hours at room temperature, washed with water and saturated $NaHCO_3$, dried over $MgSO_4$, and concentrated in vacuo to give the trimethylsilyl cyanohydrin as an orange oil (13.90 g). The trimethylsilyl cyanohydrin was dissolved in diethyl ether (50 mL) and added dropwise to a solution of phenylmagnesium bromide (69 mmol) in diethyl ether (269 mL) while maintaining the temperature between 15–28° C. with an ice water bath. The reaction was stirred for 0.75 hours at room temperature then quenched by adding 3N HCl (50 mL). The organic layer was collected, washed with saturated $NaHCO_3$ and brine, dried over $MgSO_4$, and concentrated in vacuo to give a yellow solid (13.06 g). The yellow solid was dissolved in 9:1 trifluoroacetic acid/water (30 mL) and stirred for 1.6 hours at room temperature. The reaction was neutralized with solid sodium carbonate, extracted with ethyl acetate, washed with 10% $Na_2CO_3$ and brine, dried over $MgSO_4$, concentrated in vacuo to give a yellow solid (9.43 g) and used in the next step without further purification.

Step 2. Preparation of 2-trifluoromethyl-4-phenyl-5-(4-chlorophenyl)oxazole.

Trifluoroacetonitrile (1.5 g, 15.8 mmol) was bubbled into DMF (100 mL). This solution was cooled to 0° C. and 4'-chlorobenzoin (Example 37, Step 1) (2.5 g, 10 mmol) was added. DBU (1.83 g, 12 mmol) was added and the solution was warmed to room temperature for 4 hours. The reaction was heated to approximately 100° C. for an additional 4 hours. The solution was cooled to room temperature, poured into 400 mL 1N HCl and extracted with 500 mL ethyl acetate. The organics were washed consecutively with 1N HCl (400 mL), $NaHCO_3$ (saturated) (400 mL) and brine (400 mL), dried over $Na_2SO_4$ and concentrated. The residue was purified by silica gel chromatography eluting with 10% ether in hexane to give a white solid (2.2 g, 67%): mp 53—53° C. Anal. Calc'd. for $C_{16}H_9NOClF_3$: C, 59.37; H, 2.80; N, 4.33. Found: C, 59.35; H, 2.76; N, 4.25.

Step 3. Preparation of 4-[2-trifluoromethyl-5-(4-chlorophenyl)-4-oxazolyl]benzenesulfonamide.

2-Trifluoromethyl-4-phenyl-5-(4-chlorophenyl)oxazole (Step 2) (0.9 g, 2.8 mmol) was added to chlorosulfonic acid, cooled to 0° C. (25 mL), and the reaction was warmed to room temperature for 5 hours. The solution was carefully poured into ice water and extracted with three 75 mL portions of dichloromethane. The combined organics were washed once with brine (75 mL) and stirred over ice cold $NH_4OH$ (125 mL) for 2 hours. The dichloromethane layer was separated, washed consecutively with 1N HCl (2×75 mL), $NaHCO_3$ (saturated) (75 mL) and brine (75 mL), dried over $Na_2SO_4$ and concentrated. The crude material was crystallized from ethyl acetate/hexane to yield 4-[5-(4-chlorophenyl)-2-trifluoromethyl-4-oxazolyl]benzenesulfonamide (0.84 g, 75%): mp 167–168° C. Anal. Calc'd. for $C_{16}H_{10}N_2O_3SClF_3$: C, 47.71; H, 2.50; N, 6.96. Found: C, 47.62; H, 2.44; N, 6.88.

EXAMPLE 60

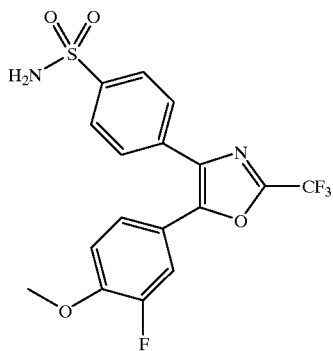

4-[5-(3-Fluoro-4-methoxyphenyl-2-trifluoromethyl)-4-oxazolyl]benzenesulfonamide

Step 1. Preparation of 3-fluoro-p-anisaldehyde silyl cyanohydrin.

3-Fluoro-p-anisaldehyde (14.68 g, 95.2 mmol) was dissolved in anhydrous methylene chloride (300 mL) and $ZnI_2$ (0.4 g) was added. Trimethylsilyl cyanide (12.7 g, 95.2 mmol) and methylene chloride (75 mL) were added dropwise over 10 minutes. The reaction was stirred an additional 20 minutes and separated. The organics were washed consecutively with water (350 mL), $NaHCO_3$ (saturated) (300 mL) and brine (300 mL). The methylene chloride was dried over $Na_2SO_4$ and concentrated to yield silyl cyanohydrin (24.52 g, 100%) which was used without further purification.

Step 2. Preparation of 3'-fluoro-4'-methoxy benzoin.

3-Fluoro-p-anisaldehyde silyl cyanohydrin (from Step 1) (24.52 g, 96.8 mmol) and diethyl ether (75 mL) added dropwise to the solution of diethyl ether (250 mL) and phenyl magnesium bromide (3M in ether, 34 mL) were added at such a rate that the reaction temperature did not rise above 30° C. Upon complete addition, the reaction (which now contained a gummy precipitate) was stirred an additional 15 minutes at which time 1N HCl (400 mL) was added and the reaction stirred until all solids were dissolved. The reaction was poured into a 1L separatory funnel and the layers separated. The organics were washed with $NaHCO_3$ (saturated) (400 mL) and brine (400 mL), dried over $Na_2SO_4$ and concentrated to yield a mixture of benzoin and silyl benzoin. The crude product was dissolved in 90% TFA (75 mL) and stirred for 15 minutes. The TFA solution was poured into saturated $NaHCO_3$(aq.). The benzoin was extracted with ethyl acetate (350 mL) and washed with $NaHCO_3$ (saturated) (300 mL) and brine (300 mL). Crystallization of crude benzoin from ether and hexane yielded a first crop of crystals which were >99% pure (14.9 g): mp 84–85° C. Anal. Calc'd. for $C_{15}H_{13}O_3F$: C, 69.22; H, 5.03. Found: C, 69.13; H, 5.07.

Step 3. Preparation of 2-trifluoromethyl-4-phenyl-5-(3-fluoro-4-methoxyphenyl)oxazole.

Trifluoroacetonitrile 0.92 g (9.7 mmol) was added to a solution of DMF (100 ml). This solution was cooled to 0° C. and 3'-fluoro-4'-methoxy benzoin from Step 2 (2.08 g, 8 mmol) was added. DBU (1.45 g, 9.7 mmol) was added and the solution was warmed to room temperature for 4 hours. The reaction was heated to approximately 100° C. for an additional 4 hours. The solution was cooled to room temperature, poured into 400 mL 1N HCl and extracted with 500 mL ethyl acetate. The organics were washed consecutively with 1N HCl (400 mL), $NaHCO_3$ (saturated) (400 mL) and brine (400 mL) dried over $Na_2SO_4$ and concentrated. The crystalline solid residue was recrystallized from ether and hexane to yield analytically pure oxazole (2.32 g, 86%): mp 75–76° C. Anal. Calc'd. for $C_{17}H_{11}NO_2F_4$: C, 60.54; H, 3.29; N, 4.15. Found: C, 60.62; H, 3.30; N, 4.18.

Step 4. Preparation of 4-[5-(3-fluoro-4-methoxyphenyl)-2-trifluoromethyl-4-oxazolyl]benzenesulfonamide 2-Trifluoromethyl-4-phenyl-5-(3-fluoro-4-methoxyphenyl)oxazole from Step 3 (337 mg, 1 mmol) was added to chlorosulfonic acid cooled to 0° C. (10 mL) and the reaction was warmed to room temperature for 3 hours. The solution was carefully poured into ice water and extracted with three 75 mL portions of dichloromethane. The combined organics were washed once with brine (75 mL) and stirred over ice cold $NH_4OH$ (125 mL) for 2 hours. The dichloromethane layer was separated and washed consecutively with 1N HCl (2×75 mL), $NaHCO_3$ (saturated) (75 mL) and brine (75 mL), dried over $Na_2SO_4$ and concentrated. The crude material was chromatographed over $SiO_2$ eluting with a gradient from 10%–35% ethyl acetate in hexane to yield 4-[5-(3-fluoro-4-methoxyphenyl)-2-trifluoromethyl-4-oxazolyl]benzenesulfonamide (20 mg, 5%): mp 150–151° C. $^1H$ NMR (acetone-d6), 300 MHz δ 3.99 (s, 3H), 6.69 (s, 2H), 7.32 (t, 1H), 7.51 (m, 2H), 7.85 (d, J=8.3 Hz, 2H), 7.97 (d, J=8.3 Hz, 2H).

EXAMPLE 61

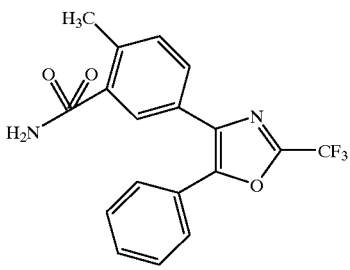

4-Methyl-3-[5-phenyl-2-trifluoromethyl-4-oxazolyl]benzenesulfonamide

EXAMPLE 62

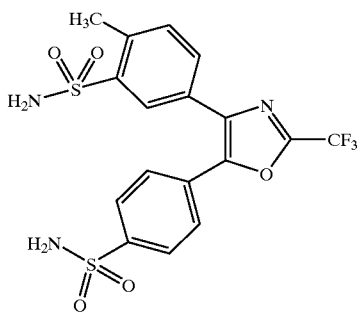

4-[4-(3-Aminosulfonyl-4-methylphenyl)-2-trifluoromethyl-5-oxazolyl]benzenesulfonamide Step 1. Preparation of 2-hydroxy-2-phenyl-1-(4-methylphenyl)ethanone.

The trimethylsilyl cyanohydrin of benzaldehyde Example 34, Step 1 (5.0 g, 24.4 mmol) was dissolved in diethyl ether (50 mL) and added dropwise to a solution of 4-methylphenylmagnesium bromide (29.3 mmol) in diethyl ether (130 mL) while maintaining the temperature between 23–35° C. with an ice water bath. The reaction was stirred for 0.5 hours at room temperature. At this time 1N HCl (100 mL) and ether (150 mL) were added and the layers separated. The organic layer was washed with saturated NaHCO$_3$ and brine, dried over Na$_2$SO$_4$, and concentrated in vacuo to give a yellow oil. The yellow oil was dissolved in 9:1 trifluoroacetic acid/water (30 mL) and stirred for 0.5 hours at room temperature. The reaction was neutralized with solid sodium bicarbonate, extracted with ethyl acetate, washed with saturated NaHCO$_3$ and brine, dried over Na$_2$SO$_4$, concentrated in vacuo and recrystallized from diethyl ether/hexane to give the benzoin (2.54 g, 46%): $^1$H NMR (CDCl$_3$) 300 MHz, δ 2.35 (s, 3H), 4.45 (broad s, 1H), 5.92 (s, 1H), 7.19 (m, 2H), 7.32 (m, 3H), 7.82 (m, 2H).

Step 2. Preparation of 2-trifluoromethyl-4-(4-methylphenyl)-5-phenyloxazole.

Trifluoroacetonitrile (0.84 g, 8.84 mmol) was added to DMF (100 ml). This solution was cooled to 0° C. and 4-methylbenzoin from Step 1 (1.36 g, 6 mmol) was added. DBU (1.35 g, 8.84 mmol) was added and the solution was warmed to room temperature for 4 hours. The reaction was then heated to approximately 100° C. for an additional 4 hours. The solution was cooled to room temperature, poured into 400 mL 1N HCl and extracted with 500 mL ethyl acetate. The organics were washed consecutively with 1N HCl (400 mL), NaHCO$_3$ (saturated) (400 mL) and brine (400 mL), dried over Na$_2$SO$_4$ and concentrated. The residue was purified by silica gel chromatography eluting with 1% ether in hexane to give a white solid (0.72 g, 40%): mp 49–50° C. Anal. Calc'd. for C$_{17}$H$_{12}$NOF$_3$: C, 67.33; H, 3.99; N, 4.62. Found: C, 67.27; H, 3.99; N, 4.58.

Step 3. Preparation of 2-trifluoromethyl-4-(4-methylphenyl)-5-phenyloxazole.

2-Trifluoromethyl-4-(4-methylphenyl)-5-phenyloxazole from Step 2 (0.4 g) was added to chlorosulfonic acid (10 mL) cooled to 0° C. and the reaction was warmed to room temperature for 2 hours. The solution was carefully poured into ice water and extracted with three 75 mL portions of dichloromethane. The combined organics were washed once with brine (75 mL) and stirred over ice cold NH$_4$OH (125 mL) for 2 hours. The dichloromethane layer was separated and washed consecutively with 1N HCl (2×75 mL), NaHCO$_3$ (saturated) (75 mL) and brine (75 mL), dried over Na$_2$SO$_4$ and concentrated. The crude material was chromatographed, eluting with a gradient from 10–60% ethyl acetate in hexane to yield 4-methyl-3-[5-phenyl-2-trifluoromethyl-4-oxazolyl]benzenesulfonamide (141 mg, 28%): mp 150–151° C.; Anal. Calc'd. for C$_{17}$H$_{13}$N$_2$O$_3$SF$_3$: C, 53.40; H, 3.43; N, 7.27. Found: C, 53.33; H, 3.48; N, 7.27; and 4-[4-(3-aminosulfonyl-4-methylphenyl)-2-trifluoromethyl-5-oxazolyl]benzenesulfonamide (150 mg, 25%): mp 241–242° C.; Anal. Calc'd. for C$_{17}$H$_{14}$N$_3$O$_5$S$_2$F$_3$: C, 44.25; H, 3.06; N, 9.11; Found: C, 44.34; H, 3.07; N, 9.05.]

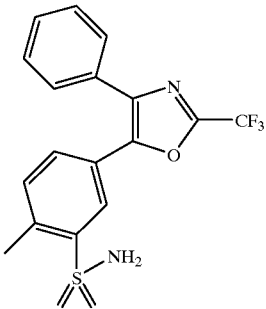

4-Methyl-3-[4-phenyl-2-trifluoromethyl-5-oxazolyl]benzenesulfonamide

EXAMPLE 63

Step 1. Preparation of 2-hydroxy-2-(4-methylphenyl)-1-phenylethanone.

A solution of p-tolulylaldehyde (33.55 g, 279 mmol) and trimethylsilylcyanide (38 mL, 285 mmol) in dichloromethane (160 mL) was treated with zinc iodide (0.34 g). The solution was stirred for 0.33 hours at room temperature, washed with water and saturated NaHCO$_3$, dried over MgSO$_4$, and concentrated in vacuo to give the trimethylsilyl cyanohydrin as a yellow oil (59.76 g). The trimethylsilyl cyanohydrin was dissolved in diethyl ether (200 mL) and added dropwise to a solution of phenylmagnesium bromide (285 mmol) in diethyl ether (1095 mL) while maintaining the temperature between 25–30° C. with an ice water bath. The reaction was stirred for 0.5 hours at room temperature then quenched by adding 3N HCl (220 mL). The organic layer was collected, washed with saturated NaHCO$_3$ and brine, dried over MgSO$_4$, and concentrated in vacuo to give an orange oil (48.22 g). The orange oil was dissolved in 9:1 trifluoroacetic acid/water (100 mL) and stirred for 0.67 hours at room temperature. The reaction was extracted with ethyl acetate, washed with 10% $Na_2CO_3$ and brine, dried over $MgSO_4$, and concentrated in vacuo to give a brown solid which was recrystallized from diethyl ether/hexane to give the benzoin (32.90 g, 52%): mp 118–123° C. $^1$H NMR ($CDCl_3$) 300 MHz δ7.90 (d, J=7.1 Hz, 2H) 7.57 (m, 1H) 7.39 (m, 2H) 7.21 (d, J=8.1 Hz, 2H) 7.14 (d, J=7.9 Hz, 2H) 5.93 (s, 1H) 4.50 (br s, 1H) 2.29 (s, 3H).

Step 2. Preparation of 2-trifluoromethyl-4-phenyl-5-(4-methylphenyl)oxazole.

Trifluoroacetonitrile (1.57 g (16.5 mmol) was added to DMF (100 mL). This solution was cooled to 0° C. and 4'-methylbenzoin from Step 1 (3.05 g, 13.5 mmol) was added. DBU (2.51 g, 16.5 mmol) was added and the solution was warmed to room temperature for 4 hours. The reaction was heated to approximately 100° C. for an additional 4 hours. The solution was cooled to room temperature and poured into 400 mL 1N HCl and extracted with 500 mL ethyl acetate. The organics were washed consecutively with 1N HCl (400 mL), $NaHCO_3$ (saturated) (400 mL) and brine (400 mL), dried over $Na_2SO_4$ and concentrated. The residue was purified by silica gel chromatography eluting with 5% ether in hexane to give a white solid (1.28 g, 31%): mp 54–55° C. Anal. Calc'd. for $C_{17}H_{12}NOF_3$: C, 67.33; H, 3.99; N, 4.62. Found: C, 67.22; H, 3.94; N, 4.55.

Step 3. Preparation of 5-(3-aminosulfonyl-4-methylphenyl)-4-phenyl-2-trifluoromethyloxazole.

2-Trifluoromethyl-4-phenyl-5-(4-methylphenyl) oxazole from Step 2 (0.34 g) was added to chlorosulfonic acid cooled to 0° C. (12 mL) and the reaction was warmed to room temperature for 1.25 hours. The solution was carefully poured into ice water and extracted with three 75 mL portions of dichloromethane. The combined organics were washed once with brine (75 mL) and stirred over ice cold $NH_4OH$ (125 mL) for 2 hours. The dichloromethane layer was separated, washed consecutively with 1N HCl (2×75 mL), $NaHCO_3$ (saturated) (75 mL) and brine (75 mL), dried over $Na_2SO_4$ and concentrated. The crude material was crystallized from ethyl acetate and hexane to yield 2-trifluoromethyl-4-phenyl-5-(3-aminosulfonyl-4-methylphenyl)oxazole (184 mg, 54%): mp 156–157° C. Anal. Calc'd. for $C_{17}H_{13}N_2O_3SF_3$: C, 53.40; H, 3.43; N, 7.33. Found: C, 53.23; H, 3.44; N, 7.31.

EXAMPLE 64

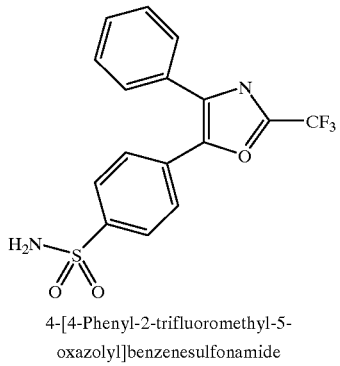

4-[4-Phenyl-2-trifluoromethyl-5-oxazolyl]benzenesulfonamide

Step 1. Preparation of 2-trifluoromethyl-4,5-diphenyloxazole.

Trifluoroacetonitrile (1.58 g, 16.5 mmol) was added to DMF (100 ml). This solution was cooled to 0° C. and benzoin (2.87 g, 13.5 mmol) was added. DBU (2.51 g, 16.5 mmol) was added and the solution was warmed to room temperature for 4 hours. The reaction was heated to approximately 100° C. for an additional 4 hours. The solution was cooled to room temperature and poured into 400 mL 1N HCl and extracted with 500 mL ethyl acetate. The organics were washed consecutively with 1N HCl (400 mL), $NaHCO_3$ (saturated) (400 mL) and brine (400 mL), dried over $Na_2SO_4$ and concentrated. The residue was purified by silica gel chromatography eluting with 5% ether in hexane to give a white solid (1.75 g, 45%): mp 70–71° C. Anal. Calc'd. for $C_{16}H_{10}NOF_3$: C, 66.44; H, 3.48; N, 4.84. Found: C, 67.33; H, 3.52; N, 4.92.

Step 2. Preparation of 4-[4-phenyl-2-trifluoromethyl-5-oxazolyl]benzenesulfonamide.

2-Trifluoromethyl-4,5-diphenyloxazole from Step 1 (0.77 g, 2.8 mmol) was added to chlorosulfonic acid (25 mL) (cooled to 0° C.) and the reaction was stirred from 0° C. to room temperature for 5 hours. The solution was carefully poured into ice water and extracted with three 75 mL portions of dichloromethane. The combined organics were washed once with brine (75 mL) and stirred over ice cold $NH_4OH$ (125 mL) for 2 hours. The dichloromethane layer was separated and washed consecutively with 1N HCl (2×75 mL), $NaHCO_3$ (saturated) (75 mL) and brine (75 mL), dried over $Na_2SO_4$ and concentrated. The crude material was crystallized from ethyl acetate and hexane to yield 4-[4-phenyl-2-trifluoromethyl-5-oxazolyl]benzenesulfonamide (0.56 g, 57%): mp 137–138° C. Anal. Calc'd. for $C_{16}H_{11}N_2O_3SF_3$: C, 52.18; H, 3.01; N, 7.61. Found: C, 52.15; H, 2.98; N, 7.52.

EXAMPLE 65

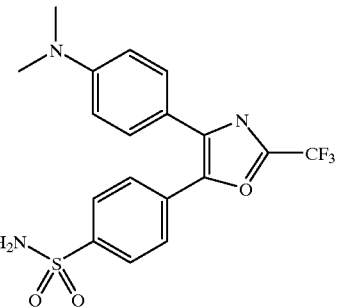

4-[4-Dimethylaminophenyl-2-trifluoromethyl-5-oxazolyl]benzenesulfonamide

Step 1. Preparation of 2-trifluoromethyl-4-(4-dimethylaminophenyl)-5-phenyloxazole.

The oxazole was prepared as described in Example 32 with the substitution of 4-dimethylaminobenzoin (3.06 g, 12 mmol) to give a yellow solid (1.84 g, 46%): mp 120–121° C. Anal. Calc'd. for $C_{18}H_{15}N_2OF_3$: C, 65.06; H, 4.55; N, 8.43. Found: C, 65.96; H, 4.52; N, 8.42.

Step 2. Preparation of 4-[4-Dimethylaminophenyl-2-trifluoromethyl-5-oxazolyl]benzenesulfonamide Example 33 was prepared from the oxazole of Step 1 as described in Example 32, Step 2 (0.38 g, 62%): mp 159–160° C. Anal. Calc'd. for $C_{18}H_{16}N_3O_3SF_3$: C, 52.55; H, 3.92; N. 10.21. Found: C, 52.29; H, 3.98; N, 10.05.

EXAMPLE 66

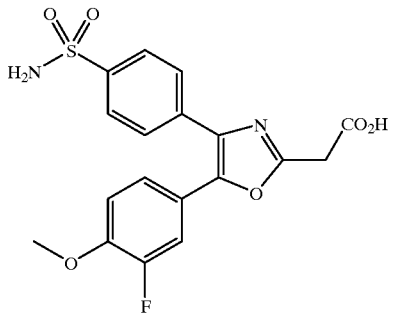

4-(4-Aminosulfonylphenyl)-5-(3-fluoro-4-methoxyphenyl)-2-oxazoleacetic acid

Ethyl [4-(4-aminosulfonylphenyl)-5-(3-fluoro-4-methoxyphenyl)]-2-oxazoleacetate (8.7 mg 0.021 mmol) (Example 34, Step 4) was dissolved in ethanol (1 mL), and a NaOH solution (2.5 N, 18 ml) was added. The reaction was stirred for 0.25 hours at room temperature at which time HCl (aq., concentrated) was added to acidify the reaction. The aqueous solution was extracted with ethyl acetate (dried over $MgSO_4$) and concentrated to yield [4-(4-aminosulfonylphenyl)-5-(3-fluoro-4-methoxyphenyl)]-2-oxazoleacetic acid (6.0 mg, 70%): $^1$H NMR ($CD_3OD$) 300 MHz δ 3.91 (S, 3H), 3.97 (s, 2H), 7.19 (t, 1H), 7.31 (m, 2H), 7.76 (d, J=8.7 Hz, 2H), 7.91 (d, J=8.7 Hz, 2H). $^{19}$F NMR ($CD_3OD$) 282 MHz d-132.8 (multiplet).

EXAMPLE 67

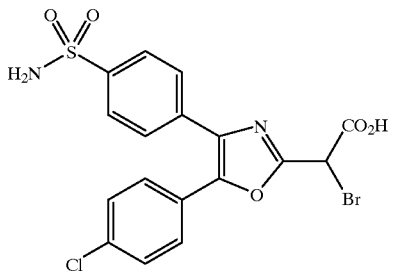

4-[4-Aminosulfonylphenyl)-5-(3-fluoro-4-methoxyphenyl)-2-oxazolyl]α-bromoacetic acid

[4-(4-Aminosulfonylphenyl)-5-(4-chlorophenyl)-2-oxazolyl]acetic acid (Example 66) (65 mg, 0.165 mmol) was dissolved in chloroform (5 mL) and acetic acid (3 mL). Bromine in acetic acid solution (1.1 M, 0.2 mL) was added and the reaction was stirred for 16 hours. Sodium sulfite was added until the orange color dissipated. 1N HCl (10 mL) was added and the reaction concentrated to dryness. The residue was suspended in acetone (2 mL), filtered through Celite® and concentrated to yield 4-[4-aminosulfonylphenyl)-5-(3-fluoro-4-methoxyphenyl)-2-oxazolyl]α-bromoacetic acid (73 mg, 94%): $^1$H NMR (acetone-$d_6$), 300 MHz δ 4.57 (s, 1H), 6.81 (s, 2H), 7.51 (d, J=8.5 Hz, 2H), 7.64 (d, J=8.5 Hz, 2H), 7.79 (d, J=8.3 Hz, 2H), 7.94 (d, J=8.3 Hz, 2H).

EXAMPLE 68

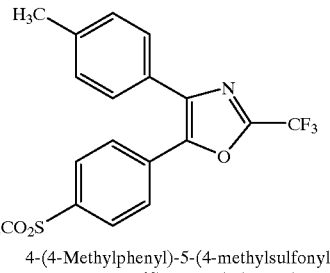

4-(4-Methylphenyl)-5-(4-methylsulfonylphenyl)-2-trifluoromethyloxazole

Step 1. Preparation of 2-hydroxy-2-(4-methylthiophenyl)-1-(4-methylphenyl)ethanone.

A solution of p-thioanisaldehyde (15.22 g, 100 mmol) and zinc iodide (1 g) in dichloromethane (100 mL) was treated with a solution of trimethylsilylcyanide (13.3 mL, 100 mmol) in dichloromethane (50 mL). The solution was stirred for 0.5 hours at room temperature, washed with water and saturated $NaHCO_3$, dried over $MgSO_4$, and concentrated in vacuo to give the trimethylsilyl cyanohydrin as an orange oil (24.9 g). The trimethylsilyl cyanohydrin (5.0 g, 20 mmol) was dissolved in diethyl ether (50 mL) and added dropwise to a solution of p-tolylmagnesium bromide (24 mmol) in diethyl ether (175 mL) while maintaining the temperature at less than 30° C. with an ice water bath. The reaction was stirred for 0.25 hours at room temperature and then quenched by adding 1N HCl (250 mL). The organic layer was collected, washed with saturated $NaHCO_3$ and brine, dried over $MgSO_4$, and concentrated in vacuo to give a yellow solid. The yellow solid was dissolved in 9:1 trifluoroacetic acid/water (30 mL) and stirred for 0.25 hours at room temperature. The reaction was neutralized with saturated $NaHCO_3$ solution, extracted with ethyl acetate, washed with saturated $NaHCO_3$ solution and brine, dried over $MgSO_4$, and concentrated in vacuo to give a yellow oil. The oil was purified by $SiO_2$ chromatography eluting with a gradient from 20–30% ethyl acetate in hexane to yield 2-hydroxy-2-(4-methylthiophenyl)-1-(4-methylphenyl) ethanone (2.8 g, 51%): $^1$H NMR ($CDCl_3$) 300 MHz δ 2.36 (s, 3H), 2.43 (s, 3H), 4.54 (d, J=6.0 Hz, 1H), 5.89 (d, J=6.0 Hz, 1H), 7.20 (m, 6H) 7.80 (d, J=8.3 Hz, 2H).

Step 2. Preparation of 4-(4-methylphenyl)-5-(4-methylthiophenyl)2-trifluoromethyl-oxazole.

The oxazole was prepared as in Example 64, Step 1, with the substitution of 2-hydroxy-2-(4-methylthiophenyl)-1-(4-methylphenyl)ethanone to give a white solid (0.6 g, 46%): mp 129–130° C. Anal. Calc'd. for $C_{18}H_{14}NOSF_3$: C, 61.88; H, 4.04; N, 4.01. Found: C, 61.81; H, 4.09; N, 3.92.

Step 3. 2-trifluoromethyl-4-(4-methylphenyl)-5-(4-methylsulfonylphenyl) oxazole.

4-(4-Methylphenyl)-5-(4-methylthiophenyl)-2-trifluoromethyloxazole from Step 2 (350 mg, 1.0 mmol) was dissolved in THF (20 mL), ethanol (20 mL) and water (20 mL). Oxone® (1.2 g, 2 mmol) was added and the reaction stirred for 3 hours. The reaction mixture was filtered and concentrated to dryness. The residue was dissolved in ethyl acetate (200 mL), washed with water, $NaHCO_3$ and brine, dried and concentrated to yield a white crystalline product (350 mg) which was recrystallized from ethanol and water to yield 4-(4-methylphenyl)-5-(4-methylsulfonylphenyl)-2-trifluoromethyl-oxazole (300 mg, 79%): mp 141–142° C. Anal. Calc'd. for $C_{18}H_{14}NO_3SF_3$: C, 56.69; H, 3.70; N, 3.67. Found: C, 56.47; H, 3.79; N, 3.57.

EXAMPLE 69

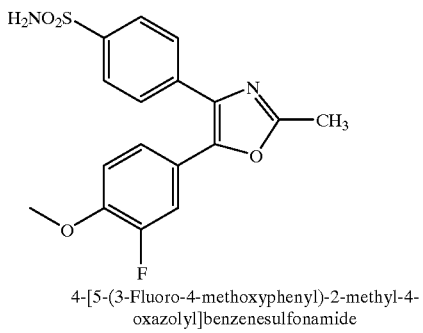

4-[5-(3-Fluoro-4-methoxyphenyl)-2-methyl-4-oxazolyl]benzenesulfonamide

Step 1. Preparation of 5-(3-fluoro-4-methoxyphenyl)2--methyl-4-phenyloxazole.

3-Fluoro-4-methoxybenzoin (Example 34, Step 1) (2.6 g, 10 mmol) and acetic anhydride (1.63 g, 16 mmol) were added to THF (150 mL) and cooled to 0° C. DBU (1.83 g, 12 mmol) was added and the solution was warmed to room temperature for 16 hours. The reaction was poured into 300 mL 1N HCl and extracted with 500 mL ethyl acetate. The organics were washed consecutively with, NaHCO$_3$ (saturated) (400 mL) and brine (400 mL) dried over Na$_2$SO$_4$ and concentrated. Ammonium acetate (6 g) and acetic acid (100 mL) were added to the acetylated benzoin and the solution was heated to reflux for 2.5 hours. The reaction was concentrated to dryness and the residue dissolved in ethyl acetate (250 mL), washed with 1N HCl, NaHCO$_3$ and brine, dried and concentrated to yield a crystalline solid (2.37 g, 65%) which was used without further purification.

Step 2. Preparation of 5-(3-fluoro-4-methoxyphenyl-2-methyl-4-oxazolyl]benzenesulfonamide The oxazole of Step 1 was converted to the sulfonamide by the method of Example 64, Step 2 to yield 4-[5-(3-fluoro-4-methoxyphenyl-2-methyl-4-oxazolyl] benzenesulfonamide (173 mg, 55%): $^1$H NMR (acetone d$_6$), 300 MHz δ 2.52 (s, 3H), 3.96 (s, 3H), 6.61 (s, 2H), 7.24 (m, 1H), 7.37 (m, 2H), 7.81 (d, J=8.5 Hz, 2H), 7.90 (d, J=8.5 Hz, 2H).

EXAMPLE 70

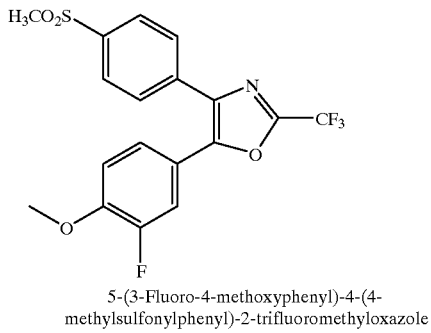

5-(3-Fluoro-4-methoxyphenyl)-4-(4-methylsulfonylphenyl)-2-trifluoromethyloxazole Step 1. Preparation of 4-methylthio-3'-fluoro-4'-methoxybenzoin.

Magnesium (1.34 g, 55 mmol) was suspended in THF (300 mL) and a solution of 4-bromothioanisole (10.16 g, 50 mmol) in THF (50 mL) was added dropwise over 0.5 hour maintaining the temperature at less than 30° C. The reaction was stirred an additional 0.5 hour once the addition was complete. 3-Fluoro-p-anisaldehyde silyl cyanohydrin (Example 34, Step 1) (12.7 g, 50 mmol) and diethyl ether (50 mL) were added dropwise to the solution of Grignard at such a rate that the reaction temperature did not rise above 30° C. Upon complete addition, the reaction was stirred an additional 15 minutes at which time 1N HCl (400 mL) was added and the reaction stirred until all solids were dissolved. The organics were washed with NaHCO$_3$ (saturated) (400 mL) and brine (400 mL), dried over Na$_2$SO$_4$ and concentrated to yield a mixture of benzoin and silyl benzoin. The crude product was dissolved in TFA/H$_2$O (9:1) (75 mL) and stirred for 15 minutes. The TFA solution was poured into saturated NaHCO$_3$ (aq.). The benzoin was extracted with ethyl acetate (350 mL) and washed with NaHCO$_3$ (saturated) (300 mL) and brine (300 mL). The crude benzoin was crystallized from ethyl acetate and hexane to yield crystals of 4-methylthio-3'-fluoro-4'-methoxybenzoin (4.9 g, 32%): $^1$H NMR (CDCl$_3$) 300 MHz δ 2.45 (s, 3H), 3.81 (s, 3H), 5.8 (s, 1H), 6.86 (m, 1H), 7.01 (m, 2H), 7.17 (d, J=8.7 Hz, 2H), 7.79 (d, J=8.7 Hz, 2H); $^{19}$F NMR (CDCl$_3$) 282 MHz δ −134.0 (multiplet).

Step 2. Preparation of 2-trifluoromethyl-4-(4-methylthiophenyl)-5-(3-fluoro-4-methoxyphenyl)oxazole.

5-(3-Fluoro-4-methoxyphenyl)-4-(4-methylthiophenyl)-2-trifluoromethyloxazole was prepared from the benzoin of Step 1 by the method of Example 64, Step 1. The residue was crystallized from ethanol and water to give a white solid (0.26 g, 50%): $^1$H NMR (CDCl$_3$) 300 MHz δ 2.52 (s, 3H), 3.94 (s, 3H), 6.98 (t, J=8.7 Hz, 1H), 7.26 (d, J=8.5 Hz, 2H), 7.36 (m, 2H), 7.55 (d, J=8.5 Hz, 2H); $^{19}$F NMR (CDCl$_3$) 282 MHz δ −66.6 (s), −134.2 (s).

Step 3. Preparation of 5-(3-fluoro-4-methoxyphenyl-4-(4-methylsulfonylphenyl)2-trifluoromethyloxazole.

2-Trifluoromethyl-4-(4-methylthiophenyl)-5-(3-fluoro-4-methoxyphenyl)oxazole from Step 2 (38 mg, 0.1 mmol) was converted by the method of Example 68, Step 3 to yield a white crystalline product which was recrystallized from ethanol and water to yield 5-(3-fluoro-4-methoxyphenyl)-4-(4-methylsulfonylphenyl)-2-trifluoromethyloxazole (39 mg, 94%): $^1$H NMR (CDCl$_3$) 300 MHz δ 3.1 (s, 3H), 3.96 (s, 3H), 6.98 (t, J=8.5 Hz, 1H), 7.36 (m, 2H), 7.88 (d, J=8.5 Hz, 2H), 7.98 (d, J=8.5 Hz, 2H); $^{19}$F NMR (CDCl$_3$) 282 MHz δ −66.6 (s), −133.5 (s). FAB Mass spec. M+H 416.

EXAMPLE 71

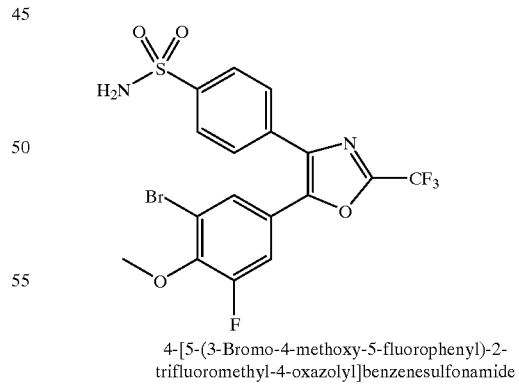

4-[5-(3-Bromo-4-methoxy-5-fluorophenyl)-2-trifluoromethyl-4-oxazolyl]benzenesulfonamide Step 1. Preparation of 3-bromo-5-fluoro-4-hydroxybenzaldehyde.

A solution of 3-fluoro-p-anisaldehyde (10.40 g, 67.5 mmol) in 1,2-dichloroethane (80 mL) was treated with bromine (3.9 mL, 75.6 mmol) then cooled in ice while adding aluminum chloride (11.87 g, 89.0 mmol). The reaction was stirred for 1.75 hours at room temperature and 1.3 hours at 60° C. The excess bromine was quenched by adding 10% sodium bisulfite solution. The reaction mixture was extracted with ethyl acetate, washed with 3N HCl, brine, dried over MgSO$_4$, and concentrated in vacuo to give a white solid (14.84 g, 100%): mp 136–138° C. $^1$H NMR (acetone-d$_6$) 300 MHz δ 10.30 (br s, 1H) 9.86 (d, J=2.0 Hz, 1H) 7.95 (t, J=1.6 Hz, 1H) 7.70 (dd, J=10.3 Hz 1.8 Hz, 1H); $^{19}$F NMR (acetone-d$_6$) 282 MHz –133.27 (m). Mass spectrum: M+H=219/221.

Step 2. Preparation of 3-bromo-5-fluoro-4-methoxybenzaldehyde.

A solution of 3-bromo-5-fluoro-4-hydroxybenzaldehyde from Step 1 (6.01 g, 27.3 mmol) was treated with methyl iodide (8.89 g, 62.6 mmol) and potassium carbonate (5.79 g, 41.9 mmol). The reaction was stirred for 15.1 hours at 50° C., filtered and concentrated in vacuo. The residue was dissolved in ethyl acetate, washed with water, 10% sodium hydroxide, and brine. The organic layer was dried over MgSO$_4$ and concentrated in vacuo to give a brown oil which was crystallized from diethyl ether/hexane to give a white solid (2.63 g, 41%): mp 47–49° C. $^1$H NMR (CDCl$_3$) 300 MHz δ 9.82 (d, J=2.0 Hz, 1H) 7.85 (t, J=1.6 Hz, 1H) 7.58 (dd, J=11.1 Hz 2.0 Hz, 1H) 4.09 (d, J=3.0 Hz, 3H); $^{19}$F NMR (CDCl$_3$) 282 MHz –125.92 (m). Mass spectrum: M+H=233/235.

Step 3. Preparation of 3'-bromo-4'-methoxy-5'-fluorobenzoin.

A solution of 3-bromo-5-fluoro-4-hydroxybenzaldehyde from Step 2 (2.63 g, 11.2 mmol) and zinc iodide (0.44 g) in methylene chloride (10 mL) was treated with trimethylsilyl cyanide (1.7 mL, 12.7 mmol). The solution was stirred for 0.6 hours at room temperature, washed with saturated NaHCO$_3$ and brine, dried over MgSO$_4$, and concentrated in vacuo to give the trimethylsilyl cyanohydrin as a yellow oil (3.04 g). The trimethylsilyl cyanohydrin was dissolved in diethyl ether (15 mL) and added dropwise to a solution of phenylmagnesium bromide (13.8 mmol) in diethyl ether (90 mL) while maintaining the temperature below 25° C. with an ice water bath. The reaction was stirred for 1.2 hours at room temperature then quenched by adding 3N HCl. The organic layer was collected, washed with saturated NaHCO$_3$ and brine, dried over MgSO$_4$, and concentrated in vacuo to give a yellow oil (3.99 g). The yellow oil was dissolved in 9:1 trifluoroacetic acid/water (20 mL) and stirred for 0.33 hours at room temperature. The reaction was neutralized with solid potassium carbonate, extracted with ethyl acetate, washed with 10% Na$_2$CO$_3$ and brine, dried over MgSO$_4$, and concentrated in vacuo to give the benzoin (3.15 g) as a yellow oil which was used in the next step without further purification.

Step 4. Preparation of 5-(3-bromo-4-methoxy-5-fluorophenyl-4-phenyl)-2-trifluoromethyl-oxazole.

5-(3-Bromo-4-methoxy-5-fluorophenyl-4-phenyl)-2-trifluoromethyloxazole was prepared by the method described in Example 64, Step 1, substituting 3'-bromo-4'-methoxy-5'-fluorobenzoin from Step 3. The crystalline solid residue was recrystallized from ether and hexane to yield analytically pure oxazole (1.9 g, 49%): $^1$H NMR (CDCl$_3$) 300 MHz δ 4.03 (s, 3H), 7.32 (m, 1H), 7.44 (m, 3H), 7.63 (m, 3H); $^{19}$F NMR (CDCl$_3$) 282 MHz d –66.6 (s), –126.4 (s).

Step 5. Preparation of 4-[5-(3-bromo-4-methoxy-5-fluorophenyl)-2-trifluoromethyl-4-oxazolyl]benzenesulfonamide The oxazole of Step 4 was reacted as described in Example 64, Step 2. The crude material was chromatographed over SiO$_2$ eluting with a gradient from 10%–50% ethyl acetate in hexane to yield 4-[5-(3-bromo-4-methoxy-5-fluorophenyl)-2-trifluoromethyl-4-oxazolyl]benzenesulfonamide (0.25 g, 15%): $^1$NMR (CDCl$_3$) 300 MHz δ 4.05 (s, 3H), 5.18 (s, 2H), 7.28 (m, 1H), 7.61 (m, 1H), 7.80 (d, J=8.5 Hz, 2H), 7.98 (d, J=8.5 Hz, 2H); $^{19}$F NMR (CDCl$_3$) 282 MHz δ –66.6 (s), –125.7 (s).

EXAMPLE 72

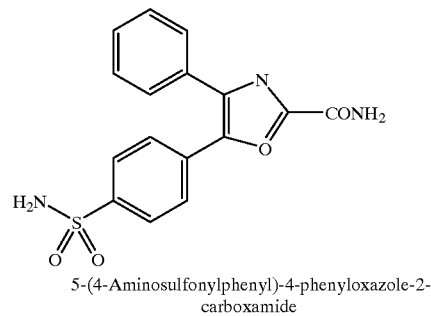

5-(4-Aminosulfonylphenyl)-4-phenyloxazole-2-carboxamide

Step 1. Preparation of 4,5-diphenyloxazole-2-acetic acid methyl ester.

Benzoin (2.12 g, 10 mmol) was dissolved in THF (100 mL) and the solution cooled to 0° C. Methyl oxalylchloride (1.47 g, 12 mmol) and triethylamine (1.67 mL, 12 mmol) were added and the reaction was warmed to room temperature for 2 hours. Ether (150 mL) was added and the reaction mixture was filtered and concentrated. Ammonium acetate (1.5 g) and acetic acid (150 mL) were added to the acylated benzoin and the solution was heated to reflux for 2.5 hours. The reaction was concentrated to dryness, the residue was dissolved in ethyl acetate (250 mL), washed with water, NaHCO$_3$ and brine, dried and concentrated to yield a crystalline solid which was chromatographed over SiO$_2$ eluting with a gradient from 5%–10% ethyl acetate in hexane to yield the methyl ester (0.79 g, 28%): $^1$H NMR (CDCl$_3$) 300 MHz δ 4.02 (s, 3H), 7.36 (m, 6H), 7.67 (m, 4H).

Step 2. Preparation of 5-(4-aminosulfonylphenyl)-4-phenyl-oxazole-2-carboxamide.

4,5-Diphenyloxazole-2-acetic acid methyl ester from Step 1 (790 mg, 2.8 mmol) was added to chlorosulfonic acid cooled to 0° C. (25 mL) and the reaction was warmed to room temperature for 2 hours. The solution was carefully poured into ice water and extracted with three 75 mL portions of dichloromethane. The combined organics were washed once with brine (75 mL) and stirred over ice cold NH$_4$OH (125 mL) for 2.5 hours. The dichloromethane layer was separated and washed consecutively with 1N HCl (2×75 mL), NaHCO$_3$ (saturated) (75 mL) and brine (75 mL), dried over Na$_2$SO$_4$ and concentrated. The crude material was crystallized from a minimum amount of boiling ethyl acetate to yield 5-(4-aminosulfonylphenyl)-4-phenyl-oxazole-2-carboxamide (0.45 g,46%): $^1$H NMR (acetone-d$_6$) 300 MHz δ 6.73 (broad s, 2H), 7.22 (broad s, 2H), 7.48 (m, 3H), 7.68 (m, 2H), 7.84 (d, J=8.5 Hz, 2H), 7.98 (d, J=8.5 Hz, 2H). FAB Mass spec. M+H 344.

EXAMPLE 73

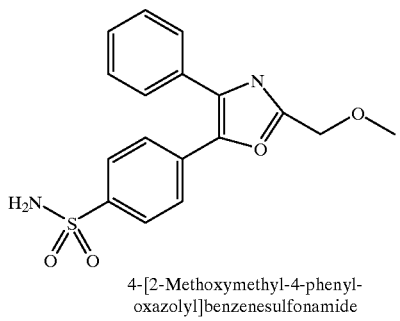

4-[2-Methoxymethyl-4-phenyl-oxazolyl]benzenesulfonamide

Step 1. Preparation of 2-methoxymethyl-4.5-diphenyloxazole.

Benzoin (2.12 g, 10 mmol) was dissolved in THF (50 ML) and the solution cooled to 0° C. Methoxy acetylchloride (2.28 g, 21 mmol) and triethylamine (2.12 mL, 21 mmol) were added and the reaction was warmed to room temperature for 32 hours. Ether (150 mL) was added and the reaction was filtered. The organics were washed with 1N HCl, $NaHCO_3$ and brine, dried over $Na_2SO_4$ and concentrated. Ammonium acetate (1.32 g, 17.1 mmol) and acetic acid (50 mL) were added to the acylated benzoin and the solution was heated to reflux for 3 hours. The reaction was concentrated to dryness, residue was dissolved in ethyl acetate (250 mL), washed with water, $NaHCO_3$ and brine, dried and concentrated to yield a crystalline solid (2.1 g) which was recrystallized from ethyl acetate and hexane to yield 2-methoxymethyl-4,5-diphenyloxazole (0.82 g, 36%): $^1$H NMR ($CDCl_3$) 300 MHz d 3.53 (s, 3H), 4.62 (s, 2H), 7.35 (m, 6H), 7.62 (m, 4H).

Step 2. Preparation of 4-[2-methoxymethyl-4-phenyl-oxazolyl]benzenesulfonamide.

2-Methoxymethyl-4,5-diphenyloxazole from Step 1 (500 mg, 1.9 mmol) was added to chlorosulfonic acid cooled to 0° C. (25 mL) and the reaction allowed was warmed to room temperature for 3 hours. The solution was carefully poured into ice water and extracted with three 75 mL portions of dichloromethane. The combined organics were washed once with brine (75 mL) and stirred over ice cold $NH_4OH$ (125 mL) for 2.5 hours. The dichloromethane layer was separated, washed consecutively with 1N HCl (2×75 mL), $NaHCO_3$ (saturated) (75 mL) and brine (75 mL), dried over $Na_2SO_4$ and concentrated. The crude material was chromatographed over $SiO_2$ eluting with a gradient from 50%–75% ethyl acetate in hexane to yield 4-[2-methoxymethyl-4-phenyl-oxazolyl]benzenesulfonamide (0.22 g, 34%): $^1$H NMR (acetone-$d_6$) 300 MHz δ 3.47 (s, 3H), 4.62 (s, 2H), 6.69 (s, 2H), 7.44 (m, 3H), 7.65 (m, 2H), 7.77 (d, J=8.7 Hz, 2H), 7.93 (d, J=8.7 Hz, 2H). FAB Mass spec. M+H 345.

EXAMPLE 74

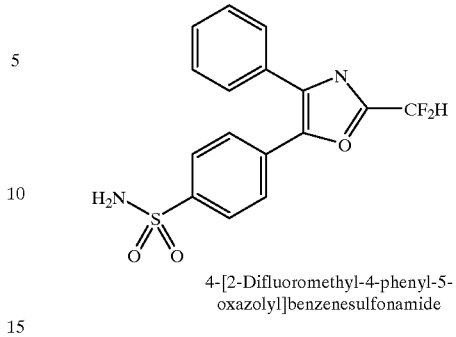

4-[2-Difluoromethyl-4-phenyl-5-oxazolyl]benzenesulfonamide

Step 1. Preparation of 2-difluoromethyl-4.5-diphenyloxazole.

Difluoroacetic acid was dissolved in ethanol containing NaOH (4 mL, 2.5 N), and concentrated to dryness. The solid was re-dissolved in EtOH (50 mL) and re-concentrated to dryness. The salt was suspended in DMF (30 mL) and desylbromide (2.75 g, 10 mmol) was added. The reaction was stirred for 16 hours and concentrated. The residue was dissolved in ethyl acetate (250 mL), washed with 0.1N HCl (75 mL), $NaHCO_3$ (saturated) (75 mL) and brine (75 mL), dried over $Na_2SO_4$ and concentrated to yield 3.09 g of a colorless oil. Ammonium acetate (2.31 g, 30 mmol) and acetic acid (25 mL) were added to the acylated benzoin and the solution was heated to reflux for 3 hours. The reaction was concentrated to dryness, the residue was dissolved in ethyl acetate (250 mL), washed with water, $NaHCO_3$ and brine, dried and concentrated. The crude product was chromatographed over $SiO_2$, eluting with a gradient from 1%–10% ether in hexane, to yield 2-difluoromethyl-4,5-diphenyloxazole (0.35 g, 12%): $^1$H NMR ($CDCl_3$) 300 MHz δ 6.74 (t, J 52.6 Hz, 1H), 7.39 (m, 6H), 7.64 (m, 4H). $^{19}$F NMR ($CDCl_3$) 282 MHz δ −118.6 (d, J 52.9 Hz). FAB Mass spec. M+H 272.

Step 2. Preparation of 4-[2-difluoromethyl-4-phenyl-5-oxazolyl]benzenesulfonamide 2-Difluoromethyl-4,5-diphenyloxazole from Step 1 (320 mg, 1.18 mmol) was added to chlorosulfonic acid cooled to 0° C. (10 mL) and the reaction was warmed to room temperature for 2 hours. The solution was carefully poured into ice water and extracted with three 75 mL portions of dichloromethane. The combined organics were washed once with brine (75 mL) and stirred over ice cold $NH_4OH$ (125 mL) for 2.5 hours. The dichloromethane layer was separated, washed consecutively with 1N HCl (2×75 mL), $NaHCO_3$ (saturated) (75 mL) and brine (75 mL), dried over $Na_2SO_4$ and concentrated. The crude material was chromatographed over $SiO_2$, eluting with a gradient from 20%–50% ethyl acetate in hexane, to yield 4-[2-difluoromethyl-4-phenyl-5-oxazolyl]benzenesulfonamide (0.26 g, 63%): $^1$H NMR ($CD_3OD$) 300 MHz δ 6.99 (t, J 52.2 Hz, 1H), 7.43 (m, 3H), 7.61 (m, 2H), 7.75 (d, J=6.8 Hz, 2H), 7.93 (d, J=6.8 Hz, 2H). $^{19}$F NMR ($CD_3OD$) 282 MHz δ −121.6 (d, J 52.2 Hz).

EXAMPLE 75

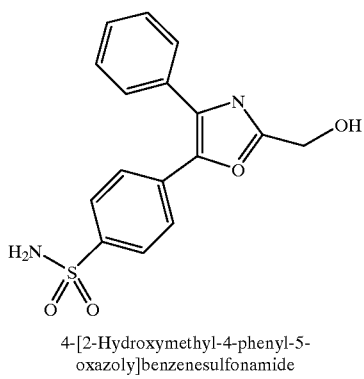

4-[2-Hydroxymethyl-4-phenyl-5-oxazolyl]benzenesulfonamide

Deoxybenzoin (10 g, 51 mmol) was added to chlorosulfonic acid cooled to 0° C. (25 mL) and the reaction was warmed to room temperature for 4 hours. The solution was carefully poured into ice water, filtered and the aqueous layer was extracted with three 250 mL portions of dichloromethane. The combined organics were washed once with brine (75 mL) and stirred over ice-cold $NH_4OH$ (125 mL) for 16 hours. The dichloromethane layer was separated and washed consecutively with 1N HCl (2×75 mL), $NaHCO_3$ (saturated) (75 mL) and brine (75 mL), dried over $Na_2SO_4$ and concentrated. The crude material (4.23 g) was suspended in acetic acid (75 mL) and HBr/HOAc solution (33 u/V% HBr in HOAc, 25 mL) and $Br_2$ (0.79 mL, 15.4 mmol) was added. After 0.25 hours at room temperature the reaction was complete by TLC, and the reaction was concentrated to remove the acetic acid. The residue was dissolved in ethyl acetate (250 mL) and $NaHSO_3$ (10%, 250 mL). The organics were washed with $NaHCO_3$ (saturated) (75 mL) and brine (75 mL), dried over $Na_2SO_4$ and concentrated yielding a crude 4-sulfonamido-desylbromide which was used without purification. Glycolic acid mono sodium salt (1.55 g, 15.8 mmol) and the 4-sulfonamido-desylbromide were suspended in DMF (350 mL) and stirred at room temperature for 16 hours. The reaction was concentrated and the residue, along with ammonium acetate (2.31 g, 30 mmol) and acetic acid (25 mL), were heated to reflux for 3 hours. The reaction was concentrated to dryness. The residue was dissolved in ethyl acetate (250 mL)l, washed with water, $NaHCO_3$ and brine, dried and concentrated. The crude product was chromatographed over $SiO_2$, eluting with a gradient from 50%–75% ethyl acetate in hexane, to yield 4-[2-hydroxymethyl-4-phenyl-5-oxazolyl]benzenesulfonamide: $^1H$ NMR (acetone-$d_6$) 300 MHz δ 4.76 (m, 2H), 6.68 (s, 2H), 7.45 (m, 3H), 7.65 (m, 2H), 7.77 (d, J=6.8 Hz, 2H), 7.94 (d, J=8.7 Hz, 2H).

BIOLOGICAL EVALUATION

Rat Carrageenan Foot Pad Edema Test

The carrageenan foot edema test was performed with materials, reagents and procedures essentially as described by Winter, et al., (*Proc. Soc. Exp. Biol. Med.*, 111, 544 (1962)). Male Sprague-Dawley rats were selected in each group so that the average body weight was as close as possible. Rats were fasted with free access to water for over sixteen hours prior to the test. The rats were dosed orally (1 mL) with compounds suspended in vehicle containing 0.5% methylcellulose and 0.025% surfactant, or with vehicle alone. One hour later a subplantar injection of 0.1 mL of 1% solution of carrageenan/sterile 0.9% saline was administered and the volume of the injected foot was measured with a displacement plethysmometer connected to a pressure transducer with a digital indicator. Three hours after the injection of the carrageenan, the volume of the foot was again measured. The average foot swelling in a group of drug-treated animals was compared with that of a group of placebo-treated animals and the percentage inhibition of edema was determined (Otterness and Bliven, *Laboratory Models for Testing NSAIDs*, in *Non-steroidal Anti-Inflammatory Drugs*, (J. Lombardino, ed. 1985)). The % inhibition shows the % decrease from control paw volume determined in this procedure and the data for selected compounds in this invention are summarized in Table I.

Rat Carrageenan-induced Analgesia Test

The analgesia test using rat carrageenan was performed with materials, reagents and procedures essentially as described by Hargreaves, et al., (*Pain*, 32, 77 (1988)). Male Sprague-Dawley rats were treated as previously described for the Carrageenan Foot Pad Edema test. Three hours after the injection of the carrageenan, the rats were placed in a special plexiglass container with a transparent floor having a high intensity lamp as a radiant heat source, positionable under the floor. After an initial twenty minute period, thermal stimulation was begun on either the injected foot or on the contralateral uninjected foot. A photoelectric cell turned off the lamp and timer when light was interrupted by paw withdrawal. The time until the rat withdraws its foot was then measured. The withdrawal latency in seconds was determined for the control and drug-treated groups, and percent inhibition of the hyperalgesic foot withdrawal determined. Results are shown in Table I.

TABLE I

| Example | RAT PAW EDEMA % Inhibition @ 10 mg/kg body weight | ANALGESIA % Inhibition @ 20 mg/kg body weight |
|---|---|---|
| 1 | 41* | 44 |
| 3 | 30 | — |
| 7 | 24 | — |
| 8 | 12 | — |
| 10 | 18 | — |
| 11 | 42 | — |
| 16 | 26 | — |
| 28 | 2 | — |
| 30 | 4 | — |
| 31 | 5 | — |
| 55 | 37[1] | — |
| 70 | 46[1] | — |

[1] @ 30 mg/kg body weight
* @ 20 mg/kg body weight

Evaluation of COX I and COX II activity in vitro

The compounds of this invention exhibited inhibition in vitro of COX-2. The COX-2 inhibition activity of the compounds of this invention illustrated in the Examples was determined by the following methods.

a. Preparation of recombinant COX baculoviruses

Recombinant COX-1 and COX-2 were prepared as described by Gierse et al, [*J. Biochem.*, 305, 479–84 (1995)]. A 2.0 kb fragment containing the coding region of either human or murine COX-1 or human or murine COX-2 was cloned into a BamH1 site of the baculovirus transfer vector pVL1393 (Invitrogen) to generate the baculovirus transfer vectors for COX-1 and COX-2 in a manner similar to the method of D. R. O'Reilly et al (*Baculovirus Expression Vectors: A Laboratory Manual* (1992)). Recombinant baculoviruses were isolated by transfecting 4 μg of baculovirus transfer vector DNA into SF9 insect cells (2×10$^8$) along with 200 ng of linearized baculovirus plasmid DNA by the calcium phosphate method. See M. D. Summers and G. E. Smith, *A Manual of Methods for Baculovirus vectors and Insect Cell Culture Procedures,* Texas Agric. Exp. Station Bull. 1555 (1987). Recombinant viruses were purified by three rounds of plaque purification and high titer ($10^7$–$10^8$ pfu/ml) stocks of virus were prepared. For large scale production, SF9 insect cells were infected in 10 liter fermentors ($0.5\times10^6$/ml) with the recombinant baculovirus stock such that the multiplicity of infection was 0.1. After 72 hours the cells were centrifuged and the cell pellet homogenized in Tris/Sucrose (50 mM: 25%, pH 8.0) containing 1% 3-[(3-cholamidopropyl)dimethylammonio]-1-propanesulfonate (CHAPS). The homogenate was centrifuged at 10,000×G for 30 minutes, and the resultant supernatant was stored at −80° C. before being assayed for COX activity.

b. Assay for COX-1 and COX-2 activity

COX activity was assayed as $PGE_2$ formed/μg protein/time using an ELISA to detect the prostaglandin released. CHAPS-solubilized insect cell membranes containing the appropriate COX enzyme were incubated in a potassium phosphate buffer (50 mM, pH 8.0) containing epinephrine, phenol, and heme with the addition of arachidonic acid (10 μM). Compounds were pre-incubated with the enzyme for 10–20 minutes prior to the addition of arachidonic acid. Any reaction between the arachidonic acid and the enzyme was stopped after ten minutes at 37° C./room temperature by transferring 40 μl of reaction mix into 160 μl ELISA buffer and 25 μM indomethacin. The $PGE_2$ formed was measured by standard ELISA technology (Cayman Chemical). Results are shown in Table II.

TABLE II

| Example | COX-1 $ID_{50}$ μM | COX II $ID_{50}$ μM |
|---|---|---|
| 1 | 6.9 | <.1 |
| 3 | >10 | <0.1 |
| 14 | >30 | >10 |
| 15 | >30 | 0.2 |
| 25 | >10 | 0.5 |
| 28 | >100 | <0.1 |
| 29 | >100 | 100 |
| 30 | >100 | <0.1 |
| 31 | >100 | <0.1 |
| 32 | 15.9 | <0.1 |
| 33 | 3.1 | 0.05 |
| 34 | 0.2 | <0.1 |
| 35 | 72 | 7.9 |
| 36 | 24.7 | 1.4 |
| 37 | 3.4 | 7.0 |
| 38 | 72 | <0.1 |
| 39 | >100 | 79 |
| 40 | 26 | <0.1 |
| 41 | >100 | 60.7 |
| 42 | 11.4 | <0.1 |
| 43 | 2.3 | 3.1 |
| 44 | >100 | 79 |
| 45 | 6.5 | <0.1 |
| 46 | 1.7 | 0.5 |
| 47 | 1.0 | <0.1 |
| 48 | 0.3 | 2.1 |
| 49 | 4.1 | <0.1 |
| 50 | 7.4 | <0.1 |
| 51 | 14.0 | <0.1 |
| 52 | 35 | 0.2 |
| 53 | >100 | 0.5 |
| 54 | 3.0 | <0.1 |
| 55 | 9.7 | <0.1 |
| 56 | 4.5 | <0.1 |
| 57 | 3.2 | <0.1 |
| 58 | 31.0 | <0.1 |

TABLE II-continued

| Example | COX-1 $ID_{50}$ μM | COX II $ID_{50}$ μM |
|---|---|---|
| 59 | .4 | <0.1 |
| 60 | 2.2 | <0.1 |
| 64 | 1.1 | <0.1 |
| 65 | <0.1 | <0.1 |
| 66 | 21 | 13 |
| 67 | 33 | 0.8 |
| 68 | 2.0 | <0.1 |
| 69 | 79 | 0.5 |
| 70 | >100 | <0.1 |
| 71 | 51 | 0.1 |
| 72 | >100 | 2.2 |
| 73 | 47.5 | <0.1 |
| 74 | 4.9 | <0.1 |
| 75 | >100 | <0.1 |

Also embraced within this invention is a class of pharmaceutical compositions comprising one or more compounds of Formula I in association with one or more non-toxic, pharmaceutically acceptable carriers and/or diluents and/or adjuvants (collectively referred to herein as "carrier" materials) and, if desired, other active ingredients. The compounds of the present invention may be administered by any suitable route, preferably in the form of a pharmaceutical composition adapted to such a route, and in a dose effective for the treatment intended. The compounds and composition may, for example, be administered intravascularly, intraperitoneally, subcutaneously, intramuscularly or topically.

For oral administration, the pharmaceutical composition may be in the form of, for example, a tablet, capsule, suspension or liquid. The pharmaceutical composition is preferably made in the form of a dosage unit containing a particular amount of the active ingredient. Examples of such dosage units are tablets or capsules. The active ingredient may also be administered by injection as a composition wherein, for example, saline, dextrose or water may be used as a suitable carrier.

The amount of therapeutically active compound that is administered and the dosage regimen for treating a disease condition with the compounds and/or compositions of this invention depends on a variety of factors, including the age, weight, sex and medical condition of the subject, the severity of the disease, the route and frequency of administration, and the particular compound employed, and thus may vary widely. The pharmaceutical compositions may contain active ingredient in the range of about 0.1 to 1000 mg, preferably in the range of about 0.5 to 500 mg and most preferably between about 1 and 100 mg. A daily dose of about 0.01 to 100 mg/kg body weight, preferably between about 0.1 and about 50 mg/kg body weight and most preferably from about 1 to 20 mg/kg body weight, may be appropriate. The daily dose can be administered in one to four doses per day.

For therapeutic purposes, the compounds of this invention are ordinarily combined with one or more adjuvants appropriate to the indicated route of administration. If administered per os, the compounds may be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, and then tableted or encapsulated for convenient administration. Such capsules or tablets may contain a controlled-release formulation as may be provided in a dispersion of active compound in hydroxypropylmethyl cellulose. Formulations for parenteral administration may be in the form of aqueous or non-aqueous isotonic sterile injection solutions or suspensions. These solutions and suspensions may be prepared from sterile powders or granules having one or more of the carriers or diluents mentioned for use in the formulations for oral administration. The compounds may be dissolved in water, polyethylene glycol, propylene glycol, ethanol, corn oil, cottonseed oil, peanut oil, sesame oil, benzyl alcohol, sodium chloride, and/or various buffers. Other adjuvants and modes of administration are well and widely known in the pharmaceutical art.

While the compounds of the invention can be administered as the sole active pharmaceutical agent, they can also be used in combination with one or more immunomodulators, antiviral agents or other antiinfective agents. For example, the compounds of the invention can be administered in combination with antihistamines or with other such agents known heretofore to be effective in combination with antiinflammatory agents. When administered as a combination, the therapeutic agents can be formulated as separate compositions which are given at the same time or different times, or the therapeutic agents can be given as a single composition.

The examples herein can be repeated with similar success by substituting the generically or specifically described reactants and/or operating conditions of this invention for those used in the preceding examples.

The foregoing is merely illustrative of the invention and is not intended to limit the invention to the disclosed compounds. Variations and changes which are obvious to one skilled in the art are intended to be with in the scope and nature of the invention which are defined in the appended claims. Although this invention has been described with respect to specific embodiments, the details of these embodiments are not to be construed as limitations.

What is claimed is:

1. A compound of Formula I

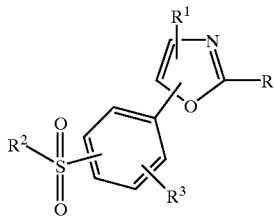

I wherein R is selected from hydrido, mercapto, hydroxyl, carboxymethylthio, carboxyethylthio, trifluoromethoxy, methylthio, ethylthio, methylsulfinyl, methylsulfonyl, methoxy, ethoxy, propoxy, butoxy, phenyloxy, benzyloxy, N-methylamino, N,N-dimethylamino, N,N-diethylamino, aminocarbonyl, methoxymethyl, a-bromo-carboxymethyl, methyl, ethyl, n-propyl, isopropyl, butyl, tert-butyl, isobutyl, hydroxymethyl, fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl, dichloropropyl, ethenyl, 1-propenyl, 2-propenyl, 1-butenyl, 2-butenyl, 3-butenyl, hydroxyethenyl, ethynyl, 1-propynyl, 2-propynyl, 1-butynyl, 2-butynyl, 3-butynyl, hydroxyethynyl, cyclobutyl, cyclopentyl, cyclohexyl, cycloheptyl, cyclobutylmethyl, cyclopentylmethyl, cyclohexylmethyl, cyclohexylethyl, cyclohexylpropyl, cycloheptylmethyl, phenyl and naphthyl, optionally substituted at a substitutable position by fluoro, chloro, bromo, iodo, carboxy, methyl, ethyl, n-propyl, isopropyl, butyl, tert-butyl, isobutyl, methoxy, ethoxy, propoxy and butoxy, pyridyl, thienyl, thiazolyl, oxazolyl, imidazolyl, furyl and quinolyl, optionally substituted at a substitutable position by fluoro, chloro, bromo, iodo, carboxy, methyl, ethyl, n-propyl, isopropyl, butyl, tert-butyl, isobutyl, methoxy, ethoxy, propoxy and butoxy, benzyl, phenethyl, diphenylmethyl and phenylpropyl, optionally substituted at a substitutable position on the phenyl radical by fluoro, chloro, bromo, iodo, carboxy, methyl, ethyl, n-propyl, isopropyl, butyl, tert-butyl, isobutyl, methoxy, ethoxy, propoxy and butoxy, phenoxymethyl optionally substituted at a substitutable position on the phenyl radical with fluoro, chloro, bromo, iodo, carboxy, methyl, ethyl, n-propyl, isopropyl, butyl, tert-butyl, isobutyl, methoxy, ethoxy, propoxy and butoxy, benzyloxymethyl optionally substituted at a substitutable position on the phenyl radical with fluoro, chloro, bromo, iodo, carboxy, methyl, ethyl, n-propyl, isopropyl, butyl, tert-butyl, isobutyl, methoxy, ethoxy, propoxy and butoxy, pyridyloxymethyl and quinolyloxymethyl optionally substituted at a substitutable position with fluoro, chloro, bromo, iodo, carboxy, methyl, ethyl, n-propyl, isopropyl, butyl, tert-butyl, isobutyl, methoxy, ethoxy, propoxy and butoxy, methoxycarbonyl, ethoxycarbonyl, propoxycarbonyl, butoxycarbonyl, methoxycarbonylmethyl, ethoxycarbonylmethyl, methoxycarbonylethyl, ethoxycarbonylethyl, carboxy, acetyl, propanoic, butanoic, pentanoic, hexanoic, phenylthiomethyl, aminocarbonylmethyl, N-methylaminocarbonylmethyl and N,N-dimethylaminocarbonylmethyl; wherein $R^1$ is selected from cyclobutyl, cyclopentyl, cyclohexyl, cycloheptyl, 1-cyclohexenyl, 2-cyclohexenyl, 3-cyclohexenyl, cyclopentenyl, cycloheptenyl, phenyl, naphthyl, pyridyl, thienyl, thiazolyl, oxazolyl, imidazolyl, furyl, quinolyl, benzothiazolyl, 2,3-thianaphthalenyl, 2,3-dihydrothianaphthalenyl, 2,3-benzofuryl, and 2,3-dihydrobenzofuryl, wherein $R^1$ is optionally substituted at a substitutable position by methyl, ethyl, n-propyl, isopropyl, butyl, tert-butyl, isobutyl, amino, methoxy, ethoxy, propoxy, butoxy, N-methylamino, N,N-dimethylamino, fluoro, chloro, bromo and iodo; wherein $R^2$ is selected from methyl, and amino; wherein $R^3$ represents one or two radicals selected from fluoro, methoxy and methyl; or a pharmaceutically-acceptable salt thereof.

2. Compound of claim 1 selected from compounds, and their pharmaceutically-acceptable salts, of the group consisting of 4-methyl-3-[5-phenyl-2-trifluoromethyl-4-oxazolyl] benzenesulfonamide;

4-methyl-3-[4-phenyl-2-trifluoromethyl-5-oxazolyl] benzenesulfonamide; and 5-fluoro-4-methoxy-3-[5-phenyl-2-trifluoromethyl-4-oxazolyl]benzenesulfonamide.

3. A pharmaceutical composition comprising a therapeutically-effective amount of a compound, said compound selected from a family of compounds of Formula I

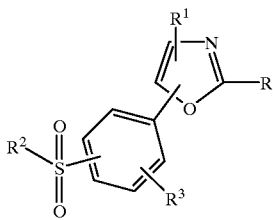

wherein R is selected from hydrido, mercapto, hydroxyl, carboxymethylthio, carboxyethylthio, trifluoromethoxy, methylthio, ethylthio, methylsulfinyl, methylsulfonyl, methoxy, ethoxy, propoxy, butoxy, phenyloxy, benzyloxy, N-methylamino, N,N-dimethylamino, N,N-diethylamino, aminocarbonyl, methoxymethyl, a-bromo-carboxymethyl, methyl, ethyl, n-propyl, isopropyl, butyl, tert-butyl, isobutyl, hydroxymethyl, fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl, dichloropropyl, ethenyl, 1-propenyl, 2-propenyl, 1-butenyl, 2-butenyl, 3-butenyl, hydroxyethenyl, ethynyl, 1-propynyl, 2-propynyl, 1-butynyl, 2-butynyl, 3-butynyl, hydroxyethynyl, cyclobutyl, cyclopentyl, cyclohexyl, cycloheptyl, cyclobutylmethyl, cyclopentylmethyl, cyclohexylmethyl, cyclohexylethyl, cyclohexylpropyl, cycloheptylmethyl, phenyl and naphthyl, optionally substituted at a substitutable position by fluoro, chloro, bromo, iodo, carboxy, methyl, ethyl, n-propyl, isopropyl, butyl, tert-butyl, isobutyl, methoxy, ethoxy, propoxy and butoxy, pyridyl, thienyl, thiazolyl, oxazolyl, imidazolyl, furyl and quinolyl, optionally substituted at a substitutable position by fluoro, chloro, bromo, iodo, carboxy, methyl, ethyl, n-propyl, isopropyl, butyl, tert-butyl, isobutyl, methoxy, ethoxy, propoxy and butoxy, benzyl, phenethyl, diphenylmethyl and phenylpropyl, optionally substituted at a substitutable position on the phenyl radical by fluoro, chloro, bromo, iodo, carboxy, methyl, ethyl, n-propyl, isopropyl, butyl, tert-butyl, isobutyl, methoxy, ethoxy, propoxy and butoxy, phenoxymethyl optionally substituted at a substitutable position on the phenyl radical with fluoro, chloro, bromo, iodo, carboxy, methyl, ethyl, n-propyl, isopropyl, butyl, tert-butyl, isobutyl, methoxy, ethoxy, propoxy and butoxy, benzyloxymethyl optionally substituted at a substitutable position on the phenyl radical with fluoro, chloro, bromo, iodo, carboxy, methyl, ethyl, n-propyl, isopropyl, butyl, tert-butyl, isobutyl, methoxy, ethoxy, propoxy and butoxy, pyridyloxyymethyl and quinolyloxymethyl optionally substituted at a substitutable position with fluoro, chloro, bromo, iodo, carboxy, methyl, ethyl, n-propyl, isopropyl, butyl, tert-butyl, isobutyl, methoxy, ethoxy, propoxy and butoxy, methoxycarbonyl, ethoxycarbonyl, propoxycarbonyl, butoxycarbonyl, methoxycarbonylmethyl, ethoxycarbonylmethyl, methoxycarbonylethyl, ethoxycarbonylethyl, carboxy, acetyl, propanoic, butanoic, pentanoic, hexanoic, phenylthiomethyl, aminocarbonylmethyl, N-methylaminocarbonylmethyl and N,N-dimethylaminocarbonylmethyl; wherein $R^1$ is selected from cyclobutyl, cyclopentyl, cyclohexyl, cycloheptyl, 1-cyclohexenyl, 2-cyclohexenyl, 3-cyclohexenyl, cyclopentenyl, cycloheptenyl, phenyl, naphthyl, pyridyl, thienyl, thiazolyl, oxazolyl, imidazolyl, furyl, quinolyl, benzothiazolyl, 2,3-thianaphthalenyl, 2,3-dihydrothianaphthalenyl, 2,3-benzofuryl, and 2,3-dihydrobenzofuryl, wherein $R^1$ is optionally substituted at a substitutable position by methyl, ethyl, n-propyl, isopropyl, butyl, tert-butyl, isobutyl, amino, methoxy, ethoxy, propoxy, butoxy, N-methylamino, N,N-dimethylamino, fluoro, chloro, bromo and iodo; wherein $R^2$ is selected from methyl, and amino; wherein $R^3$ represents one or two radicals selected from fluoro, methoxy and methyl; or a pharmaceutically-acceptable salt thereof.

4. The composition of claim 3 selected from compounds, and their pharmaceutically-acceptable salts, of the group consisting of 4-methyl-3-[5-phenyl-2-trifluoromethyl-4-oxazolyl] benzenesulfonamide;

4-methyl-3-[4-phenyl-2-trifluoromethyl-5-oxazolyl] benzenesulfonamide; and 5-fluoro-4-methoxy-3-[5-phenyl-2-trifluoromethyl-4-oxazolyl]benzenesulfonamide.

5. A method of treating inflammation or an inflammation-associated disorder in a subject, said method comprising administering to the subject having or susceptible to said inflammation or inflammation-associated disorder, a therapeutically-effective amount of a compound of Formula I

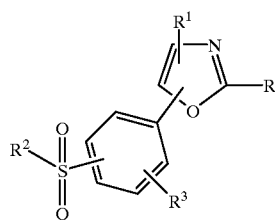

wherein R is selected from hydrido, mercapto, hydroxyl, carboxymethylthio, carboxyethylthio, trifluoromethoxy, methylthio, ethylthio, methylsulfinyl, methylsulfonyl, methoxy, ethoxy, propoxy, butoxy, phenyloxy, benzyloxy, N-methylamino, N,N-dimethylamino, N,N-diethylamino, aminocarbonyl, methoxymethyl, a-bromo-carboxymethyl, methyl, ethyl, n-propyl, isopropyl, butyl, tert-butyl, isobutyl, hydroxymethyl, fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl, dichloropropyl, ethenyl, 1-propenyl, 2-propenyl, 1-butenyl, 2-butenyl, 3-butenyl, hydroxyethenyl, ethynyl, 1-propynyl, 2-propynyl, 1-butynyl, 2-butynyl, 3-butynyl, hydroxyethynyl, cyclobutyl, cyclopentyl, cyclohexyl, cycloheptyl, cyclobutylmethyl, cyclopentylmethyl, cyclohexylmethyl, cyclohexylethyl, cyclohexylpropyl, cycloheptylmethyl, phenyl and naphthyl, optionally substituted at a substitutable position by fluoro, chloro, bromo, iodo, carboxy, methyl, ethyl, n-propyl, isopropyl, butyl, tert-butyl, isobutyl, methoxy, ethoxy, propoxy and butoxy, pyridyl, thienyl, thiazolyl, oxazolyl, imidazolyl, furyl and quinolyl, optionally substituted at a substitutable position by fluoro, chloro, bromo, iodo, carboxy, methyl, ethyl, n-propyl, isopropyl, butyl, tert-butyl, isobutyl, methoxy, ethoxy, propoxy and butoxy, benzyl, phenethyl, diphenylmethyl and phenylpropyl, optionally substituted at a substitutable position on the phenyl radical by fluoro, chloro, bromo, iodo, carboxy, methyl, ethyl, n-propyl, isopropyl, butyl, tert-butyl, isobutyl, methoxy, ethoxy, propoxy and butoxy, phenoxymethyl optionally substituted at a substitutable position on the phenyl radical with fluoro, chloro, bromo, iodo, carboxy, methyl, ethyl, n-propyl, isopropyl, butyl, tert-butyl, isobutyl, methoxy, ethoxy, propoxy and butoxy, benzyloxymethyl optionally substituted at a substitutable position on the phenyl radical with fluoro, chloro, bromo, iodo, carboxy, methyl, ethyl, n-propyl, isopropyl, butyl, tert-butyl, isobutyl, methoxy, ethoxy, propoxy and butoxy, pyridyloxymethyl and quinolyloxymethyl optionally substituted at a substitutable position with fluoro, chloro, bromo, iodo, carboxy, methyl, ethyl, n-propyl, isopropyl, butyl, tert-butyl, isobutyl, methoxy, ethoxy, propoxy and butoxy, methoxycarbonyl, ethoxycarbonyl, propoxycarbonyl, butoxycarbonyl, methoxycarbonylmethyl, ethoxycarbonylmethyl, methoxycarbonylethyl, ethoxycarbonylethyl, carboxy, acetyl, propanoic, butanoic, pentanoic, hexanoic, phenylthiomethyl, aminocarbonylmethyl, N-methylaminocarbonylmethyl and N,N-dimethylaminocarbonylmethyl; wherein $R^1$ is selected from cyclobutyl, cyclopentyl, cyclohexyl, cycloheptyl, 1-cyclohexenyl, 2-cyclohexenyl, 3-cyclohexenyl, cyclopentenyl, cycloheptenyl, phenyl, naphthyl, pyridyl, thienyl, thiazolyl, oxazolyl, imidazolyl, furyl, quinolyl, benzothiazolyl, 2,3-thianaphthalenyl, 2,3-dihydrothianaphthalenyl, 2,3-benzofuryl, and 2,3-dihydrobenzofuryl, wherein $R^1$ is optionally substituted at a substitutable position by methyl, ethyl, n-propyl, isopropyl, butyl, tert-butyl, isobutyl, amino, methoxy, ethoxy, propoxy, butoxy, N-methylamino, N,N-dimethylamino, fluoro, chloro, bromo and iodo; wherein $R^2$ is selected from methyl, and amino; wherein $R^3$ represents one or two radicals selected from fluoro, methoxy and methyl; or a pharmaceutically-acceptable salt thereof.

6. The method of claim 5 selected from compounds, and their pharmaceutically-acceptable salts, of the group consisting of 4-methyl-3-[5-phenyl-2-trifluoromethyl-4-oxazolyl] benzenesulfonamide;

4-methyl-3-[4-phenyl-2-trifluoromethyl-5-oxazolyl] benzenesulfonamide; and 5-fluoro-4-methoxy-3-[5-phenyl-2-trifluoromethyl-4-oxazolyl]benzenesulfonamide.

7. The method of claim 6 for the treatment of inflammation.

8. The method of claim 6 for the treatment of an inflammation-associated disorder.

9. The method of claim 8 wherein the inflammation-associated disorder is arthritis.

10. The method of claim 8 wherein the inflammation-associated disorder is pain.

11. The method of claim 8 wherein the inflammation-associated disorder is fever.

* * * * *